(12) United States Patent
Darley et al.

(10) Patent No.: US 7,428,471 B2
(45) Date of Patent: Sep. 23, 2008

(54) MONITORING ACTIVITY OF A USER IN LOCOMOTION ON FOOT

(75) Inventors: Jesse Darley, Madison, WI (US); Thomas P. Blackadar, Natick, MA (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 11/588,589

(22) Filed: Oct. 27, 2006

(65) Prior Publication Data

US 2007/0061105 A1 Mar. 15, 2007

Related U.S. Application Data

(63) Continuation of application No. 11/098,788, filed on Apr. 4, 2005, now Pat. No. 7,200,517, which is a continuation of application No. 09/643,191, filed on Aug. 21, 2000, now Pat. No. 6,898,550, which is a continuation-in-part of application No. 09/164,654, filed on Oct. 1, 1998, now Pat. No. 6,122,340, said application No. 09/643,191 is a continuation-in-part of application No. 09/521,073, filed on Mar. 7, 2000, now Pat. No. 6,560,903, said application No. 09/643,191 is a continuation-in-part of application No. 09/548,217, filed on Apr. 12, 2000, now abandoned, which is a continuation-in-part of application No. 09/364,559, filed on Jul. 30, 1999, now Pat. No. 6,052,654, said application No. 09/643,191 is a continuation-in-part of application No. 09/547,976, filed on Apr. 12, 2000, now abandoned, which is a continuation-in-part of application No. 09/364,559, filed on Jul. 30, 1999, now Pat. No. 6,052,654, said application No. 09/643,191 is a continuation-in-part of application No. 09/547,977, filed on Apr. 12, 2000, now abandoned, which is a continuation-in-part of application No. 09/364,559, filed on Jul. 30, 1999, now Pat. No. 6,052,654, said application No. 09/643,191 is a continuation-in-part of application No. 09/547,975, filed on Apr. 12, 2000, now abandoned, which is a continuation-in-part of application No. 09/364,559, filed on Jul. 30, 1999, now Pat. No. 6,052,654, which is a continuation of application No. 08/942,802, filed on Oct. 2, 1997, now Pat. No. 6,018,705, said application No. 09/643,191 is a continuation-in-part of application No. 09/382,049, filed on Aug. 24, 1999, now Pat. No. 6,336,365.

(51) Int. Cl.
*G01P 1/00* (2006.01)

(52) U.S. Cl. .................. 702/182; 702/160; 702/141; 702/142; 702/144; 702/176; 73/597; 36/132; 36/136; 377/23; 377/24.2

(58) Field of Classification Search ................ 702/182, 702/160, 141–142, 144, 176; 73/597; 36/132, 36/136; 377/23, 24.2
See application file for complete search history.

(56) References Cited

U.S. PATENT DOCUMENTS 2,233,544 A 3/1941 McKinley (Continued)

*Primary Examiner*—John E. Barlow
*Assistant Examiner*—Hien X Vo
(74) *Attorney, Agent, or Firm*—Banner & Witcoff, Ltd.

(57) ABSTRACT

A user in locomotion on foot during an outing may identify a grade of a surface with at least one device supported by the user. A performance parameter of the user may be determined with the device based upon the grade of the surface, which may be based upon a measured physiological parameter of the user. An average foot contact time and an average pace of a user during a first outing may be identified and a relationship between them may be determined. No other average foot contact times or average paces identified during a different outing may be used to define the relationship. A single user-specific calibration contestant may define a relationship between foot contact times of a user and corresponding paces of the user, wherein no other user-specific calibration constants are used to define the relationship.

5 Claims, 42 Drawing Sheets

U.S. PATENT DOCUMENTS

| | | |
|---|---|---|
| 3,699,672 A | 10/1972 | Sims |
| 3,702,999 A | 11/1972 | Gradisar |
| 3,840,726 A | 10/1974 | Harrison |
| 3,972,038 A | 7/1976 | Fletcher et al. |
| 3,974,491 A | 8/1976 | Sipe |
| 4,019,030 A | 4/1977 | Tamiz |
| 4,120,052 A | 10/1978 | Butler |
| 4,175,446 A | 11/1979 | Crowninshield et al. |
| 4,247,908 A | 1/1981 | Lockhart, Jr. et al. |
| 4,371,945 A | 2/1983 | Karr et al. |
| 4,402,147 A | 9/1983 | Wu |
| 4,408,183 A | 10/1983 | Wills |
| 4,409,992 A | 10/1983 | Sidorenko et al. |
| 4,485,529 A | 12/1984 | Blum |
| 4,499,394 A | 2/1985 | Koal |
| 4,510,704 A | 4/1985 | Johnson |
| 4,578,769 A | 3/1986 | Frederick |
| 4,649,552 A | 3/1987 | Yukawa |
| 4,651,446 A | 3/1987 | Yukawa et al. |
| 4,675,960 A | 6/1987 | Higgins, Jr. |
| 4,745,564 A | 5/1988 | Tennes et al. |
| 4,757,714 A | 7/1988 | Purdy et al. |
| 4,763,287 A | 8/1988 | Gerhaeuser et al. |
| 4,771,394 A | 9/1988 | Cavanagh |
| 4,774,679 A | 9/1988 | Carlin |
| 4,814,661 A | 3/1989 | Ratzlaff et al. |
| 4,817,306 A | 4/1989 | Bayer |
| 4,823,426 A | 4/1989 | Bragga |
| 4,829,540 A | 5/1989 | Waggener, Sr. et al. |
| 4,830,021 A | 5/1989 | Thornton |
| 4,855,942 A | 8/1989 | Bianco |
| 4,897,947 A | 2/1990 | Kass-Pious |
| 4,932,914 A | 6/1990 | Aranda |
| 4,956,628 A | 9/1990 | Furlong |
| 4,962,469 A | 10/1990 | Ono et al. |
| 5,029,183 A | 7/1991 | Tymes |
| 5,033,013 A | 7/1991 | Kato et al. |
| 5,063,690 A | 11/1991 | Slenker |
| 5,063,782 A | 11/1991 | Kellett |
| 5,186,062 A | 2/1993 | Roost |
| 5,241,542 A | 8/1993 | Natarajan et al. |
| 5,269,081 A | 12/1993 | Gray |
| 5,285,586 A | 2/1994 | Goldston et al. |
| 5,311,679 A | 5/1994 | Birch, Sr. |
| 5,313,719 A | 5/1994 | Koethe |
| 5,323,650 A | 6/1994 | Fullen et al. |
| 5,343,445 A | 8/1994 | Cherdak |
| 5,357,696 A | 10/1994 | Gray et al. |
| 5,361,778 A | 11/1994 | Seitz |
| 5,404,577 A | 4/1995 | Zuckerman et al. |
| 5,416,779 A | 5/1995 | Barnes et al. |
| 5,422,628 A | 6/1995 | Rodgers |
| 5,437,289 A | 8/1995 | Liverance et al. |
| 5,452,269 A | 9/1995 | Cherdak |
| 5,479,441 A | 12/1995 | Tymes et al. |
| 5,485,402 A | 1/1996 | Smith et al. |
| 5,502,903 A | 4/1996 | Barker |
| 5,517,073 A | 5/1996 | Ohkuma |
| 5,524,637 A | 6/1996 | Erickson |
| 5,526,290 A | 6/1996 | Kanzaki |
| 5,539,706 A | 7/1996 | Takenaka et al. |
| 5,541,860 A | 7/1996 | Takei et al. |
| 5,541,976 A | 7/1996 | Ghisler |
| 5,566,477 A | 10/1996 | Mathis et al. |
| 5,583,776 A | 12/1996 | Levi et al. |
| 5,596,821 A | 1/1997 | Solo |
| 5,606,728 A | 2/1997 | Keba et al. |
| 5,608,412 A | 3/1997 | Welles et al. |
| 5,623,944 A | 4/1997 | Nashner |
| 5,625,882 A | 4/1997 | Vook et al. |
| 5,631,421 A | 5/1997 | Ohgke et al. |
| 5,636,146 A | 6/1997 | Flentov et al. |
| 5,664,346 A | 9/1997 | Barker |
| 5,668,694 A | 9/1997 | Sato et al. |
| 5,668,880 A | 9/1997 | Alajajian |
| 5,673,501 A | 10/1997 | Mathews |
| 5,720,200 A | 2/1998 | Anderson et al. |
| 5,724,265 A | 3/1998 | Hutchings |
| 5,728,032 A | 3/1998 | Glass |
| 5,729,590 A | 3/1998 | Dimitriadis et al. |
| 5,775,011 A | 7/1998 | Reitano, Jr. |
| 5,838,226 A | 11/1998 | Houggy et al. |
| D403,532 S | 1/1999 | Moser |
| 5,891,042 A | 4/1999 | Sham et al. |
| 5,897,457 A | 4/1999 | Mackovjak |
| 5,899,963 A | 5/1999 | Hutchings |
| 5,906,004 A | 5/1999 | Lebby et al. |
| 5,925,001 A | 7/1999 | Hoyt et al. |
| 5,930,920 A | 8/1999 | Arnold |
| 5,955,667 A | 9/1999 | Fyfe |
| 5,963,891 A | 10/1999 | Walker et al. |
| 5,976,083 A | 11/1999 | Richardson et al. |
| 5,987,018 A | 11/1999 | Freeburg et al. |
| 5,989,200 A | 11/1999 | Yoshimura et al. |
| 6,018,705 A | 1/2000 | Gaudet et al. |
| 6,032,108 A | 2/2000 | Seiple et al. |
| 6,038,935 A | 3/2000 | Fullen et al. |
| 6,042,549 A | 3/2000 | Amano et al. |
| 6,052,654 A | 4/2000 | Gaudet et al. |
| 6,080,690 A | 6/2000 | Lebby et al. |
| 6,094,844 A | 8/2000 | Potts |
| 6,122,340 A | 9/2000 | Darley et al. |
| 6,135,951 A | 10/2000 | Richardson et al. |
| 6,145,551 A | 11/2000 | Jayaraman et al. |
| 6,154,642 A | 11/2000 | Dumont et al. |
| 6,169,905 B1 | 1/2001 | Fukuda |
| 6,175,608 B1 | 1/2001 | Pyles et al. |
| 6,210,771 B1 | 4/2001 | Post et al. |
| 6,236,674 B1 | 5/2001 | Morelli et al. |
| 6,305,221 B1 | 10/2001 | Hutchings |
| 6,315,009 B1 | 11/2001 | Jayaraman et al. |
| 6,356,856 B1 | 3/2002 | Damen et al. |
| 6,357,147 B1 | 3/2002 | Darley et al. |
| 6,493,652 B1 * | 12/2002 | Ohlenbusch et al. ........ 702/160 |
| 6,536,139 B2 | 3/2003 | Darley et al. |
| 6,650,629 B1 | 11/2003 | Takahashi et al. |
| 6,771,213 B2 | 8/2004 | Durst et al. |
| 2003/0000053 A1 | 1/2003 | Rooney et al. |
| 2004/0009731 A1 | 1/2004 | Rabinowicz |

\* cited by examiner

STEP LENGTH (L$_s$)= 
T$_C$ • SPEED

| | DISTANCE | RACE TIME | SPLIT TIME | AVERAGE SPEED | AVERAGE SPEED | AVERAGE STRIDE LENGTH | AVERAGE STRIDE LENGTH | AVERAGE STRIDE LENGTH | AVERAGE STRIDE RATE | AVERAGE BURN RATE | TOTAL CALORIES | ACCELERATION |
|---|---|---|---|---|---|---|---|---|---|---|---|---|
| | METERS | SECONDS | SECONDS | METERS/SECOND | MPH | METERS | FEET | INCHES | STEPS/MINUTE | CALORIES/MINUTE | CALORIES | METERS/SECOND |
| SPLITS | 0 | 0 | 0 | 0 | 0 | 0 | 0 | 0 | 0 | 0 | 0 | 0 |
| | 50 | 5.6 | 5.6 | 9.0 | 20.1 | 2.22 | 7 | 3 | 249.5 | 41.1 | 3.7 | 1.621 |
| | 100 | 10.4 | 4.9 | 10.3 | 22.9 | 2.39 | 7 | 9 | 257.9 | 44.2 | 7.3 | 0.257 |
| | 150 | 15.4 | 4.9 | 10.1 | 22.6 | 2.37 | 7 | 9 | 256.1 | 43.9 | 10.9 | -0.030 |
| | 200 | 20.6 | 5.2 | 9.6 | 21.4 | 2.22 | 7 | 3 | 259.7 | 42.3 | 14.6 | -0.100 |
| | 250 | 26.0 | 5.4 | 9.2 | 20.7 | 2.18 | 7 | 1 | 255.1 | 41.3 | 18.3 | -0.063 |
| | 300 | 31.6 | 5.6 | 8.9 | 20.0 | 2.15 | 7 | 0 | 250.4 | 40.5 | 22.1 | -0.054 |
| | 350 | 37.4 | 5.8 | 8.7 | 19.4 | 2.20 | 7 | 2 | 236.1 | 39.6 | 25.9 | -0.048 |
| | 400 | 43.9 | 6.5 | 7.6 | 17.1 | 2.18 | 7 | 1 | 211.1 | 36.5 | 29.9 | -0.155 |

Fig. 37

| SPEED (MPH) | PACE (SECONDS/MILE) | Tc (ms) | Ts (ms) | AVERAGE GROUND FORCE (LBS) | STEPS PER MILE | STRESS PER 1/10 MILE (LBS) | STEPS PER MINUTE | STRESS PER MINUTE (LBS) |
|---|---|---|---|---|---|---|---|---|
| 5 | 720 | 302 | 730 | 181 | 986 | 17881 | 82 | 14901 |
| 6 | 600 | 270 | 702 | 195 | 855 | 16667 | 85 | 16667 |
| 7 | 514 | 254 | 676 | 200 | 760 | 15177 | 89 | 17777 |
| 8 | 450 | 234 | 652 | 209 | 690 | 14423 | 92 | 19231 |
| 9 | 400 | 214 | 638 | 224 | 627 | 14019 | 94 | 21028 |
| 10 | 360 | 204 | 618 | 227 | 583 | 13235 | 97 | 22059 |
| 11 | 327 | 190 | 600 | 237 | 545 | 12908 | 100 | 23684 |

Fig. 40

MONITORING ACTIVITY OF A USER IN LOCOMOTION ON FOOT

RELATED APPLICATIONS

This is a continuation of application Ser. No. 11/098,788, filed Apr. 4, 2005, which is a continuation of application Ser. No. 09/643,191, filed on Aug. 21, 2000, and now U.S. Pat. No. 6,898,550, which is a continuation-in-part of each of application Ser. Nos. 09/547,975, 09/547,976, 09/547,977, and 09/548,217, each of which was filed on Apr. 12, 2000, and is now abandoned. Each of application Ser. Nos. 09/547,975, 09/547,976, 09/547,977, and 09/548,217 is a continuation-in-part of application Ser. No. 09/364,559, filed on Jul. 30, 1999, and now U.S. Pat. No. 6,052,654, which is a continuation of application Ser. No. 08/942,802, filed Oct. 2, 1997, and now U.S. Pat. No. 6,018,705. Application Ser. No. 09/643,191 is also a continuation-in-part of each of application Ser. Nos. 09/164,654, filed Oct. 1, 1998, and now U.S. Pat. No. 6,122,340, Ser. No. 09/382,049, filed Aug. 24, 1999, and now U.S. Pat. No. 6,336,365, and Ser. No. 09/521,073, filed Mar. 7, 2000, and now U.S. Pat. No. 6,560,903. Priority is claimed to each of the foregoing applications under 35 U.S.C. §120, and the entire contents of each of them is hereby incorporated herein by reference.

BACKGROUND OF THE INVENTION

1. Field of the Invention

The present invention relates to the monitoring of the activity of a user in locomotion on foot.

2. Discussion of the Related Art

It is known that useful information may be derived from the measurement of the "foot contact time" (Tc) of a user in locomotion, wherein "foot contact time" refers to the period of time that a foot of a user is in contact with the surface during a stride taken by the user while the user is in locomotion on foot. Once the foot contact time (Tc) of the user is known, other information, such as rate of travel, distance traveled, and ambulatory expended energy may be calculated based upon this measured foot contact time (Tc).

In the past, foot contact time (Tc) has been measured by placing pressure-sensitive sensors or switches, such as resistive sensors, in both the heel and toe portions of the sole of a shoe, and measuring a time difference between a first signal output by the heel sensor (which indicates that the foot has made physical contact with the surface) and a second signal output by the toe sensor (which indicates that the foot has left the surface). These sensors, however, are subjected to a high-impact environment inside of the shoe, and therefore fail frequently. In addition, inaccurate foot contact time (Tc) measurements may result when a user is taking strides during which either the heel sensor or the toe sensor is not activated, for example, when a user is running on his or her toes.

Another device well-known in the art is a pedometer. A pedometer typically is mounted on the waist of a user and is configured to count the footsteps of the user by measuring the number of times the user's body moves up an down during strides taken by the user. A well-known prior art pedometer design uses a weight mounted on a spring to count the number of times that the user's body moves up and down as the user is walking. By properly calibrating the pedometer according to a previously measured stride length of the user, the distance traveled by the user may be measured by this device. These "weight-on-a-spring" pedometers, however, generally cannot measure the distance traveled by a runner because the weight experiences excessive bouncing during running and footsteps are often "double-counted" because of this bouncing, thereby causing the pedometer to produce inaccurate results. These devices therefore cannot be used across different training regimes (e.g., walking, jogging, and running).

Another prior art pedometer device uses an accelerometer to measure the number of times that a user's foot impacts the surface when the user is in locomotion. That is, an accelerometer is mounted on the user's shoe so as to produce a signal having pronounced downward going peaks that are indicative of moments that the user's foot impacts the surface. These devices therefore produce results similar to the prior art weight-on-a-spring pedometer devices in that they merely count the number of footsteps of the user, and must be calibrated according to the stride length of the user in order to calculate the distance traveled by the user. Thus, these accelerometer-based devices are subject to similar limitations as are the weight-on-a-spring devices, and are not capable of measuring the foot contact time (Tc) of a user in locomotion.

It is therefore a general object of the present invention to provide a new approach to pedometry.

SUMMARY OF THE INVENTION

According to one aspect of the present invention, a method comprises steps of identifying a grade of the surface with at least one device supported by the user while the user is in locomotion on foot on a surface, and determining a performance parameter of the user with the at least one device based upon the identified grade of the surface.

According to another aspect of the invention, a method comprises a step of identifying a grade of a surface based upon a measured physiological parameter of a user in locomotion on foot on the surface.

According to another aspect of the invention, a method comprises steps of identifying an average foot contact time of a user during a first outing, identifying an average pace of the user during the first outing, and determining a relationship between foot contact times of the user and corresponding paces of the user, wherein the relationship is based upon the average foot contact time and the average pace identified during the first outing, and wherein no other average foot contact times and no other average paces identified during any different outings by the user are used to define the relationship. The method further comprises steps of determining at least one foot contact time of the user during a second outing, and calculating a pace of the user during the second outing based upon the determined at least one foot contact time and the determined relationship between foot contact times of the user and corresponding paces of the user.

According to another aspect of the invention, a method comprises steps of determining a single user-specific calibration constant that defines a relationship between foot contact times of a user and corresponding paces of the user, wherein no other user-specific calibration constants are used to define the relationship, determining at least one foot contact time of the user during an outing, and calculating a pace of the user during the outing based upon the determined at least one foot contact time and the relationship between foot contact times of the user and corresponding paces of the user that is defined by the single user-specific calibration constant.

According to another aspect of the invention, an apparatus comprises a mount, a housing, and a sensor. The mount is adapted to be disposed at least partially underneath a shoelace of a shoe. The housing is configured and arranged to be placed in at least first and second states in relation to the mount, wherein in the first state the housing is movable with respect to the mount and in the second state the housing is immovable with respect to the mount. There is a tongue on one of the mount and the housing and a groove on the other of the mount and the housing, the tongue being adapted to engage the groove when the housing is in the second state in relation to the mount and to disengage the groove then the housing is in the first state with respect to the mount. The sensor, which senses motion of the shoe, is disposed within the housing such that the sensor remains disposed within the housing when the housing is placed in the first state in relation to the mount and the housing is moved with respect to the mount.

According to another aspect of the invention, a method involves providing a housing that houses a sensor that senses motion of a shoe, and attaching the mount to an instep portion of the shoe such that at least a portion of the mount is disposed underneath at least a portion of a shoelace of the shoe. A tongue on one of the mount and the housing is engaged with a groove on the other of the mount and the housing to inhibit the housing from moving with respect to the mount. The tongue is also disengaged from the groove, and the housing is moved with respect to the mount without separating the sensor from the housing.

According to another aspect of the invention, a method involves determining at least one calculated parameter based upon at least one determined performance parameter of the user and at least one determined variable physiological parameter of the user.

According to another aspect of the invention, a method involves identifying at least one of an existence of a non-zero grade of a surface and a value of the grade of the surface based upon at least one determined variable physiological parameter of a user.

According to another aspect of the invention, a method involves identifying at least one of an existence of a grade of a surface and a value of the grade of the surface based upon at least one determined performance parameter of a user.

According to another aspect of the invention, a system includes at least one processor configured to identify at least one of an existence of a non-zero grade of a surface and a value of the grade of the surface based upon at least one determined variable physiological parameter of a user in locomotion on foot on the surface.

According to another aspect of the invention, a system includes at least one processor configured to identify at least one of an existence of a non-zero grade of a surface and a value of the grade of the surface based upon at least one determined performance parameter of the user in locomotion on foot on the surface.

According to another aspect of the invention, a system includes at least one first sensor that determines at least one performance parameter of the user while the user is in locomotion on foot; at least one second sensor that determines at least one variable physiological parameter of the user while the user is in locomotion on foot; and means for determining at least one calculated parameter based upon the at least one determined performance parameter of the user and the at least one determined variable physiological parameter of the user.

According to another aspect of the invention, a system includes at least one sensor that determines at least one physiological condition of a user while the user is in locomotion on foot on a surface; and means for identifying at least one of an existence of a non-zero grade of the surface and a value of the grade of the surface based upon the at least one determined physiological condition of the user.

According to another aspect of the invention, a system includes at least one sensor that determines at least one performance parameter of a user while the user is in locomotion on foot on a surface; and means for identifying at least one of an existence of a non-zero grade of the surface and a value of the grade of the surface based upon the at least one determined performance parameter.

According to another aspect of the invention, a method includes steps of: with at least one device supported by a user while the user is in locomotion on foot, determining at least one performance parameter of the user; and estimating a value of a variable physiological parameter of the user based upon the determined at least one performance parameter of the user.

According to another aspect of the invention, a method includes steps of: (a) identifying at least one of an existence of a non-zero grade of a surface and a value of the grade of the surface; and (b) with at least one device supported by a user while the user is in locomotion on foot, determining at least one performance parameter of the user based upon the identified at least one of an existence of the non-zero grade of the surface and the value of the grade of the surface.

According to another aspect of the invention, a method includes steps of: (a) determining at least one altitude of a user; and (b) with at least one device supported by the user while the user is in locomotion on foot, calculating at least one performance parameter of the user based upon the at least one determined altitude of the user.

According to another aspect of the invention, a system includes at least one sensor, adapted to be supported by a user while the user is in locomotion on foot, that determines at least one performance parameter of the user; and at least one processor that calculates a value of a variable physiological parameter of the user based upon the determined at least one performance parameter of the user.

According to another aspect of the invention, a system includes at least one processor, adapted to be supported by a user while the user is in locomotion on foot on a surface, that determines at least one performance parameter of the user based upon at least one of an identified existence of a non-zero grade of the surface and an identified value of the grade of the surface.

According to another aspect of the invention, a system includes at least one processor, adapted to be supported by a user while the user is in locomotion on foot, that calculates at least one performance parameter of the user based upon at least one identified altitude of the user.

According to another aspect of the invention, a system includes at least one sensor, adapted to be supported by a user while the user is in locomotion on foot, that determines at least one performance parameter of the user; and means for calculating a value of a variable physiological parameter of the user based upon the determined at least one performance parameter.

According to another aspect of the invention, a system includes means for identifying at least one of an existence of a non-zero grade of a surface and a value of the grade of the surface; and means, adapted to supported by a user while the user is in locomotion on foot on the surface, for determining at least one performance parameter of the user based upon the identified at least one of the existence of the non-zero grade of the surface and the value of the grade of the surface.

According to another aspect of the invention, a system includes means for determining at least one altitude of a user; and means, adapted to be supported by the user while the user is in locomotion on foot, for calculating at least one performance parameter of the user based upon the at least one determined altitude of the user.

According to another aspect of the invention, a method involves, in response to movement of a user during at least one footstep taken by the user, generating a signal that experiences changes during a time period that the foot is airborne during at least one footstep taken by the user. At least one change in the signal generated after the foot has become airborne and before the foot contacts the surface is identified that is indicative of the foot being airborne during the at least one footstep.

According to another aspect of the invention, a method involves generating a signal in response to movement of a user during at least one footstep taken by the user. The signal is monitored to determine when the signal has experienced a minimum degree of smoothness for at least a given period of time. In response to determining that the signal has experienced the minimum degree of smoothness for at least the given period of time, it is identified that the foot of the user is airborne.

According to another aspect of the invention, a method involves generating a signal in response to movement of a user during at least one footstep taken by the user. It is determined whether any characteristics of the signal satisfy any one of a plurality of predetermined criteria consistent with a foot of the user engaging in a particular event during a footstep.

According to another aspect of the invention, a method involves generating a signal in response to movement of a user during at least one footstep taken by the user. The signal is sampled to obtain a plurality of samples of the signal. Differences between pairs of the plurality of samples of the signal are calculated, and the calculated differences between the pairs of the plurality of samples of the signal are monitored to identify at least one pair of the plurality of samples of the signal having a difference therebetween that is indicative of a particular event during the at least one footstep.

According to another aspect of the invention, a method involves generating a signal in response to movement of a user during a plurality of footsteps taken by the user. A threshold is set based upon at least one first characteristic of the signal generated during at least a first one of the plurality of footsteps preceding a second one of the plurality of footsteps. The signal generated during the second one of the plurality of footsteps is analyzed to determine whether at least one second characteristic of the signal generated during the second one of the plurality of footsteps has exceeded the threshold.

According to another aspect of the invention, a method includes steps of: (a) generating a signal in response to movement of a user during a plurality of footsteps taken by the user; (b) with at least one processor, analyzing the signal to determine a moment that a foot of the user makes contact with a surface during one of the plurality of footsteps taken by the user; (c) after performing the step (b), with the at least one processor, analyzing the signal to determine a moment that the foot leaves the surface during the one of the plurality of footsteps; (d) waiting a given period of time after performing the step (b) to perform the step (c); (e) with the at least one processor, during the given period of time, performing calculations involving at least one of a determined foot contact time and a determined foot loft time; and (f) repeating the steps (b), (c), (d), and (e) for each of the plurality of footsteps.

According to another aspect of the invention, a system is disclosed that may be used in conjunction with at least one sensor that, in response to movement of a user during at least one footstep taken by the user on a surface, generates a signal that experiences changes during a time period that a foot of the user is airborne during the at least one footstep. The system includes at least one processor configured to identify at least one change in the signal generated after the foot has become airborne and before the foot contacts the surface that is indicative of the foot being airborne during the at least one footstep.

According to another aspect of the invention, a system is disclosed that may be used in conjunction with at least one sensor that generates a signal in response to movement of a user during at least one footstep taken by the user. The system includes at least one processor configured to monitor the signal to determine when the signal has experienced a minimum degree of smoothness for at least a given period of time, and to, in response to determining that the signal has experienced the minimum degree of smoothness for at least the given period of time, identify that the foot of the user is airborne.

According to another aspect of the invention, a system is disclosed that may be used in conjunction with at least one sensor that generates a signal in response to movement of a user during at least one footstep taken by the user on a surface. The system includes at least one processor configured to determine whether any characteristics of the signal satisfy any one of a plurality of predetermined criteria consistent with a foot of the user engaging in a particular event during a footstep.

According to another aspect of the invention, a system is disclosed that may be used in conjunction with at least one sensor that generates a signal in response to movement of a user during at least one footstep taken by the user on a surface. The system includes at least one processor configured to sample the signal to obtain a plurality of samples of the signal, to calculate differences between pairs of the plurality of samples of the signal, and to monitor the calculated differences between the pairs of the plurality of samples of the signal to identify at least one pair of the plurality of samples of the signal having a difference therebetween that is indicative of a particular event during the at least one footstep.

According to another aspect of the invention, a system is disclosed that may be used in conjunction with at least one sensor that generates a signal in response to movement of a user during a plurality of footsteps taken by the user. The system includes at least one processor configured to set a threshold based upon at least one first characteristic of the signal generated during at least a first one of the plurality of footsteps preceding a second one of the plurality of footsteps, and to analyze the signal generated during the second one of the plurality of footsteps to determine whether at least one second characteristic of the signal generated during the second one of the plurality of footsteps has exceeded the threshold.

According to another aspect of the invention, a system includes at least one processor configured to compare a foot contact time of a user with a threshold value, to determine that the user is running if the foot contact time is less than the threshold value, and to determine that the user is walking if the foot contact time is greater than the threshold value.

According to another aspect of the invention, a system includes at least one sensor that, in response to movement of a user during at least one footstep taken by the user, generates a signal that experiences changes during a time period that the foot is airborne during the at least one footstep, and means for identifying at least one change in the signal generated after the foot has become airborne and before the foot contacts a surface that is indicative of the foot being airborne during the at least one footstep.

According to another aspect of the invention, a system includes at least one sensor that generates a signal in response to movement of a user during at least one footstep taken by the user, and means for monitoring the signal to determine when the signal has experienced a minimum degree of smoothness for at least a given period of time, and for, in response to determining that the signal has experienced the minimum degree of smoothness for at least the given period of time, identifying that the foot of the user is airborne.

According to another aspect of the invention, a system includes at least one sensor that generates a signal in response to movement of a user during at least one footstep taken by the user, and means for determining whether any characteristics of the signal satisfy any one of a plurality of predetermined criteria consistent with a foot of the user engaging in a particular event during a footstep.

According to another aspect of the invention, a system includes at least one sensor that generates a signal in response to movement of a user during at least one footstep taken by the user, and means for sampling the signal to obtain a plurality of samples of the signal, for calculating differences between pairs of the plurality of samples of the signal, and for monitoring the calculated differences between the pairs of the plurality of samples of the signal to identify at least one pair of the plurality of samples of the signal having a difference therebetween that is indicative of a particular event during the at least one footstep.

According to another aspect of the invention, a system includes at least one sensor that generates a signal in response to movement of a user during a plurality of footsteps taken by the user, and means for setting a threshold based upon at least one first characteristic of the signal generated during at least a first one of the plurality of footsteps preceding a second one of the plurality of footsteps, and for analyzing the signal generated during the second one of the plurality of footsteps to determine whether at least one second characteristic of the signal generated during the second one of the plurality of footsteps has exceeded the threshold.

According to another aspect of the invention, a method includes steps of (a) generating a signal in response to movement of a user during a footstep taken by the user; (b) identifying a first characteristic in the signal consistent with the occurrence of a toe-off event; (c) identifying a first moment that the first characteristic occurred as a potential occurrence of a toe-off event during the footstep; (d) identifying a second characteristic in the signal, occurring after the first characteristic in the signal, consistent with the occurrence of a toe-off event; and (e) identifying a second moment that the second characteristic occurred as the potential occurrence of the toe-off event during the footstep.

According to another aspect of the invention, a system includes at least one sensor that generates a signal in response to movement of a user during a footstep taken by the user, and at least one processor that identifies a first characteristic in the signal consistent with the occurrence of a toe-off event, that identifies a first moment that the first characteristic occurred as a potential occurrence of a toe-off event during the footstep, that identifies a second characteristic in the signal, occurring after the first characteristic in the signal, consistent with the occurrence of a toe-off event, and that identifies a second moment that the second characteristic occurred as the potential occurrence of the toe-off event during the footstep.

According to another aspect of the invention, a system includes at least one sensor that generates a signal in response to movement of a user during a footstep taken by the user; means for identifying a first characteristic in the signal consistent with the occurrence of a toe-off event; means for identifying a first moment that the first characteristic occurred as a potential occurrence of a toe-off event during the footstep; means for identifying a second characteristic in the signal, occurring after the first characteristic in the signal, consistent with the occurrence of a toe-off event; and means for identifying a second moment that the second characteristic occurred as the potential occurrence of the toe-off event during the footstep.

According to another aspect of the invention, a display unit to be mounted on a wrist of a user includes a display screen, a base, and at least one strap. The display screen visually displays characters, and has a top edge and a bottom edge corresponding, respectively, to tops and bottoms of the characters displayed on the display screen. The base supports the display screen and houses electronic circuitry associated with the display screen. The at least one strap is attached to the base and is adapted to secure the base to the wrist of the user. The base is configured and arranged such that, when the base is secured to the wrist of the user with the at least one strap, the top edge of the display screen is disposed a first distance away from an outer surface of the user's wrist as determined along a first line oriented normal to the outer surface of the user's wrist and passing through the top edge of the display screen, and the bottom edge of the display screen is disposed a second distance away from an outer surface of the user's wrist as determined along a second line oriented normal to the outer surface of the user's wrist and passing through the bottom edge of the display screen, wherein the first distance is greater than the second distance.

According to another aspect of the invention, a method includes steps of: (a) with at least one device supported by a user while the user is in locomotion on foot, determining respective values of at least first and second parameters selected from a group consisting of: an instantaneous pace of the user, an average pace of the user, and a distance traveled by the user; and (b) displaying visually-perceptible information indicative of the determined values of the at least first and second parameters, simultaneously.

According to another aspect of the invention, a method includes steps of: (a) with at least one device supported by a user while the user is in locomotion on foot, determining a value of at least one variable physiological parameter of the user; (b) with the at least one device, determining a value of at least one performance parameter of the user; and (c) displaying visually-perceptible information indicative of the determined values of the at least one variable physiological parameter of the user and the at least one performance parameter of the user, simultaneously.

According to another aspect of the invention, a method includes steps of: (a) with at least one device supported by the user, determining respective values of at least first and second parameters selected from a group consisting of: an instantaneous speed of the user, an average speed of the user, and a distance traveled by the user; and (b) displaying visually-perceptible information indicative of the determined values of the at least first and second parameters, simultaneously.

According to another aspect of the invention, a system includes at least one device adapted to be supported by a user while the user is in locomotion on foot. The at least one device includes at least one sensor to determine respective values of at least first and second parameters selected from a group consisting of: an instantaneous pace of the user, an average pace of the user, and a distance traveled by the user, the at least one device further comprising a display configured to display visually-perceptible information indicative of the determined values of the at least first and second parameters, simultaneously.

According to another aspect of the invention, a system includes at least one device adapted to be supported by a user while the user is in locomotion on foot. The at least one device includes a first sensor to determine a value of at least one variable physiological parameter of the user, a second sensor to determine a value of at least one performance parameter of the user, and a display configured to display visually-perceptible information indicative of the determined values of the at least one variable physiological parameter of the user and the at least one performance parameter of the user, simultaneously.

According to another aspect of the invention, a system includes at least one device adapted to be supported by a user while the user is in locomotion on foot. The at least one device includes at least one sensor to determine respective values of at least first and second parameters selected from a group consisting of: an instantaneous speed of the user, an average speed of the user, and a distance traveled by the user, and a display configured to display visually-perceptible information indicative of the determined values of the at least first and second parameters, simultaneously.

According to another aspect of the invention, a system includes means, adapted to be supported by a user while the user is in locomotion on foot, for determining respective values of at least first and second parameters selected from a group consisting of: an instantaneous pace of the user, an average pace of the user, and a distance traveled by the user; and means, adapted to be supported by the user while the user is in locomotion on foot, for displaying visually-perceptible information indicative of the determined values of the at least first and second parameters, simultaneously.

According to another aspect of the invention, a system includes first means, adapted to be supported by a user while the user is in locomotion on foot, for determining a value of at least one variable physiological parameter of a user; second means, adapted to be supported by the user while the user is in locomotion on foot, for determining a value of at least one performance parameter of the user; and third means, adapted to be supported by the user while the user is in locomotion on foot, for displaying visually-perceptible information indicative of the determined values of the at least one variable physiological parameter of the user and the at least one performance parameter of the user, simultaneously.

According to another aspect of the invention, a system includes means, adapted to be supported by a user while the user is in locomotion on foot, for determining respective values of at least first and second parameters selected from a group consisting of: an instantaneous speed of the user, an average speed of the user, and a distance traveled by the user; and means, adapted to be supported by the user while the user is in locomotion on foot, for displaying visually-perceptible information indicative of the determined values of the at least first and second parameters, simultaneously.

According to another aspect of the invention, a method includes steps of: (a) identifying an average foot contact time of a user during a first outing; (b) identifying an average pace of the user during the first outing; (c) defining a relationship between foot contact times of the user and corresponding paces of the user, wherein the relationship is based upon the average foot contact time and the average pace identified during the first outing, and wherein no other average foot contact times and no other average paces identified during any different outings by the user are used to define the relationship; and (d) calibrating at least one device that monitors activity of the user in locomotion on foot based upon the defined relationship between foot contact times of the user and corresponding paces of the user.

According to another aspect of the invention, a method includes steps of: (a) determining a single user-specific calibration constant that defines a relationship between foot contact times of a user and corresponding paces of the user, wherein no other user-specific calibration constants are used to define the relationship; and (b) calibrating at least one device that monitors activity of the user in locomotion on foot based upon the relationship between foot contact times of the user and corresponding paces of the user that is defined by the single user-specific calibration constant.

According to another aspect of the invention, a method includes steps of: (a) on a graph having foot contact times of a user on a first coordinate axis and paces of the user on a second coordinate axis, determining a location of a first point particular to the user; (b) identifying a second point on the graph independent of the user; (c) based upon locations of the first and second points on the graph, defining a curve on the graph that intercepts both of the first and second points; and (d) calibrating at least one device that monitors activity of the user in locomotion on foot based upon the defined curve.

According to another aspect of the invention, a method includes steps of: (a) based upon a first relationship between foot contact times of a user and corresponding paces of the user, defining a second relationship between inverse values of foot contact times of the user and corresponding speeds of the user; and (b) calibrating at least one device that monitors activity of the user in locomotion on foot based upon the second relationship.

According to another aspect of the invention, a method involves determining a speed of a user in locomotion on foot by including at least one determined foot contact time in an equation defining a relationship between inverse values of foot contact times of the user and corresponding speeds of the user.

According to another aspect of the invention, a method includes steps of: (a) based upon a first relationship between inverse values of foot contact times of a user and corresponding speeds of the user, defining a second relationship between foot contact times of the user and corresponding paces of the user; and (b) calibrating at least one device that monitors activity of the user in locomotion on foot based upon the second relationship.

According to another aspect of the invention, a method includes steps of: (a) identifying an average foot contact time of a user during a first outing; (b) identifying an average speed of the user during the first outing; (c) defining a relationship between inverse values of foot contact times of the user and corresponding speeds of the user, wherein the relationship is based upon the average foot contact time and the average speed identified during the first outing; and (d) calibrating at least one device that monitors activity of the user in locomotion on foot based upon the defined relationship between inverse values of foot contact times of the user and corresponding speeds of the user.

According to another aspect of the invention, a method includes steps of: (a) determining a single user-specific calibration constant that defines a relationship between inverse values of foot contact times of a user and corresponding speeds of the user, wherein no other user-specific calibration constants are used to define the relationship; and (b) calibrating at least one device that monitors activity of the user in locomotion on foot based upon the relationship between inverse values of foot contact times of the user and corresponding speeds of the user that is defined by the single user-specific calibration constant.

According to another aspect of the invention, a system includes at least one processor configured to define a relationship between foot contact times of a user and corresponding paces of the user, wherein the relationship is based upon an average foot contact time and an average pace identified during a first outing, and wherein no other average foot contact times and no other average paces identified during any different outings by the user are used to define the relationship, the at least one processor being further configured to calculate at least one of a pace of the user and a distance traveled by the user during a second outing based upon at least one foot contact time determined during the second outing and the defined relationship between foot contact times of the user and corresponding paces of the user.

According to another aspect of the invention, a system includes at least one processor configured to use a single user-specific calibration constant to define a relationship between foot contact times of a user and corresponding paces of the user without any other user-specific calibration constants being used to define the relationship, the at least one processor being further configured to calculate at least one of a pace of the user and a distance traveled by the user during an outing based upon at least one foot contact time determined during the outing and the defined relationship between foot contact times of the user and corresponding paces of the user.

According to another aspect of the invention, a system includes at least one processor configured to, on a graph having foot contact times of a user on a first coordinate axis and paces of the user on a second coordinate axis, determine a location of a first point particular to the user, to identify a second point on the graph independent of the user, and to, based upon locations of the first and second points on the graph, define a curve on the graph that intercepts both of the first and second points, the at least one processor being further configured to calculate at least one of a pace of the user and a distance traveled by the user during an outing based upon at least one foot contact time determined during the outing and the defined curve.

According to another aspect of the invention, a system includes at least one processor configured to, based upon a first relationship between foot contact times of a user and corresponding paces of the user, define a second relationship between inverse values of foot contact times of the user and corresponding speeds of the user, the at least one processor being further configured to calculate at least one of a speed of the user and a distance traveled by the user during an outing based upon at least one foot contact time determined during the outing and the second relation ship.

According to another aspect of the invention, a system includes at least one processor configured to, determine a speed of a user in locomotion on foot by including at least one determined foot contact time in an equation defining a relationship between inverse values of foot contact times of the user and corresponding speeds of the user.

According to another aspect of the invention, a system includes at least one processor configured to, based upon a first relationship between inverse values of foot contact times of a user and corresponding speeds of the user, define a second relationship between foot contact times of the user and corresponding paces of the user, the at least one processor being further configured to calculate at least one of a speed of the user and a distance traveled by the user during an outing based upon at least one foot contact time determined during the outing and the second relationship.

According to another aspect of the invention, a system includes at least one processor configured to define a relationship between inverse values of foot contact times of a user and corresponding speeds of the user based upon an average foot contact time and an average speed determined during a first outing, the at least one processor being further configured to calculate at least one of a speed of the user and a distance traveled by the user during a second outing based upon at least one foot contact time determined during the second outing and the defined relationship.

According to another aspect of the invention, a system includes at least one processor configured to use a single user-specific calibration constant to define a relationship between inverse values of foot contact times of a user and corresponding speeds of the user without using any other user-specific calibration constants to define the relationship, the at least one processor being further configured to calculate at least one of a speed of the user and a distance traveled by the user during an outing based upon at least one foot contact time determined during the outing and the relationship between inverse values of foot contact times of the user and corresponding speeds of the user that is defined by the single user-specific calibration constant.

According to another aspect of the invention, a system includes means for defining a relationship between foot contact times of the user and corresponding paces of the user, wherein the relationship is based upon an average foot contact time and an average pace identified during a first outing, and wherein no other average foot contact times and no other average paces identified during any different outings by the user are used to define the relationship; and means for calculating at least one of a pace of the user and a distance traveled by the user during a second outing based upon at least one foot contact time determined during the second outing and the defined relationship between foot contact times of the user and corresponding paces of the user.

According to another aspect of the invention, a system includes means for using a single user-specific calibration constant to define a relationship between foot contact times of a user and corresponding paces of the user, wherein no other user-specific calibration constants are used to define the relationship; and means for calculating at least one of a pace of the user and a distance traveled by the user during an outing based upon at least one foot contact time determined during the outing and the defined relationship between foot contact times of the user and corresponding paces of the user.

According to another aspect of the invention, a system includes means for, based upon a first relationship between foot contact times of a user and corresponding paces of the user, defining a second relationship between inverse values of foot contact times of the user and corresponding speeds of the user; and means for calculating at least one of a speed of the user and a distance traveled by the user during an outing based upon at least one foot contact time determined during the outing and the second relationship.

According to another aspect of the invention, a system includes means for determining at least on foot contact time of a user; and means for determining a speed of the user by including the at least one foot contact time in an equation defining a relationship between inverse values of foot contact times of the user and corresponding speeds of the user.

According to another aspect of the invention, a system includes means for, based upon a first relationship between inverse values of foot contact times of a user and corresponding speeds of the user, defining a second relationship between foot contact times of the user and corresponding paces of the user; and means for calculating at least one of a pace of the user and a distance traveled by the user during an outing based upon at least one foot contact time determined during the outing and the second relationship.

According to another aspect of the invention, a system includes means for defining a relationship between inverse values of foot contact times of the user and corresponding speeds of the user, wherein the relationship is based upon an average foot contact time and an average speed identified during a first outing; and means for calculating at least one of a speed of the user and a distance traveled by the user during a second outing based upon at least one foot contact time determined during the second outing and the relationship between inverse values of foot contact times of the user and corresponding speeds of the user.

According to another aspect of the invention, a system includes means for using a single user-specific calibration constant to define a relationship between inverse values of foot contact times of a user and corresponding speeds of the user, wherein no other user-specific calibration constants are used to define the relationship; and means for calculating at least one of a speed of the user and a distance traveled by the user during an outing based upon at least one foot contact time determined during the outing and the relationship between inverse values of foot contact times of the user and corresponding speeds of the user that is defined by the single user-specific calibration constant.

According to another aspect of the invention, a method includes steps of: (a) with at least one device supported by a user while the user is in locomotion on foot, determining at least one foot contact time of the user in locomotion; (b) comparing a variable having the at least one determined foot contact time as a factor therein with a threshold value; and (c1) if the variable is one of greater than or less than the threshold value, determining that the user is walking; and (c2) if the variable is the other of greater than or less than the threshold value, determining that the user is running.

According to another aspect of the invention, a method includes steps of: (a) determining at least one foot contact time of a user while the user is in locomotion on foot; (b) comparing the at least one determined foot contact time with a threshold value; and (c1) if the foot contact time is less than the threshold value, determining that the user is running; and (c2) if the foot contact time is greater than the threshold value, determining that the user is walking.

According to another aspect of the invention, a system includes at least one processor, adapted to be supported by a user while the user is in locomotion on foot, that determines at least one foot contact time of the user, and compares a variable having the at least one determined foot contact time as a factor therein with a threshold value; wherein, if the variable is one of greater than or less than the threshold value, the at least one processor determines that the user is walking, and, if the variable is the other of greater than or less than the threshold value, the at least one processor determines that the user is running.

According to another aspect of the invention, a system includes at least one processor, adapted to be supported by a user while the user is in locomotion on foot, that determines at least one foot contact time of the user, and compares the at least one determined foot contact time with a threshold value; wherein, if the foot contact time is less than the threshold value, the at least one processor determines that the user is running, and, if the foot contact time is greater than the threshold value, the at least one processor determines that the user is walking.

According to another aspect of the invention, a system includes at least one sensor, adapted to be supported by a user while the user is in locomotion on foot, that determines at least one foot contact time of the user in locomotion; means, adapted to be supported by the user while the user is in locomotion on foot, for comparing a variable having the at least one determined foot contact time as a factor therein with a threshold value; means, adapted to be supported by the user while the user is in locomotion on foot, for determining that the user is walking if the variable is one of greater than or less than the threshold value; and means, adapted to be supported by the user while the user is in locomotion on foot, for determining that the user is running if the variable is the other of greater than or less than the threshold value.

According to another aspect of the invention, a system includes at least one sensor, adapted to be supported by a user while the user is in locomotion on foot, that determines at least one foot contact time of the user in locomotion; means, adapted to be supported by the user while the user is in locomotion on foot, for comparing the at least one determined foot contact time with a threshold value; means, adapted to be supported by the user while the user is in locomotion on foot, for determining that the user is running if the foot contact time is less than the threshold value; and means, adapted to be supported by the user while the user is in locomotion on foot, for determining that the user is walking if the foot contact time is greater than the threshold value.

According to another aspect of the invention, a method includes a step of: (a) with at least one device supported by a user while the user is in locomotion on foot on a surface, determining an amount of force exerted by at least one foot of the user on the surface during at least one footstep taken by the user.

According to another aspect of the invention, a system includes at least one processor adapted to be supported by a user while the user is in locomotion on foot on a surface, the at least one processor being configured to identify an amount of force exerted by at least one foot of the user on the surface during at least one footstep taken by the user.

According to another aspect of the invention, a system includes at least one sensor adapted to be supported by a user while the user is in locomotion on foot on a surface; and means for identifying an amount of force exerted by at least one foot of the user on the surface during at least one footstep taken by the user based upon an output of the at least one sensor.

According to another aspect of the invention, a method includes steps of: (a) with at least one sensor supported by a user, monitoring movement of the user while the user is in locomotion on foot; and (b) determining a cadence of the user based upon an output of the at least one sensor.

According to another aspect of the invention, a method includes steps of: (a) with at least one sensor supported by a user while the user is in locomotion on foot, monitoring movement of the user while the user is in locomotion on foot; and (b) determining a stride length of the user during at least one footstep taken by the user based upon an output of the at least one sensor.

According to another aspect of the invention, a system includes at least one sensor adapted to be supported by a user and to monitor movement of the user while the user is in locomotion on foot; and at least one processor that determines a cadence of the user based upon an output of the at least one sensor.

According to another aspect of the invention, a system includes at least one sensor adapted to be supported by a user and to monitor movement of the user while the user is in locomotion on foot; and at least one processor that, based upon an output of the at least one sensor, determines a stride length of the user during at least one footstep taken by the user.

According to another aspect of the invention, a system includes at least one sensor adapted to be supported by a user and to monitor movement of the user while the user is in locomotion on foot; and means for determining a cadence of the user based upon an output of the at least one sensor.

According to another aspect of the invention, a system includes at least one sensor adapted to be supported by a user and to monitor movement of the user while the user is in locomotion on foot; and means for determining a stride length of the user during at least one footstep taken by the user based upon an output of the at least one sensor.

According to another aspect of the invention, a method includes steps of: (a) with at least one device supported by a user while the user is in locomotion on foot on a surface, identifying one of a pace and a speed of the user relative to the surface; and (b) with the at least one device, determining whether the identified one of the pace and the speed of the user falls within one of a zone of paces and a zone of speeds.

According to another aspect of the invention, a method includes steps of: (a) with at least one device supported by a user while the user is in locomotion on foot, monitoring a distance traveled by the user; and (b) with the at least one device, when the user has traveled a first predetermined distance during the outing, providing an output indicating that the user has traveled the first predetermined distance.

According to another aspect of the invention, a method includes steps of: (a) with at least one device supported by a user while the user is in locomotion on foot, monitoring a distance traveled by the user; (b) receiving a goal distance as an input to the at least one device; and (c) with the at least one device, determining a remaining distance to be traveled by the user to reach one of the input goal distance and a calculated fraction of the input goal distance.

According to another aspect of the invention, a method includes steps of: (a) receiving as an input to at least one device supported by a user a value representing one of a goal time for the user to travel a particular distance, a goal average pace for the user to maintain over the particular distance, and a goal average speed for the user to maintain over the particular distance; (b) with the at least one device, determining a distance traveled by the user while the user is in locomotion on foot; and (c) after the user has traveled a portion of the particular distance, with the at least one device, determining at least one performance parameter based upon the portion of the particular distance traveled and the input value.

According to another aspect of the invention, a method includes steps of: (a) with at least one device, determining a distance traveled by a user while the user is in locomotion on foot; (b) with the at least one device, determining one of a current pace and a current speed of the user; and (c) after the user has traveled a portion of a particular distance, with the at least one device, determining a projected time that it will take the user to travel the particular distance based upon the one of the current pace and the current speed of the user, and the portion of the particular distance already traveled by the user.

According to another aspect of the invention, a method includes steps of: (a) with at least one device supported by a user while the user is in locomotion on foot, determining a distance traveled by the user; (b) during at least one first distance interval during an outing, with the at least one device, providing an indication to the user that the user should be running; and (c) during at least one second distance interval during the outing, with the at least one device, providing an indication to the user that the user should be walking.

According to another aspect of the invention, a system includes at least one processor, adapted to be supported by a user while the user is in locomotion on foot on a surface, that identifies one of a pace and a speed of the user relative to the surface, and that determines whether the identified one of the pace and the speed of the user falls within one of a zone of paces and a zone of speeds.

According to another aspect of the invention, a system includes at least one processor that monitors a distance traveled by a user while the user is in locomotion on foot, and that, when the user has traveled a first predetermined distance during an outing, provides an output indicating that the user has traveled the first predetermined distance.

According to another aspect of the invention, a system includes at least one processor, adapted to be supported by a user while the user is in locomotion on foot, that monitors a distance traveled by the user while the user is in locomotion on foot, that receives a goal distance as an input, and that determines a remaining distance to be traveled by the user to reach one of the input goal distance and a calculated fraction of the input goal distance.

According to another aspect of the invention, a system includes at least one processor, adapted to be supported by a user while the user is in locomotion on foot, that receives as an input a value representing one of a goal time for the user to travel a particular distance, a goal average pace for the user to maintain over the particular distance, and a goal average speed for the user to maintain over the particular distance, that determines a distance traveled by the user while the user is in locomotion on foot, and that, after the user has traveled a portion of the particular distance, determines at least one performance parameter based upon the portion of the particular distance traveled and the input value.

According to another aspect of the invention, a system includes at least one processor, adapted to be supported by a user while the user is in locomotion on foot, that determines a distance traveled by the user while the user is in locomotion on foot, that determines one of a current pace and a current speed of the user, and that, after the user has traveled a portion of a particular distance, determines a projected time that it will take the user to travel the particular distance based upon the one of the current pace and the current speed of the user, and the portion of the particular distance already traveled by the user.

According to another aspect of the invention, a system includes at least one processor, adapted to be supported by a user while the user is in locomotion on foot, that determines a distance traveled by the user while the user is in locomotion on foot; and an indicator coupled to the processor, the at least one processor and the indicator being configured such that, during at least one first distance interval during an outing, the at least one processor causes the indicator to provide an indication to the user that the user should be running, and such that, during at least one second distance interval during the outing, the at least one processor causes the indicator to provide an indication to the user that the user should be walking.

According to another aspect of the invention, a system includes means, adapted to be supported by a user while the user is in locomotion on foot on a surface, for identifying one of a pace and a speed of the user relative to the surface; and means, adapted to be supported by the user while the user is in locomotion on foot, for determining whether the identified one of the pace and the speed of the user falls within one of a zone of paces and a zone of speeds.

According to another aspect of the invention, a system includes means, adapted to be supported by the user while a user is in locomotion on foot, for monitoring a distance traveled by the user while the user is in locomotion on foot; and means, adapted to be supported by the user while the user is in locomotion on foot, for providing an output indicating that the user has traveled a first predetermined distance.

According to another aspect of the invention, a system includes means, adapted to be supported by a user while the user is in locomotion on foot, for monitoring a distance traveled by the user while the user is in locomotion on foot; means, adapted to be supported by the user while the user is in locomotion on foot, for receiving a goal distance as an input to the at least one device; and means, adapted to be supported by the user while the user is in locomotion on foot, for determining a remaining distance to be traveled by the user to reach one of the input goal distance and a calculated fraction of the input goal distance.

According to another aspect of the invention, a system includes means, adapted to be supported by a user while the user is in locomotion on foot, for receiving as an input to at least one device supported by the user a value representing one of a goal time for the user to travel a particular distance, a goal average pace for the user to maintain over the particular distance, and a goal average speed for the user to maintain over the particular distance; means, adapted to be supported by the user while the user is in locomotion on foot, for determining a distance traveled by the user while the user is in locomotion on foot; and means, adapted to be supported by the user while the user is in locomotion on foot, for, after the user has traveled a portion of the particular distance, determining at least one performance parameter based upon the portion of the particular distance traveled and the input value.

According to another aspect of the invention, a system includes means, adapted to be supported by a user while the user is in locomotion on foot, for determining a distance traveled by the user while the user is in locomotion on foot; means, adapted to be supported by the user while the user is in locomotion on foot, for determining one of a current pace and a current speed of the user; and means, adapted to be supported by the user while the user is in locomotion on foot, for, after the user has traveled a portion of a particular distance, determining a projected time that it will take the user to travel the particular distance based upon the one of the current pace and the current speed of the user, and the portion of the particular distance already traveled by the user.

According to another aspect of the invention, a system includes means, adapted to be supported by a user while the user is in locomotion on foot, for determining a distance traveled by the user while the user is in locomotion on foot; means, adapted to be supported by the user while the user is in locomotion on foot, for providing an indication to the user, during at least one first distance interval during an outing, that the user should be running; and means, adapted to be supported by the user while the user is in locomotion on foot, for providing an indication to the user, during at least one second distance interval during the outing, that the user should be walking.

BRIEF DESCRIPTION OF THE DRAWINGS

FIG. 37 is a chart showing various determined performance parameters averaged over fifty meter intervals of a four hundred meter race run by a user;

FIG. 40 is a chart showing the relationship between each of speed and pace of a user and the average ground force exerted by the user while the user is traveling at that speed or pace, as well as accumulated stress values measured per unit distance and per unit time corresponding to that speed or pace of the user.

DETAILED DESCRIPTION OF THE INVENTION

Figure 1:
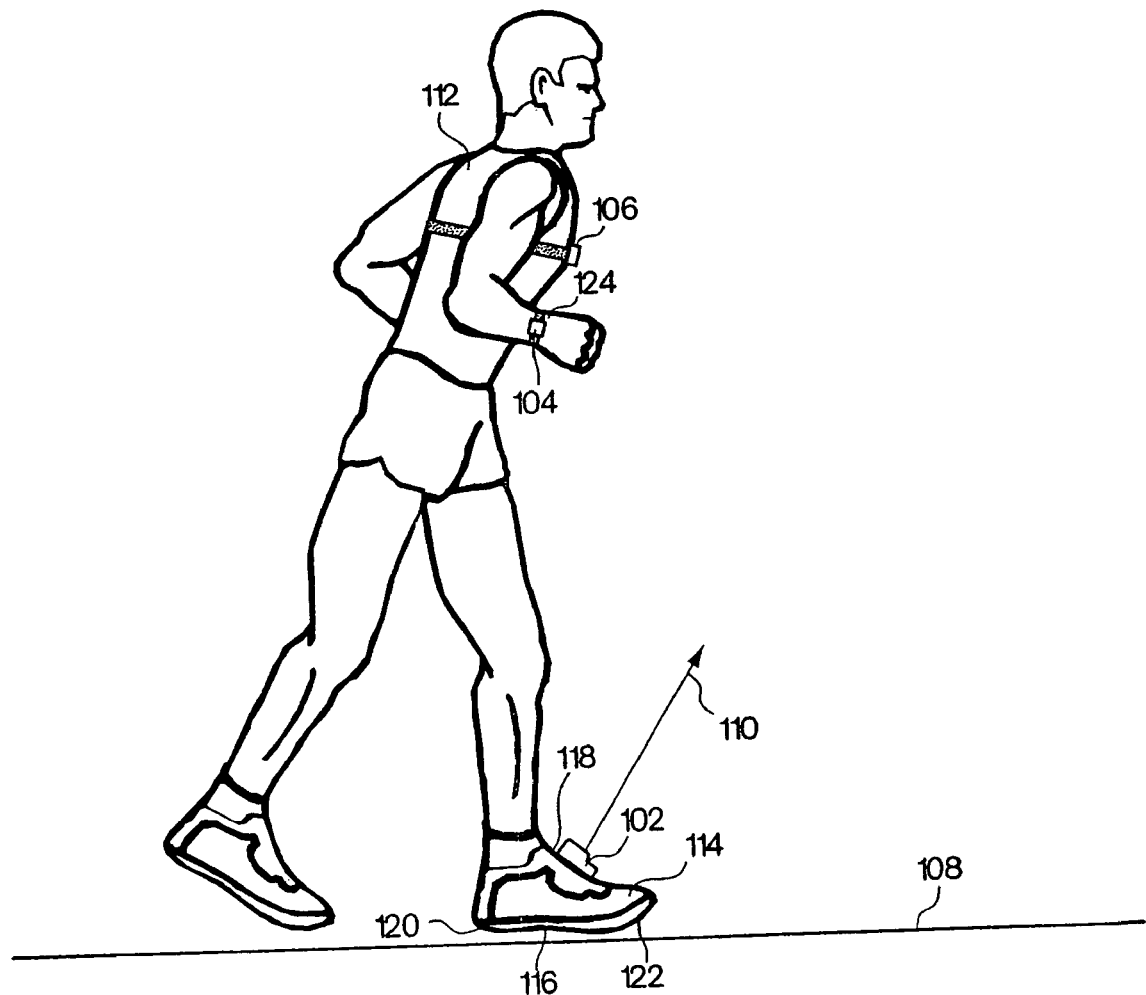
FIG. 1 is an illustration of various components of an activity monitoring system mounted to a user's body in accordance with one embodiment of the present invention.

An illustrative embodiment of a system for monitoring activity of a user in locomotion is shown in FIG. 1. As shown, the system includes a foot-mounted unit 102, a wrist-mounted unit 104, and a chest-mounted unit 106, all attached to a user 112 who is in locomotion (i.e., walking or running) on a surface 108. In accordance with one aspect of the present invention, the foot-mounted unit 102 includes a sensor for sensing motion of a foot 114 of the user 112.

The sensor included in the foot-mounted unit 102 may be any of a number of devices capable of sensing the motion of the user's foot 114, and the invention is not limited to the use of any particular type of sensor. In one illustrative embodiment, for example, the foot-mounted unit 102 includes a solid-state accelerometer that senses acceleration along an acceleration sensing axis 110, as shown in FIG. 1. In another embodiment, the sensor includes a low-cost accelerometer such as that disclosed in U.S. Pat. No. 6,336,365, the entire contents of which are hereby incorporated herein by reference. Other sensors that may be used include, for example, pressure-sensitive resistive switches, piezoelectric transducers, GMR sensors, simple contact switches, mercury switches, or any other devices capable of generating a signal indicative of motion of the foot 114 of the user 112 while the user 112 is in locomotion.

It should be appreciated that, advantageously, several of the sensors that can be used in the foot-mounted unit 102 do not require compression forces thereon to sense motion of the foot 114, and therefore need not be subjected to the physical wear and tear typically exerted on motion sensors such as pressure-sensitive resistive switches, contact switches, and the like. Because such sensors are not required to be subjected to compression forces to sense motion, they may be located above a bottom surface 116 of the user's foot 114, e.g., on an instep 118 of the user's shoe or on the user's ankle or waist. Therefore, the sensors included in these types of devices need not be incorporated within or on the sole-portion of a user's shoe, and specially-designed shoes need not be used to accommodate them.

It should also be appreciated that the foot-mounted unit 102 may alternatively be mounted at other locations on the body of the user 112, and the invention is not limited to embodiments wherein the unit 102 is mounted on the user's foot 114. It is important only that the output of the sensor included in the unit 102 produces a signal in response to activity of the user 112 (e.g., movement of the user's foot 114) while the user 112 is in locomotion. The unit 102 may, for example, be mounted on the ankle, thigh, waist, chest, etc., of the user 112 in connection with different embodiments of the invention.

As shown in FIG. 1, the wrist-mounted unit 104 may be mounted to a wrist 124 of the user 112. The wrist-mounted unit 104 may, for example, include a display for displaying information to the user 112 based upon data accumulated by the foot-mounted unit 102 and transmitted to the wrist-mounted unit 104 via a wireless communication link (e.g., over a radio-frequency (RF) network). Communication between the foot-mounted unit 102 and the wrist-mounted unit 104 may either be one-way or two-way.

In one illustrative embodiment, the foot-mounted unit 102 accumulates and transmits data to the wrist-mounted unit 104 where it may be used to display, for example, the current pace (or speed) of the user 112, as well as the average pace (or speed) of the user 112, the energy (e.g., calories) expended by the user 112, and the total distance traveled by the user 112 during a particular time interval. One illustrative technique for calculating energy expenditure based upon one or more measured foot contact time (Tc) values is disclosed in U.S. Pat. No. 5,925,001, which is hereby incorporated herein by reference in its entirety. Examples of these and other information types that may be simultaneously displayed to the user 112 in this regard are described below in connection with FIG. 32.

It should be appreciated that the wrist-mounted unit 104 need not be secured to the wrist 124 of the user 112, and may alternatively be disposed elsewhere on the user's body or at a location remote from the user 112. For example, in alternative embodiments, the unit 104 may be a hand-held device that can be carried by or placed in a pocket of the user 112, it may be a so-called "head's up" display incorporated into a pair of sunglasses or the like so as to display information to the user 112 on an interior surface of the sunglasses, or it may be a wrist-mounted or hand-held device worn or carried by a third person, e.g., a track coach.

It should further be appreciated that the functionality of the wrist-mounted unit 104 may alternatively be incorporated into the foot-mounted unit 102, so that the foot-mounted unit 102 may itself display the relevant information to the user 112. As still another alternative, the foot-mounted unit 102 and/or the wrist-mounted unit 104 may simply accumulate data during a given time period that the user 112 is in locomotion, and may later download the accumulated data to a personal computer or the like for viewing and/or analysis.

In addition to those described herein, other suitable embodiments of foot-mounted units and wrist-mounted units are described in U.S. Pat. No. 6,018,705, which is hereby incorporated herein by reference in its entirety.

In the embodiment of FIG. 1, the chest-mounted unit 106 may, for example, monitor the heart rate of the user 112, and transmit information regarding the user's heart rate over a wireless communicator channel (e.g., over an RF network) to the wrist-mounted unit 104. In one illustrative embodiment, the foot-mounted unit 102, the wrist-mounted unit 104, and the chest-mounted unit 106 are all members of the same RF network so that each of the units 102, 104 and 106 is capable of communicating with the other members of the network.

The chest-mounted unit 106 may be any of a number of devices capable of monitoring a heart rate or other physiological parameter of interest of the user 112, and the invention is not limited to any particular type of physiological monitoring device. In some embodiments, for example, the chest-mounted unit 106 may comprise a commercially-available heart rate monitor such as the type manufactured by Polar Electo Inc. of Woodbury, N.Y., "www.polarusa.com," including or modified to include a suitable RF transmitter capable of communicating with the other devices included in the network. In one embodiment, the chest-mounted device 106 comprises a heart-rate monitor that has sufficient intelligence to analyze the a signal indicative of the user's heartbeat and to calculate a numerical value representing the user's current heart rate, rather than merely outputting a raw signal in response to detected heartbeats. In this manner, processing power of the wrist-mounted unit 104 or other device that receives data from the heart-rate monitor is not consumed in performing these functions.

It should be appreciated that it is not critical that the unit 106 be mounted to the chest of the user 112, and that, in alternative embodiments of the invention, the unit 106 may instead be mounted to other portions of the user's body where it may sense the physiological parameter of interest. The functionality of the chest-mounted unit 106 may even be incorporated into either the foot-mounted unit 102 or the wrist-mounted unit 102 in alternative embodiments. For example, the foot-mounted unit 102 or the wrist-mounted unit 104 may itself include a transducer capable of sensing the heart rate of the user 112. An example of a transducer capable of performing this function is a fluid-filled bladder having a sonic transducer associated therewith that monitors audio signals sensed through the fluid in the bladder. An example of such a device is described in U.S. Pat. No. 5,853,005, which is hereby incorporated herein by reference in its entirety.

With a system such as that shown in FIG. 1, the user 112 may simultaneously view information on the wrist-mounted unit 104 regarding his or her heart rate, energy expenditure, current running or walking pace and/or speed, average walking or running pace and/or speed, and distance traveled during a particular outing, or one or more selected ones of the same while the user 112 is running or walking. Such information has not heretofore been available in this manner to a user in locomotion on foot. As used herein, "outing" refers to an exercise regime engaged in by a user during which the user is in locomotion on foot, regardless of whether the user is running, walking, jogging, etc.

Figure 2A:
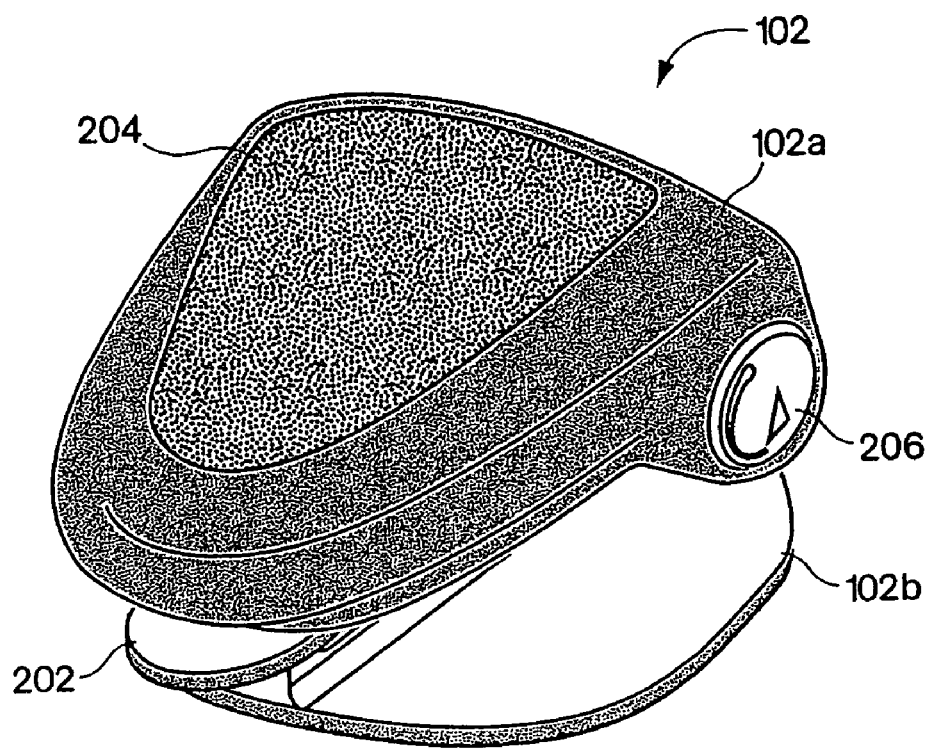
FIGS. 2A and 2B show perspective and side views, respectively, of an example embodiment of the foot-mounted unit of the activity monitoring system shown in FIG. 1.
Figure 2B:
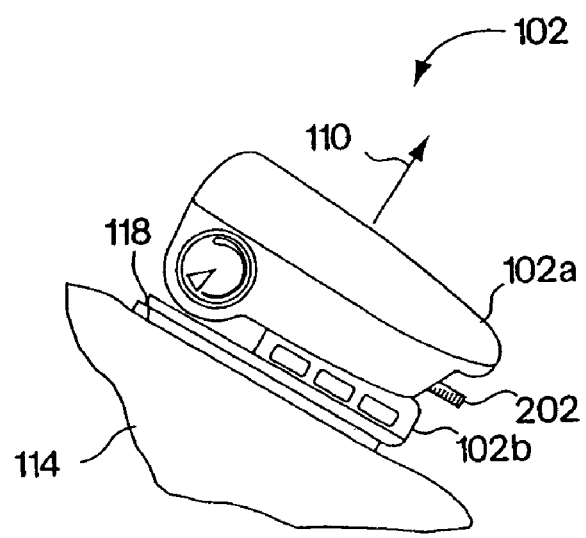

FIGS. 2A-2B show, respectively, perspective and side views of an example embodiment of the foot-mounted unit 102 shown in FIG. 1. As shown in FIG. 2A, the foot-mounted unit 102 may include a housing portion 102a and a pedestal portion 102b, and the pedestal portion 102b may be mounted, for example, to the instep 118 of the user's foot 114. In the illustrative embodiment shown, all of the electronics for the foot-mounted unit 102 are disposed in the housing portion 102a, and the pedestal portion 102b includes a lever 202 which may be depressed to release the housing portion 102a from the pedestal portion 102b. In this manner, the user 112 may remove the housing portion 102a (and the electronic components included therein) from the pedestal portion 102b while the pedestal portion 102b remains disposed on the user's shoe (e.g., underneath the shoelaces of the shoe). In this manner, the user 112 may use the same housing portion 102a with two or more different pedestal portions 102b disposed on different pairs of shoes, thereby enabling the user 112 to readily transfer the housing portion 102a from one pair of shoes to another. In addition, the user may remove the housing portion 102a from the pedestal portion 102b (and the shoe) to wash the shoe, or simply for aesthetic reasons. A detailed example of a two-piece, detachable, foot-mounted apparatus that may be used as the foot-mounted unit 102 is disclosed in U.S. Pat. No. 6,122,340, which is hereby incorporated herein by reference in its entirety. Alternatively, the foot-mounted unit 102 may be secured to the user's shoelaces or elsewhere using an elastic cord or the like. An example of such a foot-mounted unit 102, which may be secured to a shoelace, is disclosed in U.S. Pat. No. 6,560,903, which is hereby incorporated herein by reference in its entirety.

Figure 3A:
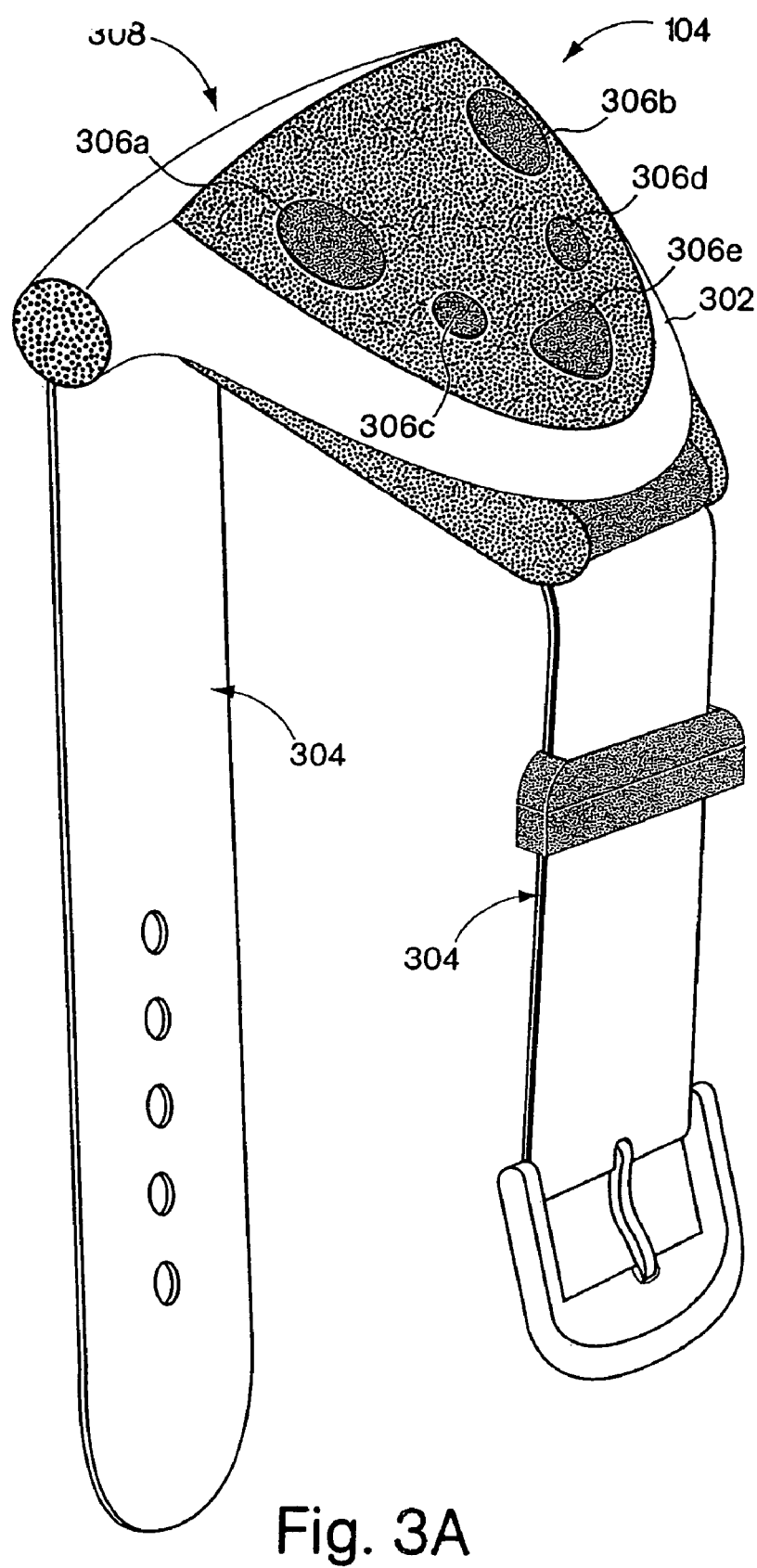
FIGS. 3A and 3B show perspective cutaway and side views, respectively, of an example embodiment of the wrist-mounted unit of the activity monitoring system shown in FIG. 1.
Figure 3B:
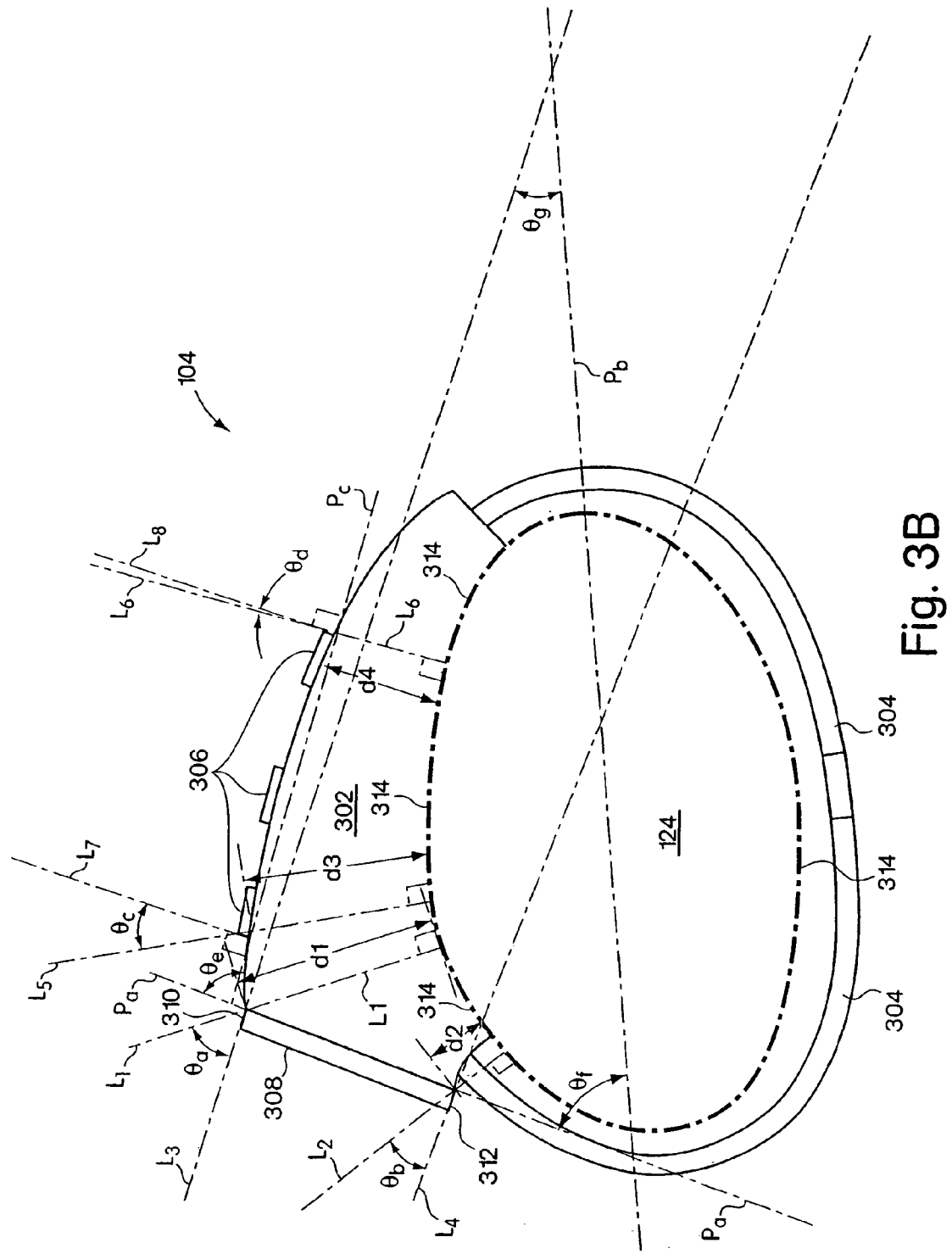

FIGS. 3A and 3B show, respectively, perspective and side views of an example embodiment of the wrist-mounted unit 104 shown in FIG. 1. FIG. 3B shows the wrist-mounted unit 104 as it may appear when mounted to the wrist 124 (shown in cross-section) of the user 112. In the illustrative embodiment shown, the wrist-mounted unit 104 includes a housing 302, and a strap 304 for securing the housing 302 to the wrist 124. As shown, the housing 302 may include a display face 308 on which information may be displayed to the user 112. The housing 302 may also have a plurality of buttons 306a-e disposed thereon to enable the user to implement the functionality of circuitry (described below in connection with FIG. 4) included in the housing 302.

Referring to FIG. 3B, it is illustrated how the housing 302 may be configured so as to be ideally suited, in an ergonomic sense, for a runner or walker. Characters (e.g., ASCII characters) may be displayed on the display face 308 such that tops of and bottoms of the characters correspond, respectively, to a top edge 310 and a bottom edge 312 of the display face 308. As shown in FIG. 3B, the display face 308 (which is oriented in the plane $P_a$) may be tilted at an acute (i.e., between 0-90°) angle $\theta_f$ with respect to a plane $P_b$ (which passes through a widest portion of the wrist 124 and extends through the forearm of the user 112). When tilted in this manner, the display face 308 may be readily viewed by the user 112 without requiring the user 112 to tilt his or her wrist at an angle that is awkward for the user 112 when the user 112 is running or walking. In addition, in the FIG. 3 embodiment, each of the buttons 306 is disposed substantially in a plane $P_c$ ("the button plane") which is oriented substantially perpendicular to a direction in which the buttons 306 are depressed during normal operation. As shown in FIG. 3B, the button plane $P_c$ may also be tilted at an acute angle $\theta_g$ with respect to the plane $P_b$ so as to make the buttons 306 more easily accessible to the user 112 when the user 112 is walking or running.

The manner in which the display face 308 of the wrist-mounted unit 104 is tilted may be defined with reference to a pair of lines $L_1$ and $L_2$ shown in FIG. 3B. As shown, each of the lines $L_1$ and $L_2$ is oriented normal to (i.e., perpendicular with respect to) a surface 314 of the user's wrist 124. The line $L_1$ intercepts the top edge 310 of the display face 308, and the line $L_2$ intercepts the bottom edge 312 of the display face 308. In the embodiment of FIG. 3B, a distance d1 (measured along the line $L_1$) between the surface 314 of the user's wrist 124 and the upper edge 310 of the display face 308 is substantially greater than a distance d2 (measured along the line $L_2$) between the surface 314 of the user's wrist 124 and the bottom edge 312 of the display face 308. The distance d1 may, for example, be 5%, 10%, 25%, 50%, 100%, 200%, 300%, or more greater than the distance d2. Any of a number of other ratios between the distances d1 and d2 also are possible, and the invention is not limited to any particular ratio between these distances.

The manner in which the display face 308 of the wrist-mounted unit 104 is tilted may also be defined in terms of the respective relationships between the lines $L_1$ and $L_2$ and a pair of lines $L_3$ and $L_4$ shown in FIG. 3B. As shown, each of the lines $L_3$ and $L_4$ is oriented normal to the plane $P_a$ in which the display face 308 is disposed. The line $L_3$ passes through the top edge 310 of the display face 308 and the line $L_4$ passes through the bottom edge 312 of the display face 308. As illustrated, assuming the lines $L_1$ and $L_2$ intercept the lines $L_3$ and $L_4$, respectively, the line $L_1$ forms an angle $\theta_a$ with respect to the line $L_3$, and the line $L_2$ forms an angle $\theta_b$ with respect to the line $L_4$. When the angles $\theta_a$ and $\theta_b$ in FIG. 3B are measured in a clockwise direction beginning with the lines $L_3$ and $L_4$, respectively, each of the angles $\theta_a$ and $\theta_b$ is acute (i.e., between 0-90°). This may be compared to prior art wrist-watch configurations wherein the plane $P_a$ in which the display face 308 is disposed typically is parallel to the plane $P_b$ of the user's wrist 124. In such prior art devices, the angle $\theta_a$ (when measured as discussed above) is slightly greater than 0°, and the angle $\theta_b$ is slightly less than 360°. Therefore, in a typical prior art wrist-watch, only the angle $\theta_a$, and not the angle $\theta_b$, (when measured as discussed above) is between 0-90°.

Similar to the plane $P_a$ in which the display face 308 is disposed, the manner in which the button plane $P_c$ of the wrist-mounted unit 104 is tilted may be defined with reference to a pair of lines $L_5$ and $L_6$ shown in FIG. 3B. As shown, each of the lines $L_5$ and $L_6$ is oriented normal to the surface 314 of the user's wrist 124. The line $L_5$ intercepts a button in the button plane $P_c$ that is closest to the display face 308 (e.g., the button 306a of FIG. 3A), and the line $L_6$ intercepts a button in the button plane $P_c$ that is farthest away from the display face 308 (e.g., the button 306e of FIG. 3A).

In the embodiment of FIG. 3B, a distance d3 (measured along the line $L_5$) between the surface 314 of the user's wrist 124 and the button 306 closest to the display face 308 is substantially greater than a distance d4 (measured along the line $L_6$) between the surface 314 of the user's wrist 124 and the button 306 farthest away from the display face 308. The distance d3 may, for example, be 5%, 10%, 25%, 50%, 100%, 200%, 300%, or more greater than the distance d4. Any of a number of other ratios between the distances d3 and d4 also are possible, and the invention is not limited to any particular ratio between these distances.

The manner in which the button plane $P_c$ of the wrist-mounted unit 104 is tilted may also be defined in terms of the respective relationships between the lines $L_5$ and $L_6$ and a pair of lines $L_7$ and $L_8$ shown in FIG. 3B. As shown, each of the lines $L_7$ and $L_8$ is oriented normal to the button plane $P_c$. The line $L_7$ passes through the button 306 disposed closest to the display face 308, and the line $L_8$ passes through the button 306 disposed farthest away from the display face 308. As illustrated, assuming the lines $L_5$ and $L_6$ intercept the lines $L_7$ and $L_8$, respectively, the line $L_5$ forms an angle $\theta_c$ with respect to the line $L_7$, and the line $L_6$ forms an angle $\theta_d$ with respect to the line $L_8$. When the angles $\theta_c$ and $\theta_d$ in FIG. 3B are measured in a clockwise direction beginning with the lines $L_5$ and $L_6$, respectively, each of the angles $\theta_c$ and $\theta_d$ is acute (i.e., between 0-90°). This is in contrast to prior art wrist watches wherein functional buttons are disposed in planes that are oriented so that at least one of the angles $\theta_c$ and $\theta_d$ (when measured as discussed above) is either exactly 90° (e.g., when buttons are disposed on the side of a watch) or greater than 90° (e.g., when buttons are disposed on a watch's face).

Also shown in FIG. 3B is an angle $\theta_c$ measured between the plane $P_a$ in which the display face 308 is disposed and the button plane $P_c$. The angle $\theta_e$ may be any of a number of suitable angles, depending on the desired ergonomic characteristics of the wrist-mounted unit 104. For example, the angle $\theta_e$ may be acute as shown in FIG. 3B, it may be a perfect right angle, or it may be obtuse (i.e., greater than 90°).

Figure 4:
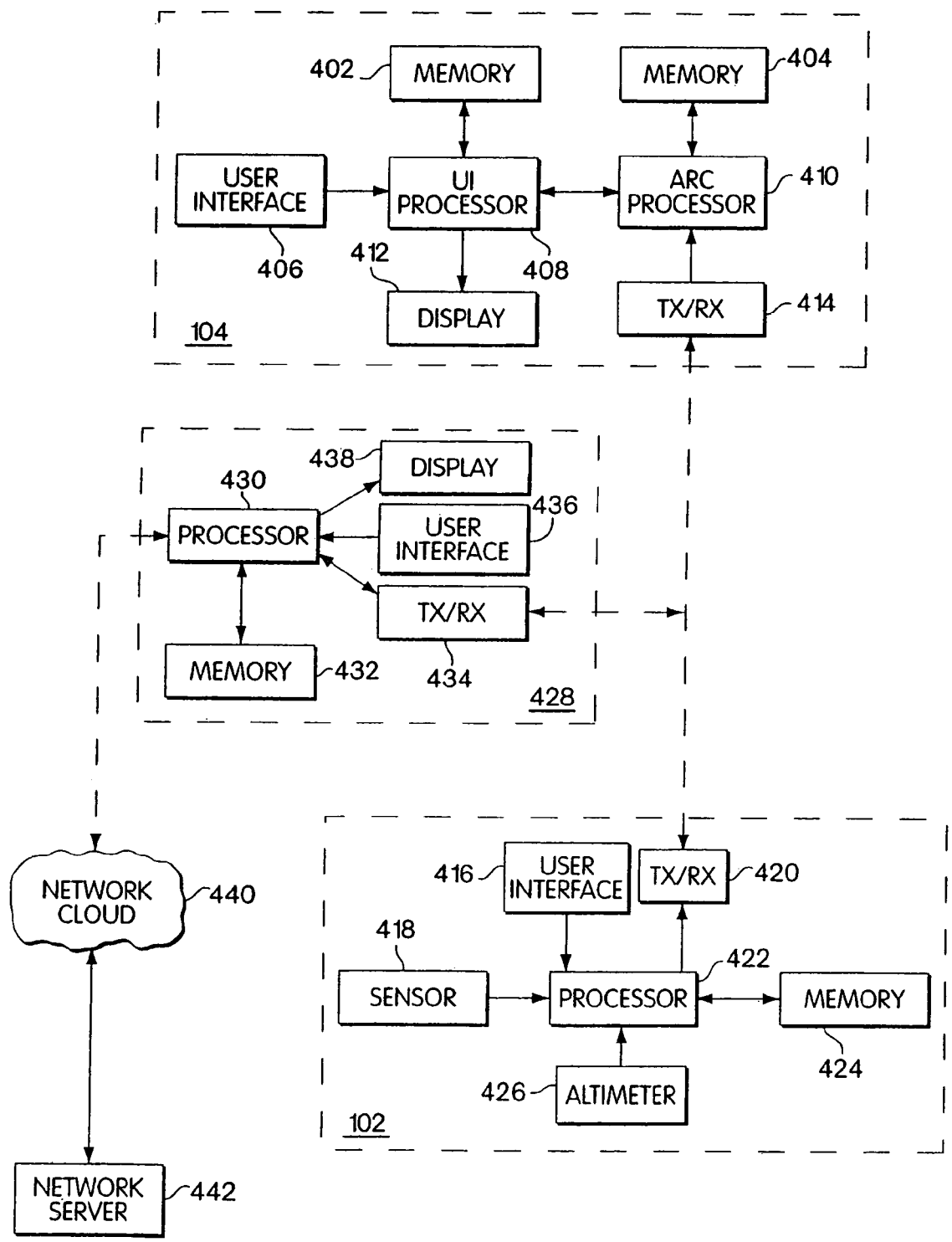
FIG. 4 is a block diagram of various electronic components that may be included in the foot-mounted and wrist-mounted units of FIG. 1-3 in accordance with one embodiment of the invention.

FIG. 4 shows a block diagram of various electronic components that may be disposed in each of the units 102 and 104 in accordance with one illustrative embodiment of the invention. It should be appreciated, however, that the circuitry within each of the wrist-mounted unit 104 and the foot-mounted unit 102 may take on any of a number of alternative configurations, and the invention is not limited to the particular circuitry or components described herein for performing the various functions. Also shown in FIG. 4 are additional components of a network system that may be employed in connection with an embodiment of the invention. In particular, the system of FIG. 4 further includes a computer 428 and a network server 442, each coupled to a network cloud 440.

As shown, the foot-mounted unit 102 may include a processor 422, as well as a sensor 418, a user interface 416, a transceiver 420, and a memory 424 coupled to the processor 422. The wrist-mounted unit 104, may include both a user interface (UI) processor 408 and an arithmetic, radio, and calibration (ARC) processor 410, as well as memories 402 and 404 (coupled to the UI processor 408 and the ARC processor 410, respectively), a user interface 406 (coupled to the UI processor 408), a display 412 (coupled to the UI processor 408), and a transceiver 414 (coupled to the ARC processor 410). The computer 428 may include a processor 430, a memory 432, a transceiver 434, a user interface 436, and a display 438. In one embodiment, the computer 428 is a personal computer (PC) to which the user 112 has access. The network server 442 is configured to communicate (via the network cloud 440) with the computer 428, as well as with a number of other computers similar the computer 428.

Each of the processors 408, 410, 422, and 430 in the FIG. 4 embodiment may be any processor, controller, hard wired circuit, or the like that is capable of performing at least some of the functions discussed herein, and the invention is not limited to the use of any particular types of processors. In addition, in alternative embodiments, the functionality of each of the processors shown in FIG. 4 may be performed by one or more of the other processors shown and/or may be distributed across one or more additional processors. In addition, the functionality of the UI and ARC processors 408 and 410 may be implemented using only a single processor. In one embodiment, the UI processor 408 may comprise, for example, part number NSM63188, manufactured by OKI Electronics; the ARC processor 410 may comprise, for example, part number PIC16C63, manufactured by Microchip, Inc.; and the processor 422 may comprise, for example, part number PIC16C73, manufactured by Microchip, Inc.

The network cloud 440 may, for example, represent the Internet. Of course, it may alternatively represent any other network scheme. The network server 442 and the computer 428 therefore may communicate with one another, and share data and responsibility for various functional attributes with one another in any manner known in the art. In one embodiment, the network server 442 serves as an application service provider for the computer 428. It should be appreciated, however, that such a configuration is not critical, as the network server 442 may likewise serve solely as a repository for the storage and retrieval of information. User-specific information stored on the network server 442 may be accessed, for example, using a user-specific (identification) ID. Access to this information may also require a password or successful implementation of some other security measure.

The user interface 406 may correspond, for example, to the buttons 306 shown in FIGS. 3A-B, and the user interface 416 may correspond, for example, to the button 204 shown in FIG. 2A. It should be appreciated, however, that the invention is not limited in this respect, and that different, fewer, or additional user interface buttons or other suitable user-interface devices or circuitry (e.g., voice activated interface devices) may alternatively be employed. The memories 402, 404, 424, and 432 may each store a plurality of instructions which, when executed by the processor coupled thereto, may perform one or more of the routines described below. The structure and capabilities of the various components of the computer 428 (i.e., the processor 430, memory 432, user interface 436, and display 438), as well as the network server 442, are well understood in the art, and therefore will not be described in further detail.

As discussed above, the sensor 418 in the foot-mounted unit 102 may be any of a number of devices capable of monitoring the motion of the user's foot 114 to determine, for example, time periods that the user's foot 114 is in contact with the ground or is in the air. In one illustrative embodiment, a sensor which does not require compression forces thereon to sense motion is employed so as to reduce the wear and tear on the sensor 418. Because it is not necessary for such a sensor to be disposed between the bottom surface 116 of the user's foot 114 and the surface 108 on which the user 112 is walking or running, the entire foot-mounted unit 102 (including the sensor 418) may be mounted above the bottom surface 116 of the user's foot 114. For example, the entire foot-mounted unit 102 may be mounted on the instep 118 of the user's foot 114 as shown in FIG. 1.

In such an embodiment, the foot-mounted unit may readily be disposed on prefabricated footwear (e.g., a running shoe), and specialized footwear having one or more sensors disposed so as to be located underneath the user's foot 114 need not be employed. It should be appreciated, however, that the invention is not limited in this respect, and that sensors such as contact switches, piezoelectric, pressure sensitive transducers, or the like, that are disposed between the user's foot 114 and the surface 108 to sense motion of the user's foot 114 with respect to the surface 108 may be employed in some embodiments of the invention.

As discussed below in more detail, an output signal from the sensor 418 may be provided to the processor 422, and the processor 422 may analyze the received signal in accordance with an algorithm stored in the memory 424. Data generated by the processor 422 in response to this analysis, may be transmitted by the transceiver 420 (e.g., over an RF communication channel) to the transceiver 414 of the wrist-mounted unit 104. It should be appreciated, of course, that other wireless transmission media may alternatively be employed, and the invention is not limited to the use of an RF communication channel as the wireless communication link between the units 102 and 104. It should also be appreciated that, in some embodiments of the invention, the transceiver 420 may comprise only a transmitter and the transceiver 414 may comprise only a receiver, and that the invention is not limited to embodiments wherein transceivers are employed in both units.

When information from the foot-mounted unit 102 is received by the transceiver 414 of the wrist-mounted unit 104, this information may be processed by the ARC processor 410 to calculate various parameters to be displayed to the user 112 on the display 412. Any of a number of parameters may be calculated based upon the information received from the foot-mounted unit 102, and the invention is not limited to the calculation of any particular parameters. In one illustrative embodiment, the ARC processor 410 is responsible for calculating both the instantaneous and average pace of the user 112, the distance traveled and calories expended by the user 112 during a given period, and the total time interval during which the distance, pace, and calorie measurements are calculated (i.e., a chronograph). In alternative embodiments, one or more of these parameters may instead be calculated by processor 422 of the foot-mounted unit 102, and the pre-calculated values may then be passed to the wrist-mounted unit 104.

After the ARC processor 410 calculates or receives the aforementioned parameters, the calculated parameters may be passed to the UI processor 408 which is responsible for displaying them on the display 412. The UI 408 processor may also perform standard time and date keeping functions, and may display time and date information on the display 412 either along with, or separately from, the parameters received from the ARC processor 410.

By properly manipulating the user-interface 406 (e.g., by pushing selected ones of the buttons 306b-e), the user 112 may, for example, start or stop the time period during which data received from the foot-mounted unit 102 is accumulated, may alter the display modes of the UI processor 408/display 412, or may otherwise enable the user 112 to control of the functionality of the UI processor 408 and/or the ARC processor 410.

As shown, the transceiver 420 and/or the transceiver 414 may also communicate with the transceiver 434 of the computer 428 via a wireless communication link. As discussed below in more detail, this communication link enables information to be downloaded from the wrist-mounted unit 104 and/or the foot-mounted unit 102 to the computer 428, and possibly, in turn, to the network server 428. This communication link also enables the user 112 to operate software running on the computer 428 and/or network server 442 to analyze received data and/or to select operating parameters for the wrist-mounted unit 104 and/or foot-mounted unit 102, which parameters then may be transmitted to those devices via the transceiver 434.

As discussed below in more detail, the parameters calculated by the wrist-mounted unit 104 and/or the foot-mounted unit 102, as well as parameters calculated by or calculated in response to a signal from the chest-mounted unit 106, may be analyzed in various ways so as to provide feedback to the user during or after an exercise session by the user. During an exercise session, such analysis may be performed by the processor(s) in the foot-mounted unit 102 and/or the wrist-mounted unit 104, and feedback may be provided to the user by either device. For example, the user may receive a textual message on the display 412, may receive an audio, vibrational, or visual (e.g., a light) alert via the user interface 406 or the user interface 416, or may receive any other indication responsive to one or more identified characteristics in analyzed data. As used herein, the phrase "indication to the user" refers to the output provided by any one or any combination of these user-feedback methods or any other user-feedback method known in the art.

The system of FIG. 4 may be designed such that multiple users (e.g., multiple family members or track team members) may employ the same equipment, but so that user-specific data and operating parameters may be selectively stored and accessed. This may be accomplished, for example, by requiring each user to input a particular ID code or name, or to select an appropriate ID code or name from a list thereof, and permitting access to or logging information and parameters based upon that ID code or name. The ID code or name may, for example, be entered or selected using any of the devices in the system, and then may be transmitted, if necessary, to the other devices.

Figure 5:
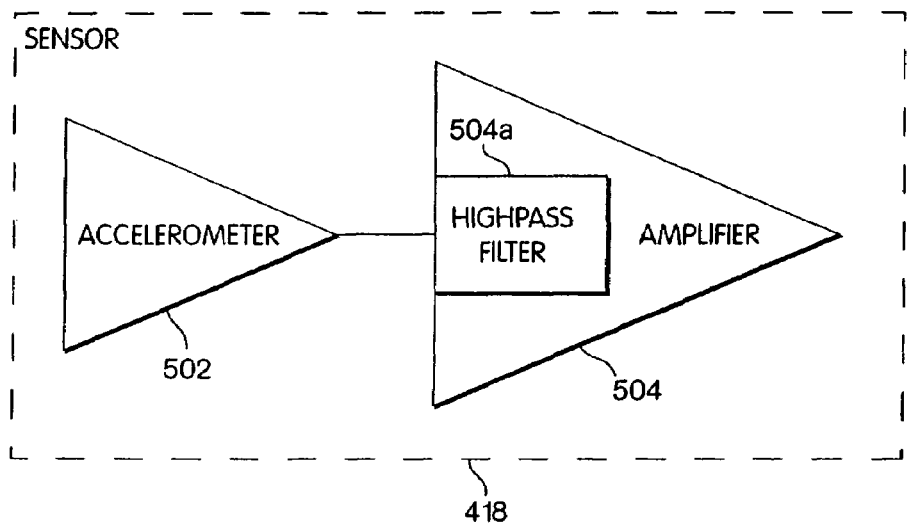
FIG. 5 is a block diagram of an example of an accelerometer-based sensor that may be employed in the foot-mounted unit of FIGS. 1, 2, and 4 in accordance with one embodiment of the invention.

FIG. 5 shows an illustrative example of a motion sensor that may be employed as the sensor 418 in the FIG. 4 embodiment. In the example shown, the sensor 418 includes an accelerometer 502, and an amplifier circuit 504 (including a high-pass filter 504a integrated therein). The accelerometer 502 may comprise any of numerous devices or circuits capable of detecting acceleration of the user's foot 114 and producing an output signal in response thereto, and the invention is not limited to the use of any particular type of accelerometer. In one illustrative embodiment, for example, the accelerometer 502 comprises part number ADXL250, manufactured by Analog Devices, Inc. Again, as mentioned above, it should be appreciated that the invention is not limited to embodiments that employ an accelerometer as the sensor 418, and that other suitable devices may alternatively be used.

Figure 6:
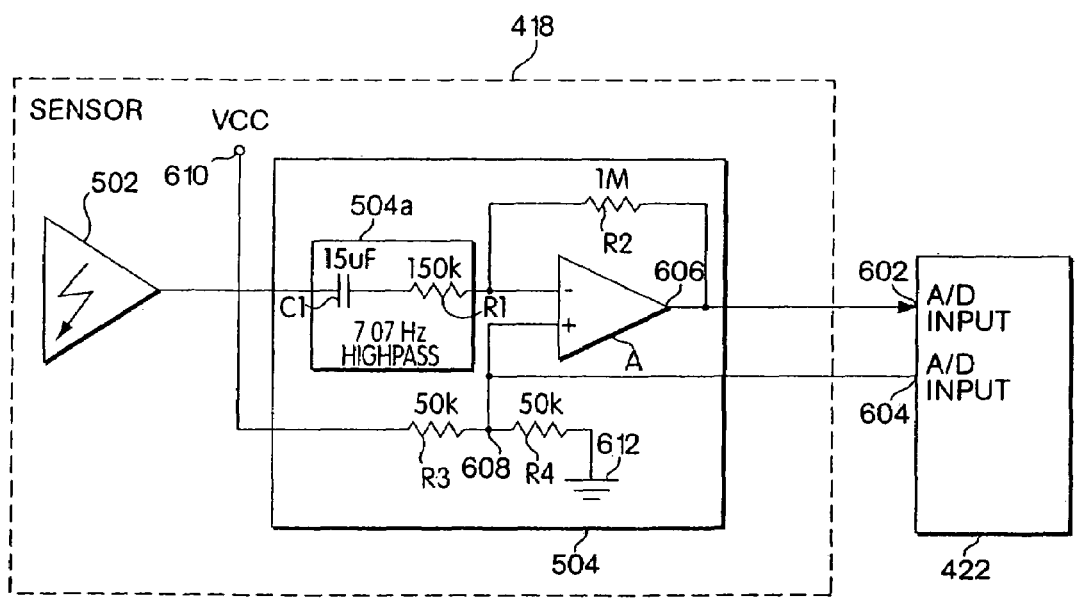
FIG. 6 is a partial-schematic, partial-block diagram of the sensor and processor of the foot-mounted unit shown in FIGS. 4 and 5 in accordance with one embodiment of the invention.

FIG. 6 shows a partial-schematic, partial-block diagram of an example embodiment of the sensor 418 of FIGS. 4 and 5, in addition to the processor 422 of FIG. 4. As shown in FIG. 6, the amplifier circuit 504 may include a capacitor C1, resistors R1-R4, and an operational amplifier A. The operational amplifier A may, for example, comprise part number MA418, manufactured by MAXIM, Inc.

In the example embodiment of FIG. 6, the resistor R1 is connected between the input capacitor C1 and the inverting input of the operational amplifier A, and the resistor R2 is connected in feedback between the inverting input and an output 606 of the operational amplifier A. The combination of the input capacitor C1 and the resistor R1 form a high-pass filter, and the configuration of the resistors R1 and R2 place the amplifier circuit 504 in an inverting configuration with a gain-factor dependent on the relative values of the resistors R1 and R2. In the embodiment shown, the resistor R2 has a value of 1 mega-ohm, and the resistor R2 has a value of 150 kill-ohms, so that the gain factor of the amplifier circuit 504 is approximately (−6.6). In addition, in the embodiment shown, the capacitor C1 has a value of 0.15 microfarads, so that the high-pass filter section 504a of the amplifier circuit 504 cuts off input signal frequencies that are less than approximately 7.07 hertz.

In the FIG. 6 embodiment, the resistor R3 is connected between a VCC supply node 610 and the non-inverting input of the operational amplifier A, and the resistor R4 is connected between the non-inverting input of the operational amplifier A and a ground node 612 of the circuit. The VCC supply node 610 may be maintained at approximately "5" volts (e.g., regulated from a six-volt battery) in relation to the ground node 612, and the resistors R3 and R4 may be of equal values (e.g., "50" kill-ohms each) so that the voltage at a node 608 between the resistors R3 and R4, which is connected to the non-inverting input of the amplifier A, is maintained approximately midway between the voltage at the VCC supply node 610 and the ground node 612 (e.g., at approximately "2.5" volts). It should be appreciated, of course, that any other suitable supply voltage (e.g., "3" volts) may alternatively be applied between the VCC supply node 610 and the ground node 612, and that the invention is not limited to the use of a "5" volt supply.

As shown in FIG. 6, the node 608 is also coupled to a reference input 604 of the processor 422, and the output 606 of the operational amplifier A is connected to a signal input 602 of the processor 422. In one embodiment, the processor 422 includes on-board memory, A/D converters, and timers.

Therefore, in such an embodiment, the memory 424 of the embodiment of FIG. 4 may be incorporated into the same micro-chip as the processor 422. It should be appreciated, however, that the invention is not limited in this respect, and that any of the above-noted on-board elements may alternatively be employed external to the controller 422.

In the circuit of FIG. 6, when the VCC supply node 610 is maintained at five volts, the input 604 of the processor 422 may serve as a zero-reference that is maintained at approximately "2.5" volts (as described above), and the input 602 of the processor 422 may serve as a variable input that fluctuates between "0" and "5" volts. The processor 422 may, for example, sample the voltage at each of the inputs 602 and 604 at a rate of approximately "500" samples per second, and convert each of these samples into a respective 8-bit unsigned digital value. Therefore, for each sample taken at the inputs 602 and 604, the voltage at each of these inputs, with reference to a digital ground input (not shown) of the processor 422, will be converted to a "level" between "0" and "255."

Because of the voltage division performed by the resistors R3 and R4, each sample taken at the input 604 remains close to the level "128" of the "255" possible levels. Each sample taken at the input 602 fluctuates between the level "0" and the level "255" depending on the voltage generated by the accelerometer 502 in response to acceleration thereof. A positive acceleration of the accelerometer 502 along the acceleration sensing axis 110 may, for example, cause the sample taken at the input 604 to be some level between the levels "129" and "255," whereas a negative acceleration of the accelerometer 502 along the acceleration sensing axis 110 (see FIGS. 1 and 2B) may, for example, cause the sample taken at the input 604 to be some level between the levels "0" and "127."

Figure 7:
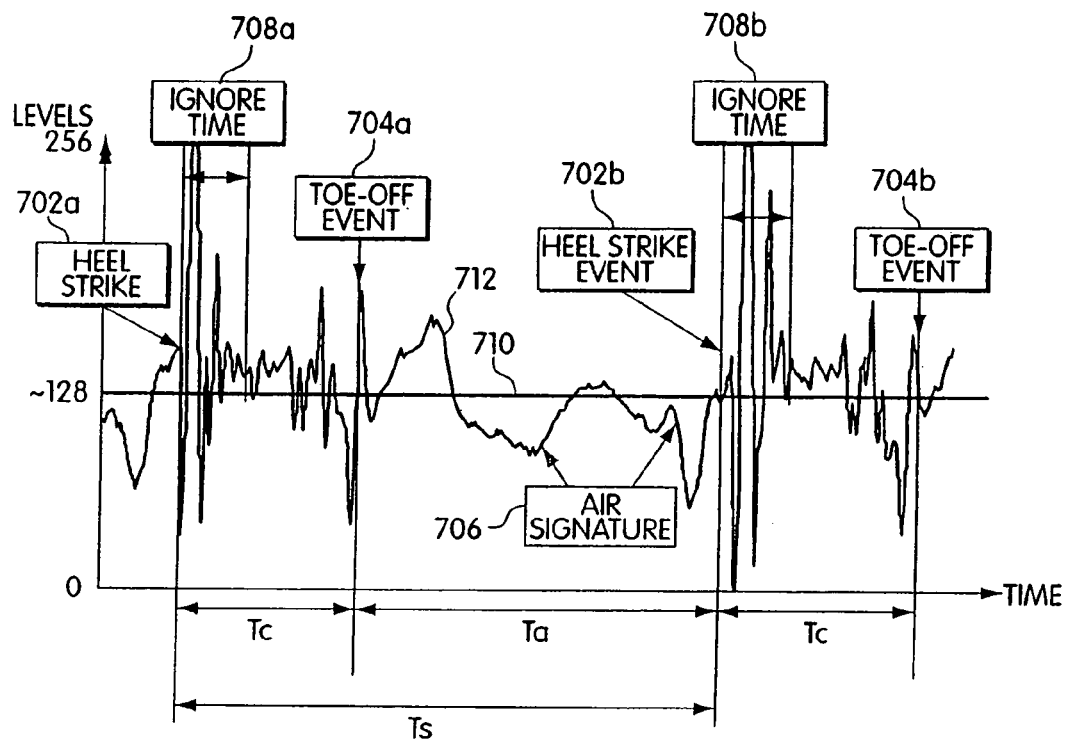
FIG. 7 is a graph showing a typical output signal of a sensor such as that shown in FIGS. 4-6 and the various characteristics of the signal that may be monitored according to one embodiment of the invention.

FIG. 7 shows an example of signals 712 and 710 that may be provided by the sensor 418 of FIG. 6 to the inputs 602 and 604, respectively, of the processor 422 when the user 112 is in locomotion on foot. As shown, the signal 710 may be converted by the processor 422 into a digital value of approximately "128" on the scale of "0" to "256." It should be appreciated that, due to the voltage division performed by the resistors R3 and R4, the voltage at the input 604 may change slightly in response to changes in the voltage at the VCC supply node 610. The level of the sample taken at the input 604 may therefore deviate slightly from the level "128" when such changes in the supply voltage occur.

As also shown in FIG. 7, the signal 712 may fluctuate dynamically between the level "0" and the level "256" in response to movement of the user's foot 114 that occur when the user is walking or running. When the level of the signal 712 is greater than the level of the signal 710, this indicates that the accelerometer is sensing a positive acceleration along the acceleration sensing axis 110, and when the level of the signal 712 is lower than the level of the signal 710, this indicates that the accelerometer 502 is sensing a negative acceleration along the acceleration axis 110.

In accordance with various aspects of the present invention, the signals 710 and 712 generated during strides taken by the user 112 may be analyzed, and particular characteristics of the signals 710 and 712 may be identified which are indicative of particular occurrences during each footstep. As shown in FIG. 7, for example, the signals 710 and 712 may be analyzed: (1) to identify occasions when the user's toe first leaves the surface 108 after having been in contact with the ground during a footstep (e.g., "toe-off events" 704a and 704b), and (2) to identify occasions when the user's heel first impacts the ground after having been airborne (e.g., "heel-strike events" 702a and 702b). When the user 112 is wearing shoes, the term "toe," as used herein, refers to the front-most portion of the user's shoe that accommodates the user's toes, and the term "heel," as used herein, refers to the rear-most portion of the user's shoe that accommodates the user's heel.

In accordance with one aspect of the invention, the toe-off events 704 may be identified by monitoring the signals 710 and 712 for: (a) characteristics that indicate a toe-off event 704 may have potentially occurred, and (b) characteristics that indicate the foot 114 is definitely airborne (i.e., when no portion of the foot 114 is in contact with the surface 108). The latter characteristics are referred to herein as the signal's "air signature" 706.

One characteristic in the signals 710 and 712 that may be indicative of a "potential" toe-off event is large inflection in the signal 712. Therefore, in one embodiment of the invention, inflections in the signal 712 are monitored to identify and to continuously update the identification of a largest inflection to occur in the signal 712 subsequent to the most recent heel-strike event 702.

As shown in FIG. 7, an air signature 706 of the signal 712 may be identified between each toe-off event 704 and the subsequent heel-strike event 702. The air signature 706 may, for example, be an identified period of relative smoothness in the signal 712. When it is determined that the foot 114 is airborne (e.g., an air signature 706 is identified), the most recently identified potential toe-off event is identified as an "actual" toe-off event 704. An example of a routine that may be performed by the processor 422 to monitor the signals 710 and 712 to identify occurrences of actual toe-off events 704 by looking for potential toe-off events and air signatures 706 in the signals is described below in connection with FIGS. 17-19.

In accordance with another aspect of the invention, heel-strike events 702 may be identified by monitoring the signals 710 and 712 for sudden, sharp inflections following the relatively smooth condition of the signal 712 generated while the foot is airborne. In accordance with one embodiment of the invention, characteristics of the signals 710 and 712 are monitored to determine whether the signals satisfy at least one of a plurality of predetermined criteria consistent with the occurrence of a heel-strike event 702. An example of a routine that may be performed by the processor 422 to monitor the signals 710 and 712 for heel-strike events 702 in this manner is described below in connection with FIGS. 21, and 23-25.

As shown in FIG. 7, the period of a complete footstep of the user 112 (i.e., a step time (Ts)) may be measured between the identified heel-strike events 702 of the user 112 (e.g., between the heel-strike events 702a and 702b). The portion of each measured step time (Ts) during which the user's foot 114 is in contact with the surface 108 (i.e., a foot contact time (Tc)) may be measured between each detected heel-strike event 702 and a subsequently-detected toe-off event 704 (e.g., between the heel-strike 702a and the toe-off 704a). Finally, the portion of each measured step time (Ts) during which the user's foot 114 is airborne (i.e., a foot air time (Ta)) may be measured between each detected toe-off event 704 and a subsequently-detected heel-strike event 702 (e.g., between the toe-off 704a and the heel-strike 702b). Thus, for each complete footstep taken by the user 112, an accurate measurement may be made of each step time (Ts) of the user 112, as well as the portions of that step time (Ts) attributable to foot contact time (Ts) and foot air time (Ta). As discussed in more detail below, this information may be used by the processor 422 or the foot-mounted unit 102 and/or the ARC processor 410 of the wrist-mounted unit 104 to accurately calculate the speed and/or pace of the user 112, the distance traveled by the user 112, the energy expended by the user 112, etc., during the corresponding footstep taken by the user 112.

As used herein, a "complete footstep" means a movement cycle during which the foot of a user 112 begins in a particular position and again returns to that same position. For example, complete footsteps of the user 112 may be measured between consecutive "heel-strike events" (i.e., occasions when the user's heel 120 impacts the surface 108), or between consecutive "toe-off events" (i.e., occasions when the user's toe 122 leaves the surface 108).

After each heel-strike event 702 (e.g., the heel-strike event 702a), we have recognized that the foot 114 of the user 112 will necessarily be on the ground for at least a minimum period of time, and that it is not necessary during this period of time to analyze the signals 710 and 712 to identify potential occurrences of a toe-off event 704. Therefore, as shown in FIG. 7, it is possible to "ignore" the signals during this particular period of time. These periods during which the signals 710 and 712 may be ignored are illustrated in FIG. 7 as "ignore times" 708a and 708b.

In accordance with another aspect of the invention, radio transmissions between the foot-mounted unit 102 and the wrist-mounted unit 104 may be made only during the ignore times 708 because the processor 422 need not be employed to monitor the signals 710 and 712 during these time periods. Similarly, according to another aspect of the invention, calculations involving data accumulated by the foot-mounted unit 102 may be made only during the ignore times 708, thereby consuming processing power only during time periods when the signals 710 and 712 need not be actively analyzed.

It is known that the instantaneous pace ($Pace_{INST}$) of a user 112 in locomotion is linearly related to the foot contact time (Tc) measured during a single footstep ($Tc_{FS}$) of the user 112. In particular, the instantaneous pace of the user 112 may be defined by the equation:

$$Pace_{INST} = Mp * Tc_{FS} + BP, \quad (1)$$

wherein MP and BP are constants representing the slope and Y-intercept points of a graph of Pace vs. Tc, and the symbol "*" is the multiplication operator. In light of this relationship, the average pace of the user during a given time period (PaceAvE) may be calculated by replacing the individual foot contact time ($Tc_{FS}$) in the equation (1) with the average value of several individual foot contact times during the measured time period ($Tc_{AVE}$) above to yield the equation:

$$Pace_{AVE} = MP * Tc_{AVE} + BP \quad (2)$$

As discussed in U.S. Pat. No. 6,018,705, the constants Mp and Bp may be different when the user 112 is running than when the user is walking, and each value of Mp and Bp (for both walking or running) may vary from individual to individual. The relationships between Pace and Tc for walking and running (for either instantaneous or average pace calculations) may be represented by the following two equations:

$$Pace = Mp_W * Tc_W + Bp_W \quad Pace = Mp_R * Tc_R + Bp_R \quad (3)$$

Figure 8:
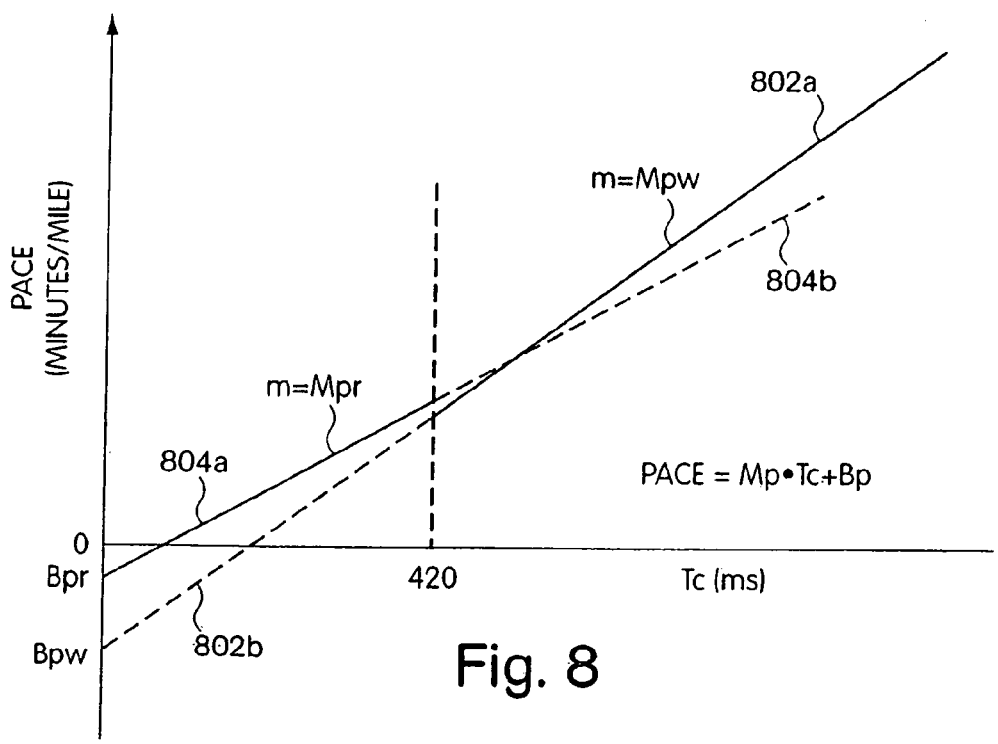
FIG. 8 is a graph showing the linear relationship between the foot contact time (Tc) of a user in locomotion and the pace at which the user is walking or running (Pace)

The graph of FIG. 8 includes lines 802 and 804, which represent the two relationships presented in the equations (3). In particular, the line 802 represents the relationship between a measured foot contact time (Tc) (either a single value or an average value) of the user 112 and the corresponding pace (either instantaneous or average) of the user 112 when the user is walking, and the line 804 represents the relationship between a measured foot contact time (Tc) of the user 112 and the corresponding pace of the user 112 when the user is running. Although linear relationships between foot contact time (Tc) and pace are illustrated in FIG. 8, it should be appreciated that higher-order polynomials may alternatively be used to define these relationships.

We have discovered that it can be determined whether a user, e.g., the user 112, is walking or running during a particular footstep taken by the user 112, simply by comparing the foot contact time (Tc) of the user 112 measured during the footstep with a single threshold value. Therefore, in connection with each measured foot contact time (Tc), it is possible to determine which of the equations represented by the lines 802 and 804 should be used to calculate the user's pace simply by comparing the measured foot contact time (Tc) with this threshold value.

In the example of FIG. 8, the threshold value used to discern whether the user 112 is walking or running is "420" milliseconds (ms). As shown, the lines 802 and 804 are divided into solid portions 802a and 804a and dashed portions 802b and 804b. The solid portions 802a and 804a of the lines 802 and 804, respectively, represent the equations that may be used to calculate the user's pace based upon measured foot contact times. When, for example, a measured foot contact time (Tc) is less than "420" ms, it may be determined that the user 112 is running, and the solid portion 804a of the line 804 may be used to calculate the user's pace. When, on the other hand, a measured foot contact time (Tc) is greater than "420" ms, it may be determined that the user 112 is walking, and the solid portion 802a of the line 802 may be used to calculate the user's pace.

In the example of FIG. 8, the dashed portion 802b of the line 802 is never used to calculate the user's pace while the user 112 is walking because it corresponds to a range of foot contact times that typically do not occur when the user 112 is walking. Similarly, the dashed portion 804b of the line 804 is never used to calculate the user's pace while the user 112 is running because it corresponds to a range of foot contact times that typically do not occur when the user 112 is running.

In another embodiment of the invention, for each given footstep, one of: (1) the ratio of the measured foot contact time (Tc) to the measured step time (Ts) (i.e., Tc/Ts); (2) the ratio of the measured foot air time (Ta) to the measured step time (Ts) (i.e., Ta/Ts); or (3) the ratio of the measured foot contact time (Tc) to the measured foot air time (Ta) (i.e., Tc/Ta), or the inverse value of any such ratios, may be compared with a single threshold value to determine whether the user is running or walking. In one embodiment, the threshold value chosen represents the point when the user's foot is in the air and is on the ground for equal time periods during a complete footstep (i.e., when Tc=Ta). These threshold values may be readily calculated given that, for each complete footstep, Ts=Tc+Ta. If the user's foot is on the ground longer than it is in the air during a complete footstep, it may be determined that the user is walking. Conversely, if it is determined that the user's foot is in the air longer than it is on the ground, it may be determined that the user is running.

In the example shown in FIG. 8, the slopes $Mp_W$ and $Mp_R$ of the lines 802 and 804, respectively, are positive, indicating that longer foot contact times correspond to slower paces and shorter foot contact times correspond to faster paces. Each of the constants $Bp_W$ and $Bp_R$ is negative in the example shown. However, it should be appreciated that, because speed and pace are related according to the equation: Speed=1/Pace, the portions of the lines 802 and 804 that are close to or fall below the "0" pace level are never used, as a pace of "0" corresponds to an infinite speed. In theory, the relationships (for walking and running) between Pace and Tc are non-linear near the origin of the graph of FIG. 8. However, these non-linear portions of the relationships fall outside the possible range of foot contact times for human beings. Within the possible range of foot contact times for human beings, the relationships between Pace and Tc for both walking and running are, in fact, substantially linear.

As mentioned above, in the graph of FIG. 8, the values of the constants $Mp_R$, $Mp_W$, $Bp_R$, and $Bp_W$ may vary from individual to individual. The curves 802 and 804 of FIG. 8 may be optimized for a particular user 112 by having the user 112 run or walk a known twice, at different speeds, while measuring the average foot contact time ($Tc_{AVE}$), as described below, during each of the two outings. By measuring the time taken to run the known distance during each outing, the average pace ($Pace_{AVE}$) of the user may be calculated for each of the two outings. Therefore, using an appropriate one of the equations (3) (depending on whether the user was walking or running during the two outings), two points may be identified on the graph of FIG. 8. Once these two points are identified, if the user 112 walked during both outings, the line 802 may be interpolated through the two points, and, if the user 112 ran during both outings, the line 804 may be interpolated through the two points.

Unfortunately, any error in one or both of these points can significantly impact the accuracy of the calibration performed using this technique. Therefore, in some embodiments, three, four, or more points may be obtained during corresponding outings at different speeds, and a "best fit" line may be plotted through all of the obtained points to yield a more accurate Pace vs. Tc line for walking (if the user 112 walked during all of the outings) or for running (if the user 112 ran during all of the outings).

Figure 9:
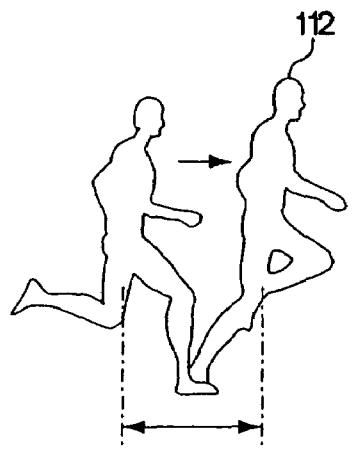
FIG. 9 is an illustration of a user in locomotion on foot that demonstrates the relationship between the foot contact time (Tc) of the user, the speed at which the user is walking or running (Speed), and the step length (Ls) of the user.

As illustrated in FIG. 9, we have recognized that the step length (Ls) of the user 112 (i.e., the distance traversed during each stride taken by one foot of the user) is approximately equal to the foot contact time (Tc) measured during the stride multiplied by the speed at which the user 112 is traveling (Speed), as illustrated by the equation:

$$Ls = Tc*Speed \quad (4)$$

In addition, based upon empirical measurements, we have discovered that the step length (Ls) of the user 112 is also (substantially) linearly related to the speed of the user 112 over a reasonable range of speeds for running or walking, according to the equations:

$$Ls = Mstep_W*Speed + Bstep_W \; Ls = Mstep_R*Speed + Bstep_R \quad (5)$$

Figure 10:
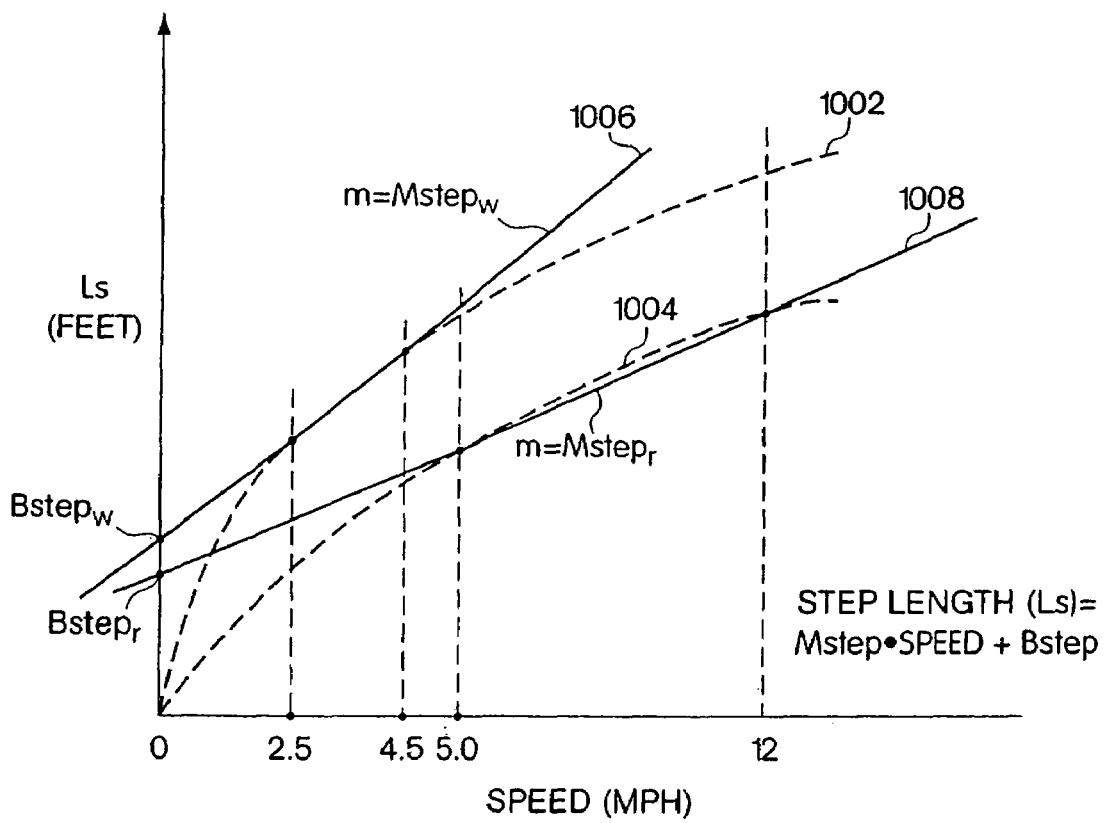
FIG. 10 is a graph illustrating the relationship between a user's step length (Ls) and the speed at which the user is walking or running (Speed)

These substantially linear relationships are illustrated in FIG. 10. Curves 1002 and 1004 in FIG. 10 illustrate typical relationships between the user's step length (Ls) and the walking speed (curve 1002) or running speed (curve 1004) of the user 112. As illustrated by line 1006 in FIG. 10, the relationship between the step length (Ls) of the user 112 and the speed of the user 112 is substantially linear through a reasonable range of walking speeds (e.g., between 2.5 and 4.5 miles per hour (MPH)). Similarly, as illustrated by line 1008 in FIG. 10, the relationship between the step length (Ls) of the user 112 and the speed of the user 112 also is substantially linear through a reasonable range of running speeds (e.g., between 5 and 12 MPH). As shown, the line 1006 has a slope equal to $Mstep_W$ and a Y-intercept equal to $Bstep_W$, and the line 1008 has a slope equal to $Mstep_R$ and a Y-intercept equal to $Bstep_R$.

We have further discovered, again based upon empirical measurements, that the values of the slopes $Mstep_W$ and $Mstep_R$ of the lines 1006 and 1008, respectively, are substantially constant across a large portion of the population, and that the values of the Y-intercepts $Bstep_W$ and $Bstep_R$ for the lines 1006 and 1008, respectively, are generally the only values in equations (5) which vary significantly from person to person. By combining equations (3) and (4) and (5), we have discovered that the values $Mp_W$ and $Mp_R$ in the equations (3) are equal to $1/Bstep_W$ and $1/Bstep_R$, respectively, and that the values $Bp_W$ and $Bp_R$ in the equations (3) are equal to $-Mstep_W/Bstep_W$ and $-Mstep_R/Bstep_R$, respectively. Equation (3) therefore may be rewritten as follows:

$$Pace = 1/Bstep_W*Tc_W - Mstep_W/Bstep_W \; Pace = 1/Bstep_R*Tc_R - Mstep_R/Bstep_R \quad (6)$$

Figure 11:
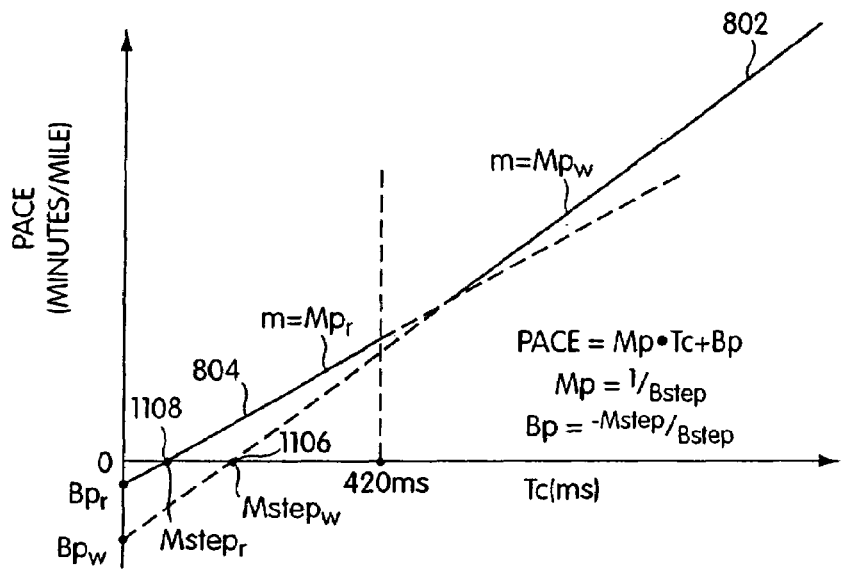
FIG. 11 is a graph showing the linear relationship between the foot contact time (Tc) of a user in locomotion and the pace at which the user is walking or running (Pace) wherein universal pivot points are identified along the foot contact time (Tc) axis of each of the "walking" and "running" lines.

FIG. 11 shows the lines 802 and 804 of the Pace vs. Tc lines of FIG. 8, and also illustrates the above-calculated replacement values of $Mp_W$, $Bp_W$, $Mp_R$, and $Bp_R$ included in the equations (6). By setting the value of Pace in the equations (6) to be equal to "0," and then solving the equations (6) for Tc, it is discovered that the locations of the constant X-intercept points 1106 and 1108 of the lines 802 and 804, respectively, are equal to $Mstep_W$ and $Mstep_R$, respectively. As discussed above, our empirical measurements have revealed that these values are relatively constant across a substantial cross-section of the population. Therefore, the X-intercept points of each of the lines 802 and 804 (i.e., points 1106 and 1108, respectively) do not change significantly from person to person, so that the lines 802 and 804 simply pivot about the respective points 1106 and 1108 on the graph of FIG. 11. Our empirical measurements have revealed that the constant X-intercept value for the "walking" line 802 ($Mstep_W$) is equal to approximately "200" milliseconds (ms), and the constant X-intercept value for the "running" line 804 ($Mstep_R$) is equal to approximately "75" milliseconds (ms).

This discovery is significant because each of the Pace vs. Tc lines 802 and 804 for a particular user 112 may be plotted by locating only a single point on the graph of FIG. 11 when the user 112 is walking or running at a comfortable pace, and interpolating a line between the measured point and the corresponding constant X-intercept point 1106 or 1108.

When a Pace vs. Tc line (such as one of the lines 802 and 804 of FIG. 11) is plotted by identifying two or more points and interpolating a line therebetween, it should be appreciated that the user 112 must walk or run outside of the user's most comfortable pace for walking or running to obtain at least one of these points. The point(s) obtained when the user is not running or walking at the user's most comfortable pace may not be at the optimal location on the Pace vs. Tc graph, and therefore may cause the line interpolated therethrough to be at a less than optimal location. Thus, the single-point calibration scheme discussed above is advantageous not only because the user 112 is required to walk or run a known distance only a single time, but also because the user 112 may walk or run the known distance at the user's most comfortable pace, thereby possibly obtaining more accurate calibration information than if one of the points on the Pace vs. Tc graph was obtained when the user was walking or running at a pace other than the user's most comfortable pace.

As is well known, speed (miles/minute) is related to pace (minutes/mile) according the following equation:

$$Speed = 1/Pace \quad (7)$$

Therefore, in light of the equations (3), speed may be defined according to the following equations:

$$Speed = 1/(Mp_W*Tc_W + Bp_W) \; Speed = 1/(Mp_R*Tc_R + Bp_R) \quad (8)$$

Figure 12:
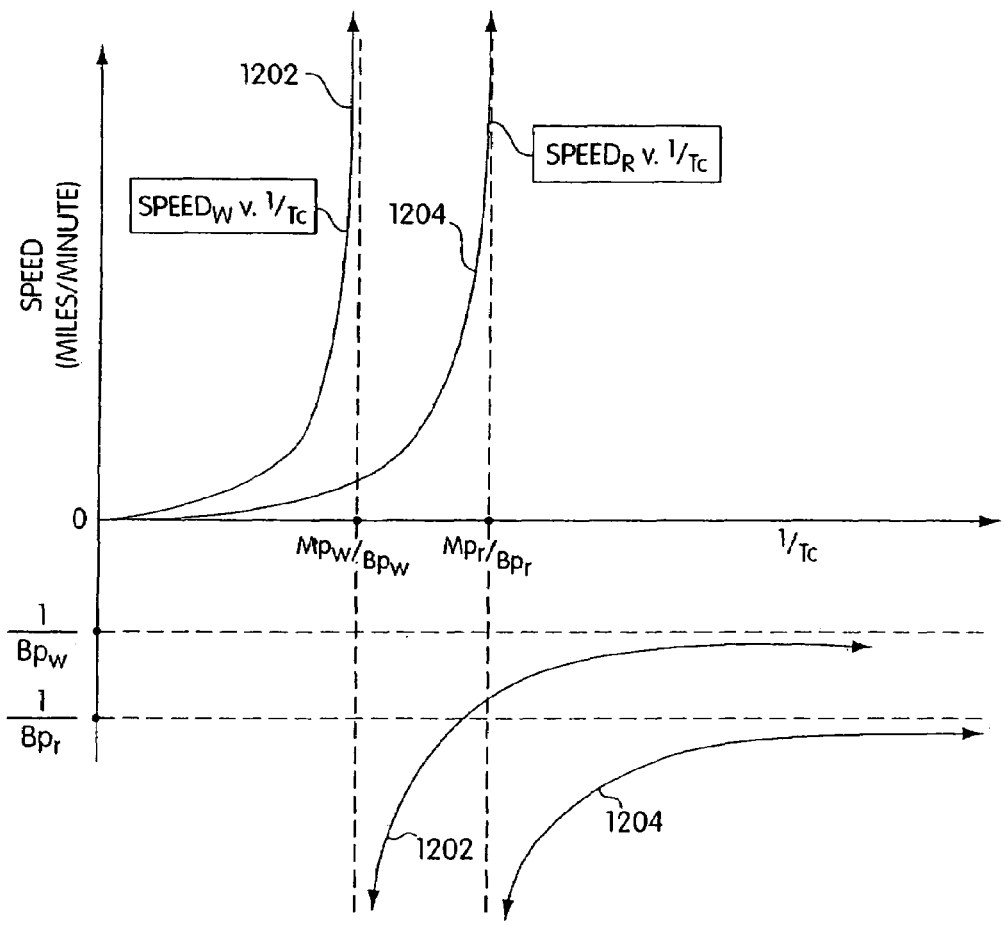
FIG. 12 is a graph showing the relationship between the speed of a user in locomotion (Speed) and the inverse of the foot contact time of the user (1/Tc) as it would appear if the curve of FIG. 11 were mapped onto the coordinate axes of the graph of FIG. 12.

When Speed, defined according to the equations (8), is plotted against $1/Tc$, curves 1202 and 1204 shown in FIG. 12 may be obtained. As shown in FIG. 12, the relationships between Speed and $1/Tc$ while the user 112 is walking (curve 1202) and while the user is running (curve 1204) appear to be substantially non-linear, as compared to the relatively linear relationships between Pace and Tc illustrated in FIGS. 8 and 11.

Figure 13:
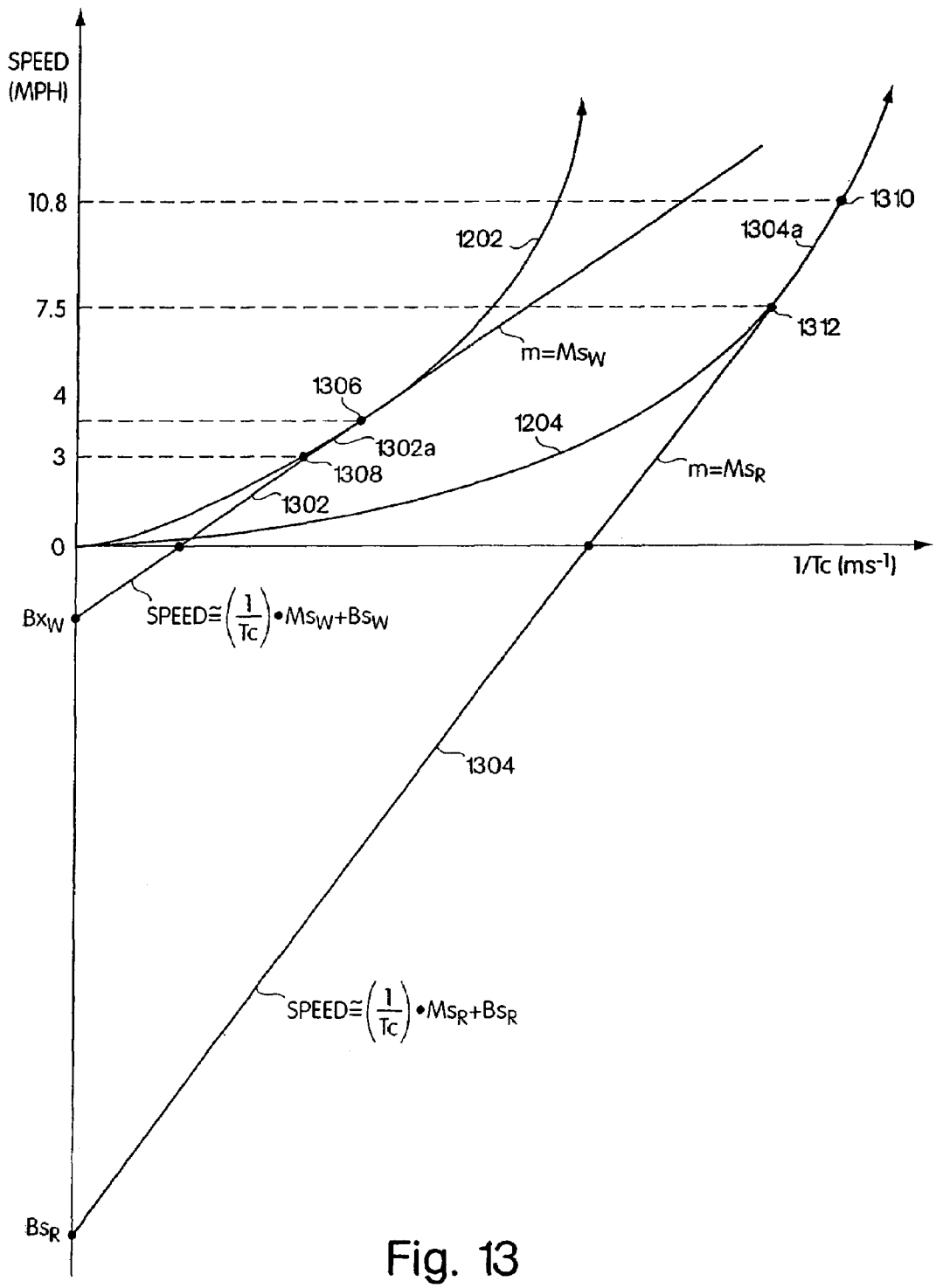
FIG. 13 shows a portion of the graph of FIG. 12 (converted to speed units of miles per hour) and illustrates the substantially linear relationship between the speed of the user in locomotion (Speed) and the inverse of the contact time of the user (1/Tc) within a reasonable range of walking or running speeds.

FIG. 13 illustrates the same relationship as does FIG. 12, but uses the units miles-per-hour (MPH) on the Speed axis, rather than miles-per-minute (i.e., a factor of "60" adjustment). In addition, the graph of FIG. 13 focuses only on the relative portion of the graph of FIG. 12 that corresponds to reasonable ranges of walking and running speeds for a human being. As shown, FIG. 13 illustrates that, within a reasonable range of walking speeds (e.g., between "3" and "4" MPH), the curve 1202 is substantially linear. Similarly, between a reasonable range of running speeds (e.g., between "7.5" and "10.8" MPH), the curve 1204 also is substantially linear. Therefore, in accordance with an aspect of the present invention, a line 1302, which passes through the aforementioned substantially linear portion of the curve 1202, may used to define an approximation of the relationship between Speed and 1/Tc when the user 112 is walking, and a line 1304, which passes through the aforementioned substantially linear portion of the curve 1204, may be used to define an approximation of the relationship between Speed and 1/Tc when the user 112 is running. As shown, the lines 1302 and 1304 may be defined using the equations:

$$\text{Speed}=(1/Tc)*Ms_W+Bs_W \quad \text{Speed}=(1/Tc)*Ms_R+Bs_R \quad (9)$$

wherein $Ms_W$ and $Ms_R$ are constants representing the slopes of the lines 1302 and 1304, respectively, and $Bs_W$ and $Bs_R$ are constants representing the Y-intercepts of the lines 1302 and 1304, respectively. Although linear relationships between the inverse of foot contact time (1/Tc) and speed are illustrated in FIG. 13, it should be appreciated that higher-order polynomials may alternatively be used to define these relationships.

Unfortunately, because the universal pivot points 1106 and 1108 of FIG. 11 are defined at a pace equal to "0," such pivot points cannot be identified on the graph of FIG. 13 because, as is evident from the equation (7), a pace of "0" corresponds to an infinite speed. When a single point calibration scheme is used wherein a single point on the graph of FIG. 11 is identified for either walking or running and a line is interpolated between the identified point and one of the universal pivot points 1106 and 1108, however, it is possible to pick a few (at least two) points from the interpolated "walking" line 802 or the interpolated "running" line 804 of FIG. 11 that fall within a reasonable range of paces for running or walking. These selected points may then be transferred onto the graph of FIG. 13, and a line may be interpolated between the transferred points to obtain a corresponding one of the lines 1302 and 1304 shown in FIG. 13.

As discussed above, the foot-mounted unit 102 and the wrist-mounted unit 104 may communicate using either a one-way or a two-way communication link. When a two-way communication link is employed, any of the calibration values discussed herein may be calculated (based upon user inputs regarding the starting and stopping of a calibration procedure) using the wrist-mounted unit 104, and may be subsequently communicated from the wrist-mounted unit 104 to the foot-mounted unit 102. Alternatively, commands instructing the foot-mounted unit 102 to start and stop a calibration procedure at appropriate times may be communicated from the wrist-mounted unit 104 to the foot-mounted unit 102. In either case, it is possible to store calibration values in the foot-mounted unit 102 based upon user input to the wrist-mounted unit (e.g., using one or more of the buttons 306).

Of course, it is also possible for a user to input calibration commands directly to the foot-mounted unit 102, and thereby cause such values to be calculated by and stored in the foot-mounted unit 102 without any intervention by the wrist-mounted unit 104. We recognize, however, that it may be more convenient and yield more accurate calibration results for the user 112 to input such commands to the wrist-mounted unit 104, rather than the foot-mounted unit 102. This is true because the user is able to input commands to the wrist-mounted unit 104 while in locomotion, as opposed to having to stop walking or running and bend over to input such commands to the foot-mounted unit 102.

Regardless of their origin, once appropriate calibration value obtained, the processor 422 of the foot-mounted unit 102, for example, may use these calibration values (as explained below) to perform calculations involving the user's instantaneous and average pace and/or speed, as well as calculations involving the distance traveled by the user during a given outing. The results of these calculations then may be displayed on the foot-mounted unit 102 and/or transmitted to the wrist-mounted unit 104 for display to the user 112.

In alternative embodiments of the invention, the ARC processor 410 of the wrist-mounted unit 104, or another processor distinct from both the foot-mounted unit 102 and the wrist-mounted unit 104, may instead perform these calculations. For example, each measured foot contact time (Tc) and step time (Ts) may be transmitted from the foot-mounted unit 102 to the wrist-mounted unit 104 or another device, and the ARC processor 410 the wrist-mounted unit 104 or a processor in the other device may perform all of the calculations described herein based these values. In fact, in some embodiments, the signal from the sensor 418 may be the only information that is transmitted (wirelessly) from the foot-mounted unit 102 to the wrist-mounted unit 104 or another device, and the wrist-mounted unit 104 or the other device may itself perform the analysis of the sensor signal during which foot contact times, etc., are measured, as well as performing all or some of the other calculations described herein involving such measured values. In any of these alternative embodiments, appropriate calibration values may be both calculated by and stored directly in the wrist-mounted unit 104.

The user 112 may instruct the foot-mounted unit 102 to start and stop performing such calculations either by providing appropriate inputs directly to the foot-mounted unit 102 (e.g., using the button 204 or one or more other buttons on the foot-mounted unit 102), or by providing appropriate inputs to the wrist-mounted unit 104 (e.g., by depressing one or more of the buttons 306), which then can transmit the instructions to the foot-mounted unit 102. Examples of how the above-mentioned calculations may be performed by the processor 422 will now be provided, recognizing, of course, that the invention is not limited to embodiments wherein the processor 422 is the entity that performs these calculations.

While the user 112 is walking or running during an outing, for each complete footstep by the user, both the step time (Ts) of the footstep and the portion of that step time (Ts) constituting the foot contact time (Tc) of the footstep may be measured as described herein. As discussed above in connection with FIG. 8, each measured foot contact time (Tc) may be compared with a threshold value (e.g., 420 milliseconds), and, based upon that comparison, may be categorized as a "walking" foot contact time ($Tc_W$) or as a "running" foot contact time ($Tc_R$). Each step time (Ts) may also be placed into the same category as the foot contact time (Tc) with which it is associated. That is, each step time (Ts) associated with a "walking" foot contact time ($Tc_W$) may be categorized as "walking" step time ($Ts_W$), and each step time (Ts) associated with a "running" foot contact time ($Tc_R$) may be categorized as "running" step time ($Ts_R$).

By accumulating running totals of measured foot contact times for both walking and running (i.e., $\Sigma Tc_W$ and $\Sigma Tc_R$), and also keeping track of the number of walking and running foot contact times so accumulated (i.e., $Tc_{WNUM}$ and $Tc_{RSUM}$), an average "walking" foot contact time ($Tc_{W/aVE}$) may be calculated by dividing the value of $\Sigma Tc_W$ by the value of $Tc_{WNUM}$ (i.e., $Tc_{W/aVE} = \Sigma Tc_W / Tc_{WNUM}$), and an average "running" foot contact time ($Tc_{RAVE}$) may be calculated by dividing the value of $\Sigma Tc_R$ by the value of $Tc_{RNUM}$ (i.e., $Tc_{R/aVE} = \Sigma Tc_R / Tc_{RNUM}$). Based upon these values, the average "walking" and/or "running" pace (Pace$_{WAVE}$ and/or Pace$_{RAVE}$) during an outing may be calculated by simply plugging the current average value of $Tc_{WAVE}$ and/or the current average value of $Tc_{RAVE}$ into one or both of the equations (3) above. Similarly, the instantaneous pace as a result of the last measured foot contact time (Tc), or as a result of an average of the last several (e.g., four) measured foot contact times, may be calculated by plugging the current or average value of $Tc_W$ and/or the current or average value of $Tc_R$ into one or both of the equations (3) above.

In addition, using the well-known relationship: Distance=Time/Pace, the distance traveled during each complete footstep may be calculated by plugging the measured foot contact time (i.e., $Tc_W$ or $Tc_R$) for the footstep into an appropriate one of the equations (3) to yield the pace for that footstep, and then dividing the measured step time (Ts) for the footstep by the pace calculated for the same. The total distance traveled by the user 112 therefore can be calculated, regardless of whether the user 112 is walking and/or running during the outing, by accumulating a running total of such per-footstep distances.

Alternatively, in addition to calculating the values of $Tc_{WAVE}$ and $Tc_{RAVE}$, as discussed above, cumulative totals of the values of $Ts_W$ and $Ts_R$ (i.e., $\Sigma Ts_W$ and $\Sigma Ts_R$) may be maintained in memory. Based upon these values, "walking" and "running" distance values may be calculated using the following equations, which represent a combination of the equations (3) with the relationship: Distance=Time/Pace:

$$\text{Distance}_W = \Sigma Ts_W / (Mp_W * Tc_{WAVE} + Bp_W)$$
$$\text{Distance}_R = \Sigma Ts_R / (Mp_R * Tc_{RAVE} + Bp_R) \quad (10)$$

Therefore, the total distance traveled by the user during the outing (regardless of whether the user is walking or running) may be calculated by adding together both of the equations (10), thereby yielding the equation:

$$\text{Distance}_{TOTAL} = \Sigma Ts_W / (Mp_W * Tc_{WAVE} + Bp_W) + \Sigma Ts_R / (Mp_R * Tc_{RAVE} + Bp_R) \quad (11)$$

As mentioned above, after performing these calculations, the foot-mounted unit may periodically transmit information, such as distance traveled, average pace, instantaneous pace, etc., to the wrist-mounted unit 104 for display to the user 112. Alternatively, the foot-mounted unit 102 may itself display some or all of the desired information.

With regard to the equations discussed herein involving pace, it should be appreciated that, in light of the relationship: Speed=1/Pace, similar equations involving speed, rather than pace, may alternatively be used to calculate the various performance parameters, including the parameter Speed itself.

As is well-known, the distance traveled by a user during a given time interval may be calculated by the following equation:

$$\text{Distance} = \text{Speed} * \text{Time} \quad (12)$$

Therefore, by combining the equations (9) and (12), for each complete footstep taken by the user 112 (i.e., during each step time (Ts)), the distance traveled by the user 112 during that footstep may be determined using the equations:

$$\text{Distance} = (Ts/Tc) * Ms_W + Ts * Bs_W \quad \text{Distance} = (Ts/Tc) * Ms_R + Ts * Bs_R \quad (13)$$

As discussed above, the one of the equations (13) that is used to calculate the distance traveled by the user during a given footstep may be determined based upon a comparison of the measured foot contact time (Tc) with the threshold value discussed above (e.g., "420" ms) in connection with FIG. 8. Therefore, to calculate the total distance traveled by the user 112 during a particular outing, the values Tc and Ts may be monitored during each footstep taken by the user 112, and each monitored Tc and Ts value may be identified as having been measured either when the user 112 was walking or when user 112 was running. After having been identified as either "walking" Tc and Ts values ($Tc_W$ and $Ts_W$) or "running" Tc and Ts values ($Tc_R$ and $Ts_R$), a running total of each of the values $Tc_W$, $Ts_W$, $Tc_R$, and $Ts_R$ obtained during the outing may be stored, and the total distances traveled by the user while running and walking may be calculated using the equations:

$$\text{Total Walking Distance} = \Sigma (Ts_W / Tc_W) * Ms_W + \Sigma Ts_R * Bs_W \quad (14)$$

$$\text{Total Running Distance} = \Sigma (Ts_R / Tc_R) * Ms_R + \Sigma Ts_R * Bs_R \quad (15)$$

Therefore, the total distance traveled by the user during the outing (regardless of whether the user is walking or running) may be calculated by adding together the equations (14) and (15), thereby yielding the equation:

$$\text{Total Distance} = \Sigma (Ts_W / Tc_W) * Ms_W + \Sigma Ts_R * Bs_W + \Sigma (Ts_R / Tc_R) * Ms_R + \Sigma Ts_R * Bs_R \quad (16)$$

Using these equations, the values $\Sigma(Ts_W/Tc_W)$, $\Sigma Ts_W$, $\Sigma(TsR/Tc_R)$, and $\Sigma Ts_R$ ("the Tc/Ts and Ts sum values") may be cumulatively updated by the foot-mounted unit 102 as the user 112 is walking or running, and the Tc/Ts and Ts sum values accumulated by the foot-mounted unit 102 may be periodically transmitted (e.g., once every millisecond) to the wrist-mounted unit 104. When the wrist-mounted unit 104 receives a transmission from the foot-mounted unit 102 including updated Tc/Ts and Ts sum values, these values may be combined with the calibration values $Ms_W$, $Bs_W$, $Ms_R$ and $Bs_R$ in accordance with equation (16) to calculate the total distance traveled by the user 112 during the outing for which the Tc/Ts and Ts sum values were accumulated.

When the user provides an indication to the wrist-mounted unit 104 that the user 112 wants the wrist-mounted unit to begin measuring a total distance traveled by the user 112 (e.g., by depressing one of the buttons 306), the wrist mounted unit 104 may, for example, record the values of the Tc/Ts and Ts sum values last received from the foot-mounted unit 102 as "starting values." The wrist-mounted unit may then subtract the recorded starting values from any updated Tc/Ts and Ts sum values later received from the foot-mounted unit 102 to obtain an accurate measurement of the Tc/Ts and Ts sum values accumulated that have been accumulated since the user instructed to the wrist-mounted unit 102 to begin a total distance measurement.

Alternatively, each measured foot contact time (Tc) and step time (Ts) may be transmitted from the foot-mounted unit 102 to the wrist-mounted unit 104 or another device, and the wrist-mounted unit 104 or the other device may perform all of the calculations described herein based these values. In fact, in some embodiments, the signal from the sensor 418 may be the only information that is transmitted (wirelessly) from the foot-mounted unit 102 to the wrist-mounted unit 104 or another device, and the wrist-mounted unit 104 or the other device may itself perform the analysis of the sensor signal during which foot contact times, etc., are measured, as well as performing all or some of the other calculations described herein involving such measured values.

In light of the universal pivot points 1106 and 1108 identified in the graph of FIG. 11 for the lines 802 and 804, respectively, we have recognized that, for each of the two lines 802 and 804, each individual user may be assigned a single calibration "value" that identifies the location of that line. For example, each user may be assigned a first calibration value between "1" and "200" that identifies a corresponding angular orientation of the "running line" 802 about the pivot point 1106, and may be assigned a second calibration value between "1" and "200" that identifies a corresponding angular orientation of the "walking line" 804 about the pivot point 1108.

In one embodiment, a "baseline" value of a foot contact time (Tc) is selected, and an equation including the single calibration value (e.g., a number between "1" and "200") as a variable is used to define the pace that corresponds to the baseline foot contact time (Tc). Thus, each change in the value of the single calibration value causes a corresponding change in the value of the pace associated with the baseline foot contact time (Tc). In this manner, a point is defined on the Pace vs. Tc graph of FIG. 11 through which an appropriate one of the lines 802 and 804 may be interpolated, with the other point through which the line is interpolated being one of the universal pivot points 1106 and 1108. In one illustrative embodiment, this relationship is defined (for each of the lines 802 and 804) using the following equation:

$$Pace_{TcBASELINE} = m_{CalVal} * CalVal_P + b_{CalVal} \quad (17)$$

Wherein $CalVal_P$ is the single calibration value (e.g., a number between "0" and "200") and $m_{CalVal}$ and $b_{CalVal}$ are constants defining, respectively, the slope and Y-intercept of the relationship between $Pace_{TcBASELINE}$ and $CalVal_P$. It should be appreciated that the relationship between the single calibration value and pace, for the baseline foot contact time (Tc), may alternatively be non-linear, and the invention is not limited to a linear relationship such as that shown.

In one embodiment of the invention, after a value of $CalVal_P$ is set initially (for either running or walking), this value can later be optimized whenever the user runs or walks a reported distance (e.g., a five mile race), and obtains a measured distance for the race (e.g., "3.1" miles) using the foot-mounted unit 102 and/or wrist-mounted unit 104. This optimization may be achieved in response to the user inputting only the reported distance and the measured distance, and may be performed by one or more of the foot-mounted unit 102, the wrist-mounted unit 104, the computer 428, and the network server 442, as follows.

Referring to FIG. 11, the user may run or walk a reported distance (e.g., five miles), while the foot-mounted unit 102 and/or the wrist-mounted unit 104 calculates a measured distance (e.g., "3.1 miles") based upon measured foot contact times and the initial value of $CalVal_P$. Next, using the line corresponding to the initial value of $CalVal_P$, the value of Tc corresponding to an arbitrarily-picked value of Pace (e.g., seven minutes/mile) may be determined. In addition, the arbitrarily-picked value of Pace (e.g., seven minutes/mile) may be multiplied by the reported distance (e.g., five miles) to obtain a time value (e.g., "17.5" minutes). Next, this time value (e.g., "17.5" minutes) may be divided by the measured distance (e.g., 3.1 miles), which was calculated using the line corresponding to the initial value of $CalVal_P$, to obtain a calculated value of Pace (e.g., "5.64 minutes/mile). A point on the graph of FIG. 11 may then be identified having a "Pace" coordinate corresponding to the calculated value of Pace (e.g., "5.64" minutes/mile) and a "Tc" coordinate corresponding to the value of Tc corresponding to the arbitrary pace (e.g., seven minutes/mile) identified above. Finally, a new line may be interpolated between this identified point and the universal pivot point discussed above, which line represents a newly-calibrated Pace vs. Tc line for the user. Based upon the position of this line, a new value of $CalVal_P$ may be determined and may be stored in memory for the user. This new value of $CalVal_P$, and the line corresponding thereto, may then be used for future measurements by the foot-mounted unit 102 and/or the wrist-mounted unit 104. This procedure may be used to optimize either the walking line 802 or the running line 804 of FIG. 1.

It should be appreciated that this technique can likewise be performed in other situations wherein a set of lines is known for which a single calibration value and/or a single point defines each line in the set. For example, the above-described technique may also be employed in connection with the set of lines identifying the relationship between Speed and 1/Tc, explained below in connection with FIG. 13, because a single calibration value can be used therein to define each line in that set of lines.

As discussed above, each line in the graph of FIG. 11 can be translated into a corresponding line in the graphs of FIG. 13 (e.g., by selecting a few reasonable values of Tc and Pace, calculating values of 1/Tc and Speed based thereupon, plotting points corresponding to the calculated values, and interpolating a line between the points so plotted). Therefore, because a single calibration point can identify the position of each of the curves 802 and 804 in the graph of FIG. 11, a single calibration point can also be used to identify the position of each of the curves 1302 and 1304 in the graph of FIG. 13. In this regard, it should be understood that, while each single calibration "value" used in connection with the graph of FIG. 11 identifies a corresponding degree of rotation of one of the lines 802 and 804 about its pivot point, each of the "single" calibration values used in connection with the graph of FIG. 13 identifies both a corresponding degree of rotation and a corresponding degree of translation of one of the lines 1302 and 1304 with respect to the Speed and 1/Tc axes of the graph.

Based upon empirical measurements of the relationships between Tc and Pace and 1/Tc and Speed for a large number of users, we have discovered universal relationships between the calibration constants $Mp_R$ and $Bs_R$ and between the calibration constants $Mp_W$ and $Bs_W$ of the equations (3) and (11), respectively, that have enabled us to derive respective equations (each including a single, user-specific constant) that identify corresponding rotational and translational positions of the curves 1302 and 1304 in the graph of FIG. 13. Therefore, using these equations, each user may simply be assigned a first calibration constant that defines that user's "walking curve" 1302 in the graph of FIG. 13 and second calibration constant that defines that user's "running curve" 1304. This may compared to the alternative technique of using two separate calibration constants (i.e., the calibration constants $Ms_W$ and $Bs_W$ or $Ms_R$ and $Bs_R$ of equations (9)) to define each of the lines 1302 and 1304.

The discovered relationships between the constants Mp and Bs from the equations (3) and (11), respectively, are identified by the following equations:

$$Mp_W = C1 * Bs_W \quad Mp_R = C2 * Bs_R \quad (18)$$

wherein C1 and C2 are universal constants. The constants C1 and C2 are referred to herein as the "Darley constants," named after their discoverer, Jesse Darley, of Watertown, Mass. When the units used in the graphs of FIGS. 11 and 13 are employed, we have discovered that the Darley constant C1 is equal to "−1" and that the Darley constant "C2" is equal to "−1/1.4062" (which can be approximated by the fraction "−32/45").

Because the locations of the universal pivot points 1106 and 1108 (i.e., the Tc values when pace is equal to "0") are known, the equations (3) can be simplified to:

$$Bp_W = -PP_W * Mp_W \; Bp_R = -PP_R * Mp_R \quad (19)$$

wherein $PP_W$ is equal to the Tc value at the pivot point 1106 of the line 802 (i.e., $Mstep_W$), and $PP_R$ is equal to the Tc value at the pivot point 1108 of the line 804 (i.e., $Mstep_R$). In the units used in the graph of FIG. 11, the values of $PP_W$ and $PP_R$ are "200" and "75," respectively.

As shown below, the equations (18) and (19) may be combined to yield the equations:

$$Bp_W = -PP_W * C1 * Bs_W \; Bp_R = -PP_R * C2 * Bs_R \quad (20)$$

The equations (3) and (11) may be solved for Tc and Ms, respectively, to yield the equations:

$$Tc = (Pace - Bp_W)/Mp_W \; Tc = (Pace - Bp_R)/Mp_R \quad (21)$$

$$Ms_W = Tc*(Speed - Bs_W) \; Ms_R = Tc*(Speed - Bs_R) \quad (22)$$

The equations (19) and (20) then may be combined to yield the equations:

$$Ms_W = (Speed_{EPW} - Bs_W)*(Pace_{EPW} - Bp_W)/Mp_W$$

$$Ms_R = (Speed_{EPR} - Bs_R)*(Pace_{EPR} - Bp_R)/Mp_R \quad (23)$$

wherein $Speed_{EPW}$ and $Pace_{EPW}$ represent, respectively, the speed at one of the "end points" 1306 and 1308 of the line segment 1302a of the "walking" line 1302 and the pace (i.e., 1/Speed) corresponding therewith, and $Speed_{EPR}$ and $Pace_{EPR}$ represent, respectively, the speed at one of the "end points" 1310 and 1312 of the line segment 1304a of the "running" line 1304 and the pace (i.e., 1/Speed) corresponding therewith. The speed with which each of the endpoints is associated therefore corresponds precisely with a pace on one of the lines 802 and 804 in the graph of FIG. 11, whereas the speeds with which central portions of the line segments 1302a and 1304a are associated may not correspond precisely with paces on the lines 802 and 804 in the graph of FIG. 11 because of the slight bend in the curves 1202 and 1204 between the endpoints of the line segments 1302a and 1304a, respectively.

With the units used in FIGS. 11 and 13, the endpoint paces ($Pace_{EPW}$) corresponding to the endpoint speeds ($Speed_{EPW}$) of the line segment 1302a of "4" and "4.5" MPH are "15" and "13.333" minutes/mile, respectively, and the endpoint paces ($Pace_{EPR}$) corresponding to the endpoint speeds ($Speed_{EPR}$) of the line segment 1304a of "7.5" and "9" MPH are "8" and "6.666" minutes/mile, respectively.

As shown below, the equations (18), (20), and (23) may be combined to yield the following values for $Ms_W$ and $Ms_R$:

$$Ms_W = (Speed_{EPW} - Bs_W)*(Pace_{EPW} + PP_W * C1 * Bs_W)/(C1*Bs_W)$$

$$Ms_R = (Speed_{EPR} - Bs_R)*(Pace_{EPR} + PP_R * C2 * Bs_R)/(C2*Bs_R) \quad (24)$$

Thus, in the equations (24), the value of each of the constants in the equations (11) (i.e., $Ms_W$ or $Ms_R$) is defined in terms of the other constant (i.e., $Bs_W$ or $Bs_R$) in the same equation. The equations (24) therefore can be combined with the equations (11) to yield the following equations for speed that depend on only one user-specific constant (i.e., $Bs_W$ or $Bs_R$):

$$Speed = (1/Tc)*(Speed_{EPW} - Bs_W)*(Pace_{EPW} + PP_W*C1*Bs_W)/(C1*Bs_W)/(C1*Bs_W) + Bs_W$$

$$Speed = (1/Tc)*(Speed_{EPR} - Bs_R)*(Pace_{EPR} + PP_R*C2*Bs_R)/(C2*Bs_R) + Bs_R \quad (25)$$

Finally, the equations (12) and (25), may be combined, in a manner similar to that by which the equations (11) and (12) above were combined to yield equation (17), to yield the following equation:

$$Total\;Distance = \Sigma(Ts_W/Tc_W)*(Speed_{EPW} - Bs_W)*(Pace_{EPW} + PP_W*C1*Bs_W)/(C1*Bs_W) + \Sigma Ts_W*Bs_W + \Sigma(Ts_R/Tc_R)*(Speed_{EPR} - Bs_R)*(Pace_{EPR} + PP_R*C2*Bs_R)/(C2*Bs_R) + \Sigma Ts_R*Bs_R \quad (26)$$

As mentioned above, when the unit shown in the graphs of FIGS. 9 and 11 are used in the equation (26), the values of the Darley constants C1 and C2 may be "−1" and "−32/45," respectively, the values of the constants $PP_W$ and $PP_R$ may be "200" and "75" ms, respectively, the constants $Speed_{EPW}$ and $Pace_{EPW}$ may be "4" MPH and "15" minutes/mile (or and "4.5" MPH and "13.333" minutes/mile), respectively, and the constants $Speed_{EPR}$ and $Pace_{EPR}$ may be "7.5" MPH and "9" minutes/mile (or and "9" MPH and "6.666" minutes/mile), respectively. Thus, the only unknowns in the equation (26) are the accumulated values of $\Sigma Ts_W$, $\Sigma Tc_W$, $\Sigma Ts_R$, and $\Sigma Tc_R$, and the user-specific constants $Bs_W$ and $Bs_R$.

When the equation (26) is used and the user 112 wishes to set the value of the user-specific constants $Bs_W$, the user can simply walk a known distance (e.g., "¼" of a mile) while permitting the values $\Sigma Ts_W$, $\Sigma Tc_W$, $\Sigma Ts_R$, and $\Sigma Tc_R$ to accumulate during the time period taken to walk the distance. Because the values $\Sigma Ts_R$ and $\Sigma Tc_R$ will be zero when the user is walking, the constant $Bs_R$ drops out of the equation, and the equation (26) can be solved for the value of $Bs_W$. This value of $Bs_W$ can then be stored and used in the equation (26) to calculate distance traveled by the user 112 during normal operation. Alternatively, the user can select a calibration mode specifically for walking, and only the portion of the equation (26) relating to walking can be used to calculate the value of $Bs_W$ after the user walks a known distance.

Similarly, when the equation (26) is used and the user 112 wishes to set the value of the user-specific constants $Bs_R$, the user can simply run a known distance (e.g., "¼" of a mile) while permitting the values $\Sigma Ts_W$, $\Sigma Tc_W$, $\Sigma Ts_R$, and $\Sigma Tc_R$ to accumulate during the time period taken to walk the distance. Because the values $\Sigma Ts_W$ and $\Sigma Tc_W$ will be zero when the user is running, the constant $Bs_W$ drops out of the equation, and the equation (26) can be solved for the value of $Bs_R$. As with the value of $Bs_W$, this value of $Bs_R$ can then be stored and used in the equation (26) to calculate distance traveled by the user 112 during normal operation. Alternatively, similar to the walking calibration discussed above, the user can select a calibration mode specifically for running, and only the portion of the equation (26) relating to running can be used to calculate the value of $Bs_R$ after the user runs a known distance.

Regardless of the equation(s) used to determine the user's pace or speed, and regardless of the calibration technique(s) used to optimize those equation(s), in one illustrative embodiment of the invention, as discussed above in connection with FIG. 4, user-specific information (such as one or more calibration constants) may be stored somewhere in the system for each of several users (e.g., family members or members of a track team), and such information be selectively accessed and used in response to the user entering his or her name, user ID or other identifier into the wrist-mounted unit 104 or elsewhere. In addition, to the extent a user's choice of running or walking shoe or other accessory (e.g., a knee or ankle brace) has any effect on the proper selection of his or her calibration constant(s), each user may also input another code to indicate the user's choice. In response to the entry of such data, the wrist-mounted unit 104 (or other device) may then access and use previously-stored calibration information corresponding to the user's choice. In addition, the entry of such information may also permit the appropriate device to place accumulated information (e.g., distance traveled) into a log corresponding to the choice. For example, data such as total distance traveled may be separately logged for each pair or shoes worn by the user.

Figure 14:
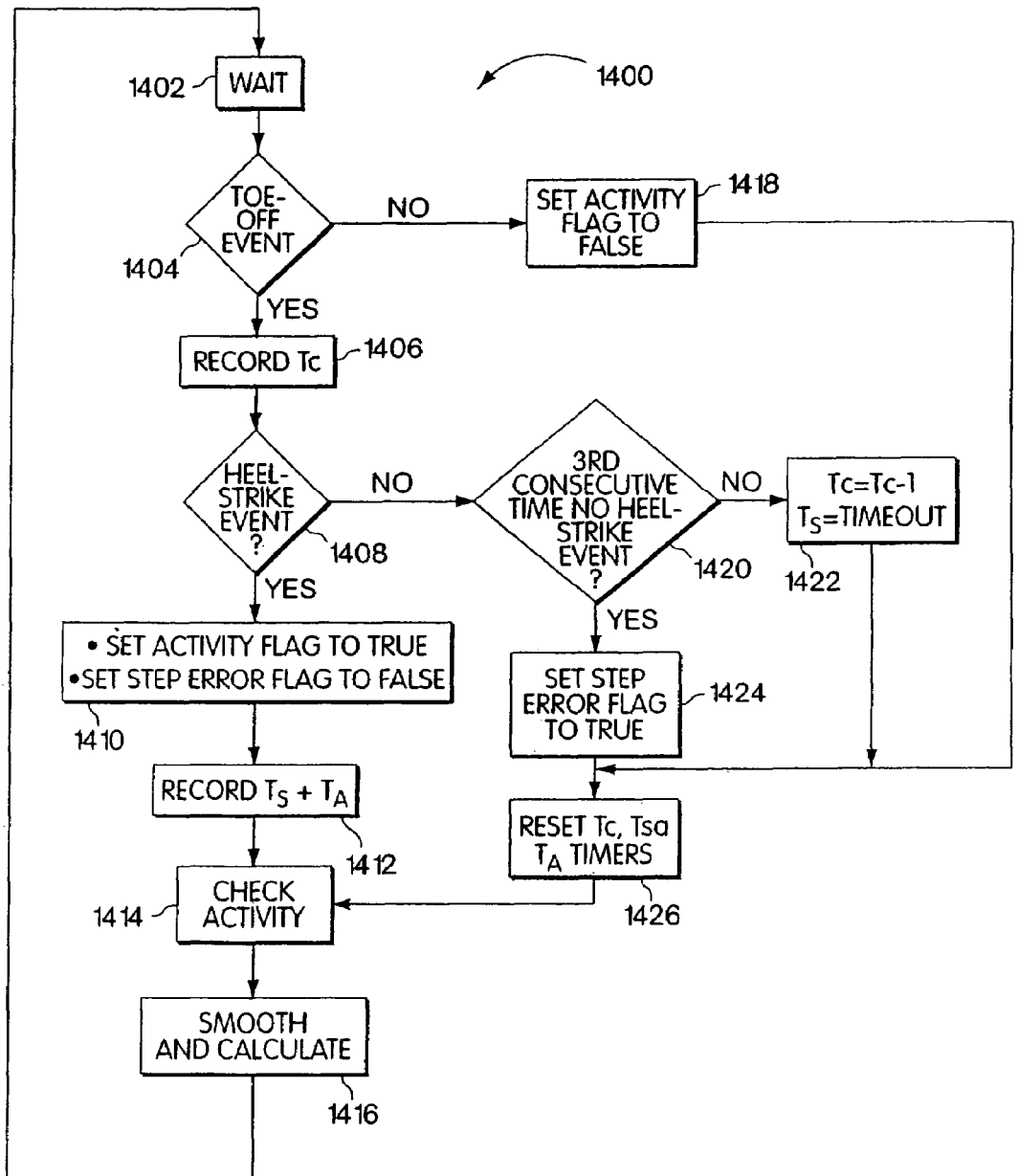
FIG. 14 is a flow diagram illustrating an example implementation of a primary routine that may be performed by the processor of the foot-mounted unit shown in FIGS. 4 and 6 in accordance with one embodiment of the present invention.

FIG. 14 shows and illustrative example of a primary routine 1400 that may be performed by the processor 422 of the foot-mounted unit 102 (FIG. 4) in accordance with one embodiment of the present invention. The processor 422 may, for example, execute a plurality of instructions stored in the memory 424 or another computer-readable medium to perform the various method steps and routines of the primary routine 1400. Alternatively, of course, the primary routine 1400 can be implemented using dedicated hardware or firmware, or any combination of hardware, firmware and software capable of achieving a similar result.

With regard to the illustrative routine 1400 and the constituent routines thereof, it should be appreciated that the precise order of the method steps and routines is not critical, and that the invention is not limited to embodiments that perform method steps and routines precisely in the order shown. Additionally, it should be appreciated that the method steps and routines described herein represent only one of numerous possible routines that can achieve the desired result, and the invention is not limited to the particular routine shown. Further, it should be understood that some embodiments of the invention can perform fewer than all of the functions performed by the method steps and routines described herein, and that the invention is not limited to embodiments which employ all of the functions performed by the illustrated routines.

The primary routine 1400 may be best understood with reference to FIG. 7 in conjunction with FIG. 14, as the primary routine 1400 is concerned primarily with identifying the various characteristics in a signal such as that shown in FIG. 7 that are indicative of particular events during a user's footsteps (e.g., the heel-strike events 702a-b and toe-off events 704a-b of FIG. 7), and in performing calculations and analyses based upon measured time periods between such events.

As shown, the primary routine 1400 is a continuous loop. As discussed below, various routines within the primary routine 1400 may be capable of performing functions such as responding to a user input to shut down the power of the foot-mounted unit 102, transmitting information from the foot-mounted unit 102 to the wrist-mounted unit 104, and altering a network address of the foot-mounted unit 102/wrist-mounted unit 104 combination. For ease of description, however, these underlying functions will be ignored at the outset, and it will be assumed that the power in the foot-mounted unit 102 remains on at all times. First, a high-level description of the primary routine 1400 will be provided, and then functionality of each of the constituent routines of the primary routine 1400 will be described in more detail below.

For convenience, it may be assumed initially that the primary routine 1400 begins at a routine 1404, wherein the signals 710 and 712 are analyzed to attempt to identify one or more characteristics thereof indicative of a toe-off event 704.

When, during the "toe-off event?" routine 1404, a toe-off event is identified, the primary routine 1400 proceeds to a step 1406, wherein a foot contact time (Tc) is recorded based upon a measured time difference between the time of the identified toe-off even 704 and the time of a heel-strike event 702 previously identified in connection with a "heel-strike event?" routine 1408 of the primary routine 1400 (as described below). It should be appreciated that, during the initial cycle of the primary routine 1400, the first identified toe-off event 704 does not follow a previously identified heel-strike event 702. Therefore, the initial recorded Tc value will be inaccurate. In light of this, the primary routine 1400 may, for example, be permitted to cycle until data for at least one complete footstep has been accumulated before any Tc or Ts values are recorded or used (at the step 1406 or elsewhere) in performing distance, pace, speed, and/or energy expenditure calculations based thereupon. Alternatively, a "dummy" Tc value may be recorded during the initial iteration of the step 1406.

When, during the "toe-off event?" routine 1404, a toe-off event 704 is not identified within a pre-determined period of time, the primary routine 1400 proceeds to a step 1418, wherein an "activity flag" is set to false to indicate a lack of activity of the user 112.

After the step 1418, the primary routine 1400 proceeds to a step 1426, wherein the various timers used to measure the foot contact time (Tc), foot-air time (Ta), and step time (Ts) are reset because of the identified lack of activity.

After the step 1406 (discussed above), the primary routine 1400 proceeds to a "heel-strike event?" routine 1408, wherein it is determined whether one or more characteristics in the signals 710 and 712 can be identified that are indicative of a heel-strike event 702.

When, during the "heel-strike event?" routine 1408, a heel-strike event 702 is identified, the primary routine 1400 proceeds to a step 1410, wherein the "activity flag" (if false) is set to true to indicate that the user 112 is currently active. In addition, at the step 1410, a "step error flag" (if true) is set to false to indicate that both a toe-off event 704 and a heel-strike event 702 were identified in connection with the current footstep.

After the step 1410, the primary routine 1400 proceeds to a step 1412, wherein a measured step-time (Ts) and a measured foot air time (Ta) are recorded. Because, during the initial iteration of the primary routine 1400, the step time (Ts) cannot be accurate, the primary routine 1400 may, for example, wait until both a toe-off even 704 and a heel-strike even 702 have been identified at least once before recording a value of Ts. Alternatively, a "dummy" value may be recorded as the value of Ts. Because both a toe-off event 704 and a heel-strike event 702 were identified in the steps 1404 and 1408, however, the value of the step air time (Ta) may be assumed to be accurate at this stage and that therefore may be recorded, if desired.

When, during the "heel-strike event?" routine 1408, it is determined that a heel-strike event 702 has not occurred within a predetermined time period, the primary routine 1400 proceeds to a step 1420, wherein it is determined whether this is the third consecutive time that a heel-strike event 702 was not identified during the "heel-strike event?" routine 1408.

When, at the step 1420, it is determined that it is not the third consecutive time that a heel-strike event 702 has not been identified during the "heel-strike event?" routine 1408, the primary routine 1400 proceeds to a step 1422, wherein the value of Tc is set to the last recorded Tc value, rather than the current incorrect value, and the value of Ts is set to maximum allowable value of Ts (i.e., the threshold Ts value that caused the "heel-strike event?" routine 1408 to "kick out" to the step 1420. The value of Ts is not replaced by a substitute value in this situation because it is desirable to use cumulative sum of all recorded Ts values as the total elapsed time of the outing, and such replacement would result in an error in this value.

When, at the step 1420, it is determined that it is the third consecutive time that a heel-strike event 702 has not been identified during the "heel-strike event?" routine 1408, the primary routine 1400 proceeds to a step 1424, wherein the "step error flag" (if false) is set to true to indicate that a step monitoring error has occurred. As discussed below, the "step error flag" may be passed to the wrist-mounted unit 104, and used thereby to indicate an anomaly to the user 112.

After the step 1424, the primary routine 1400 proceeds to the step 1426, wherein the Tc, Ta, and Ts timers are reset because of the identified missing of the heel-strike event.

Following either of the steps 1412 or 1426, the primary routine 1400 proceeds to a routine 1414 wherein a determination is made whether the foot-mounted unit 102 should remain powered on, should be powered down, or should be temporarily set to a low-power "sleep" mode. As explained in more detail below in connection with FIG. 25, based upon the level of activity detected (i.e., whether and for how long the "activity flag" has been false), the "check activity?" routine 1414 may take appropriate action. For example, it may cause the foot-mounted unit 102 to enter a temporary, low-power sleep mode, or may set a flag that will cause the foot-mounted unit 102 to power down completely.

After the step 1414, the primary routine 1400 proceeds to a routine 1416, wherein the recorded values of Tc, Ts, and Ta accumulated during the previous iteration of the primary routine 1400 are evaluated and smoothed, and certain values are calculated based thereupon. Such values may, for example, be displayed to the user 112 via a display on the foot-mounted unit 102 and/or may be transmitted to the wrist-mounted unit 104 or elsewhere for display to the user, processing, and/or storage.

After the routine 1416, the primary routine 1400 proceeds to a routine 1402, wherein the primary routine 1400 waits for a predetermined amount of time (see ignore time 708 of FIG. 7) before attempting to identify the next toe-off event 704.

After the routine 1402, the primary routine 1400 returns to the "toe-off event?" routine 1404 (discussed above).

Figure 15:
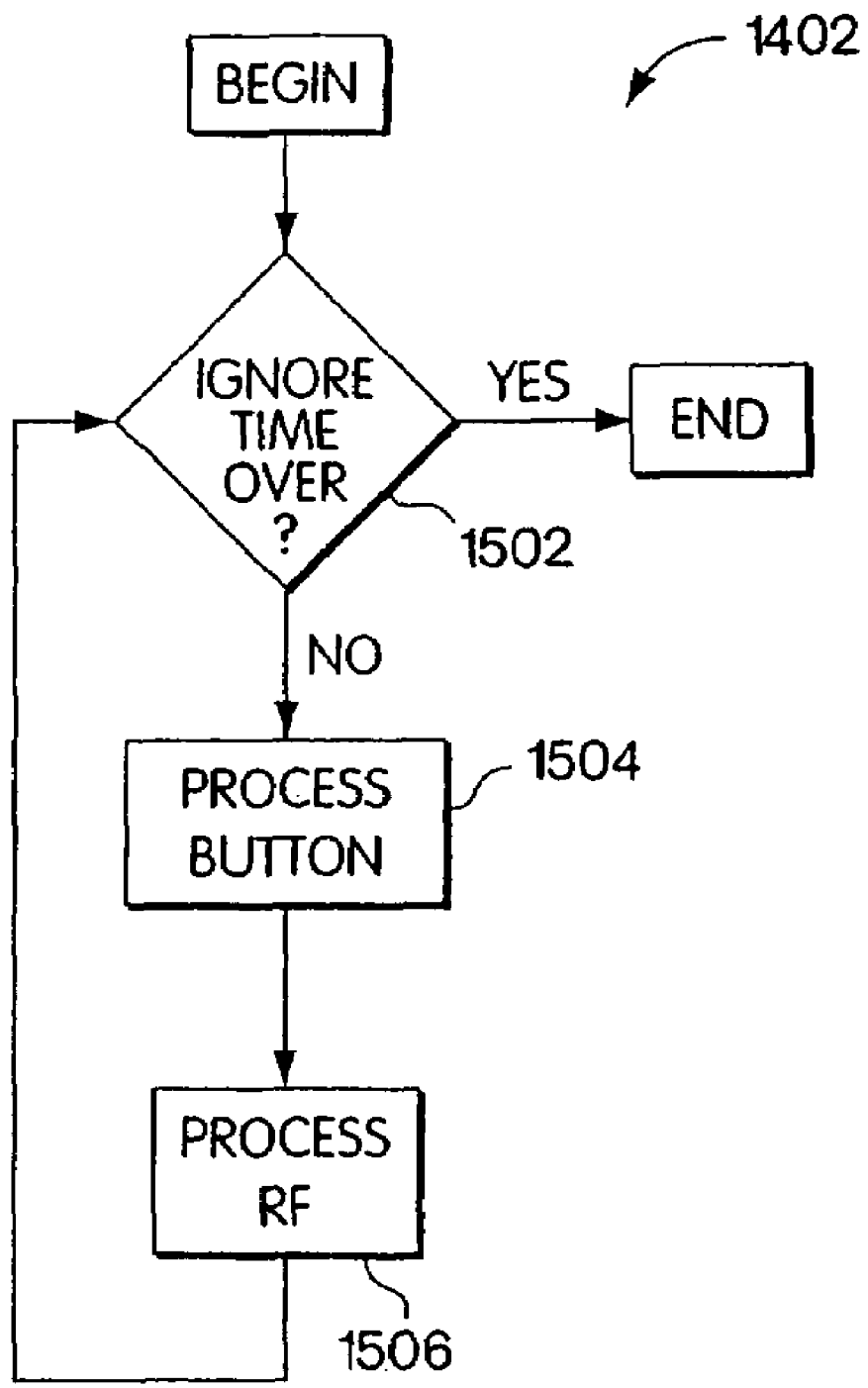
FIG. 15 is a flow diagram illustrating an example implementation of the "wait" routine shown in FIG. 14 which causes the routine to wait a predetermined amount of time after detecting a heel-strike event before beginning to look for a toe-off event.

The various routines of the primary routine 1400 and a number of subroutines thereof now will be discussed. Each of these routines and subroutines may be best understood with reference to FIG. 7, in conjunction with the flow diagram illustrating the same. An example implementation of the "wait" routine 1402 of the primary routine 1400 is illustrated in FIG. 15.

As shown, the routine 1402 begins at a step 1502, wherein it is determined whether the ignore time 708 has elapsed since the last heel-strike event 702.

When, at the step 1502, it is determined that the ignore time 708 has not yet elapsed, the routine 1402 proceeds to the "process button" routine 1504, which is described below in connection with FIG. 16.

After the process button routine 1504, the routine 1402 proceeds to a process RF routine 1506, during which any necessary RF transmission/reception functions, e.g., information transmissions to and/or from the wrist-mounted unit 104 may be performed.

After the routine 1506, the routine 1402 returns to the routine 1502 (discussed above).

Figure 16:
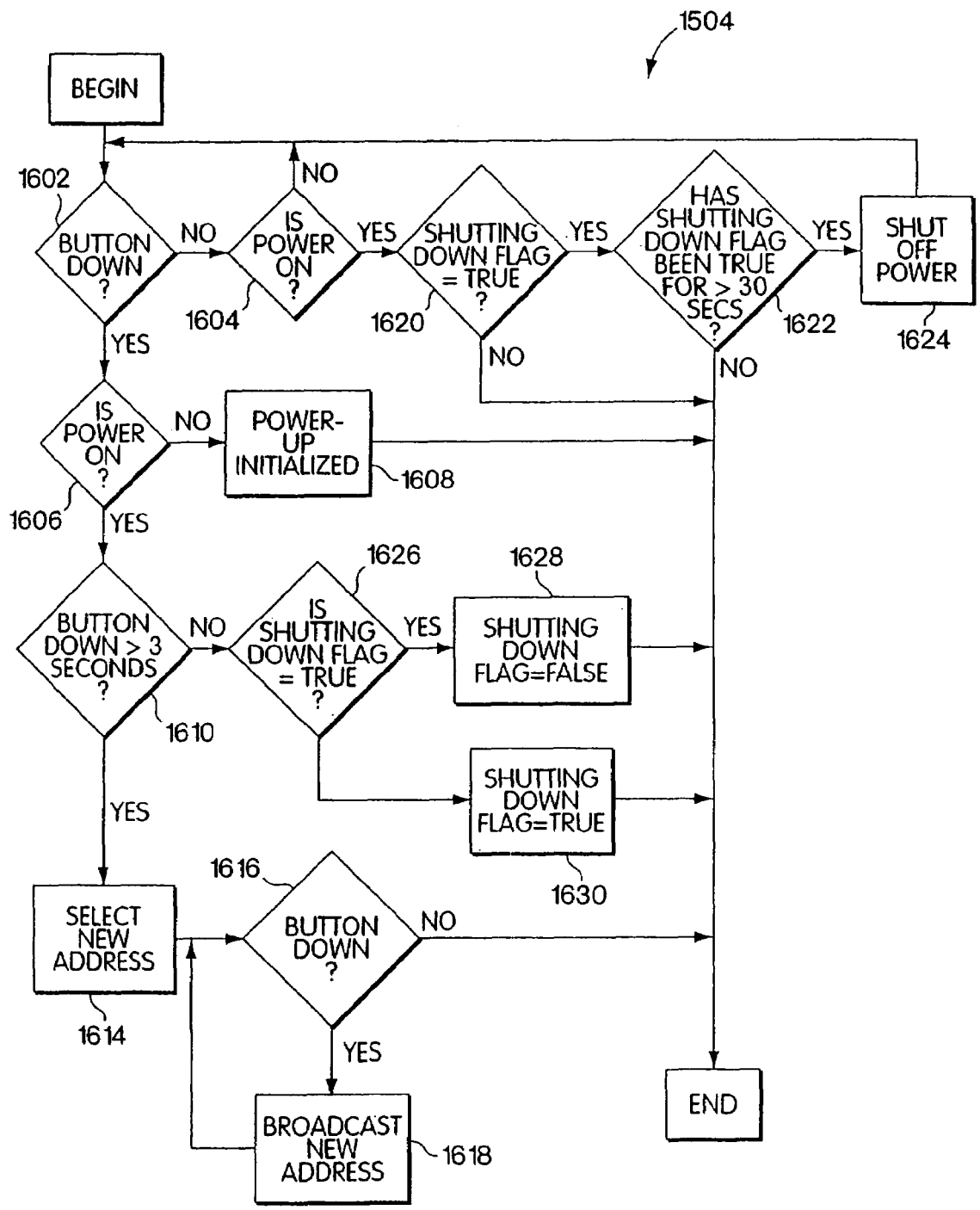
FIG. 16 is a flow diagram illustrating an example implementation of the "process button" routine shown in FIG. 15 which implements the functionality of a button that may be disposed on the foot-mounted unit of FIGS. 1, 2, and 4.

An example implementation of the "process button" routine 1504 of FIG. 15 is shown in FIG. 16. As shown, the routine 1504 begins at step 1602, wherein it is determined whether the button 204 on the foot-mounted unit 102 is currently depressed.

When, at the step 1602, it is determined that the button 204 is not depressed, the routine 1504 proceeds to a step 1604, wherein it is determined whether the foot-mounted unit 102 is currently powered on.

When, at the step 1604, it is determined that the foot-mounted unit 102 is not yet powered on, the routine 1504 proceeds back to the step 1602, wherein it is again determined whether the button 1502 is depressed.

When, at the step 1602, it is determined that the button 204 is depressed, the routine 1504 proceeds to a step 1606, wherein it is determined whether the foot-mounted unit 102 is powered on.

When, at the step 1606, it is determined that the foot-mounted unit 102 is not yet powered on, the routine 1504 proceeds to a step 1608, wherein the foot-mounted unit 102 is powered up and initialized, and the routine 1504 terminates.

When, at the step 1606, it is determined that the foot-mounted unit 102 is already powered on, the routine 1504 proceeds to a step 1610, wherein it is determined whether the button 204 has been depressed for more than three seconds.

When, at the step 1610, it is determined that the button has not been depressed for more than 3 seconds, the routine 1504 proceeds to a step 1626, wherein it is determined whether the shutting down flag is currently true.

When, at the step 1626, it is determined that the shutting down flag is currently true, the routine 1504 proceeds to a step 1628, wherein the shutting down flag is set to false, and the routine 1504 terminates.

When, at the step 1626, it is determined that the shutting down flag is not currently true, the routine 1504 proceeds to a step 1630, wherein the shutting down flag is set to true, ant the routine 1504 terminates. As discussed below in connection with step 1622, after the shutting down flag has been true for more than thirty seconds, the foot-mounted unit is powered down.

When, at the step 1610 (discussed above), it is determined that the button 204 has been depressed for more than three seconds, the routine 1504 proceeds to a step 1614, wherein a new network address for the foot-mounted unit 102 may be selected. In one embodiment of the invention, a new address is selected at random from a group of one-hundred possible addresses.

After the step 1614, the routine 1504 proceeds to a step 1616, wherein it is determined whether the button remains depressed.

When, at the step 1616, it is determined that the button remains depressed, the routine 1504 proceeds to a step 1618, wherein a new network address for the foot-mounted device is broadcasted by the transceiver 420.

When, at the step 1616, it is determined that the button is no longer depressed, the routine 1504 terminates.

When, at the step 1604 (discussed above), it is determined that the foot-mounted unit 102 is currently powered on, the routine 1504 proceeds to a step 1620, wherein it is determined whether the shutting down flag is true.

When, at the step 1620, it is determined that the shutting down flag is true, the routine 1504 proceeds to the step 1622, wherein it is determined whether the shutting down flag has been true for more than thirty seconds.

When, at the step 1622, it is determined that the shutting down flag has been true for more than thirty seconds, the routine 1504 proceeds to a step 1624, wherein the foot-mounted unit is powered down.

After the step 1624, the routine 1504 returns to the step 1602 (discussed above).

Figure 17:
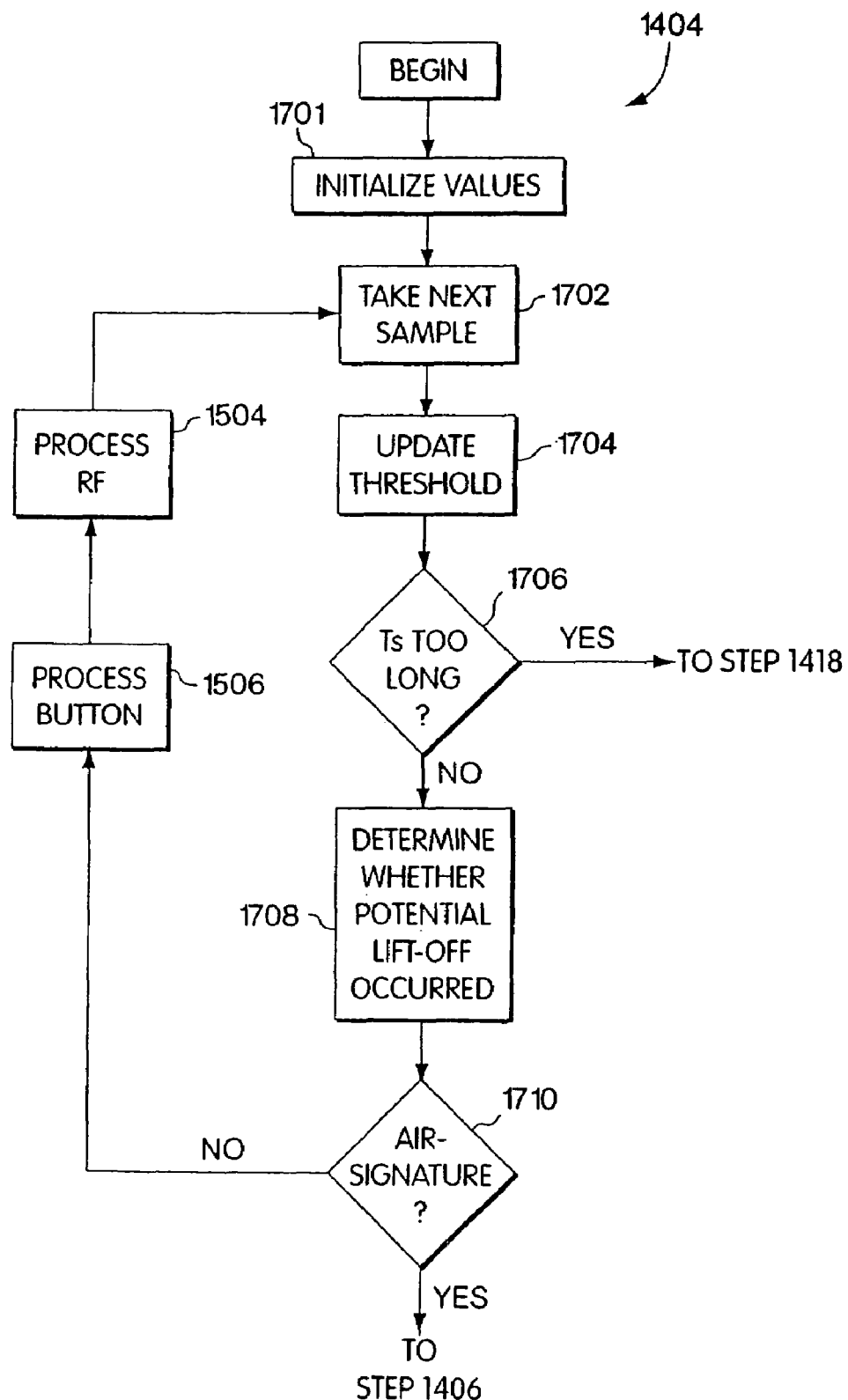
FIG. 17 is a flow diagram illustrating an example implementation of the "toe-off event?" routine shown in FIG. 14 wherein it is determined when the foot of a user leaves the ground during a stride taken by the user.

FIG. 17 shows an illustrative implementation of the "toe-off event?" routine 1404 of the primary routine 1400. As shown in FIG. 17, the "toe-off event?" routine 1404 begins at a step 1701, wherein certain values (discussed below) are initialized.

After the step 1701, the "toe-off event?" routine 1404 proceeds to a step 1702, wherein a sample of an output signal of the sensor 418 (i.e., a difference between the signals 710 and 712 of FIG. 7), is taken.

After the step 1702, the "toe-off event?" routine 1404 proceeds to an "update threshold" routine 1704, during which the value of a variable "threshold" which is used in connection with the "heel-strike event?" "heel-strike event?" routine 1408 (described below). An example of implementation of the "update threshold" routine 1704 is described below in connection with FIG. 23.

After the routine 1704, the "toe-off event?" routine 1404 proceeds to a step 1706, wherein it is determined whether an amount of time has elapsed that is in excess of a maximum possible time of a foot-step (i.e., it is determined whether the toe-off event must have been missed because too much time has elapsed since the last heel-strike event 702).

When, at the step 1706, it is determined that an excessive amount of time has elapsed since the last heel-strike event 704, the "toe-off event?" routine 1404 proceeds to the step 1418 (discussed above in connection with the primary routine 1400).

When, at the step 1706, it is determined that an excessive amount of time has not yet elapsed since the last heel-strike event 704, the "toe-off event?" routine 1404 proceeds to a routine 1708, wherein it is determined whether a potential toe-off event 704 occurred in connection with the last sample taken at the step 1702. An example implementation of the routine 1708 is described below in connection with FIG. 18.

After the routine 1708, the "toe-off event?" routine 1404 proceeds to an "air signature?" routine 1710, wherein it is determined whether an "air signature" 706 has been identified in the signals 710 and 712. An example implementation of the "air signature?" routine 1710 is described below in connection with FIG. 19. As shown in FIG. 7, an air signature in the signals 710 and 712 may be an extended period of relatively constant, negative acceleration during a footstep.

When, at the step 1710, it is determined that an "air signature" has not yet been identified in the signals 710 and 712, the "toe-off event?" routine 1404 proceeds to the "process button" routine 1506 (discussed above), then to the "process RF" routine 1504 (also discussed above), and finally back to the step 1702, wherein another sample of the signals 710 and 712 is taken.

When, at the step 1710, it is determined that an "air signature" has been identified in the sensor signal, the "toe-off event?" routine 1404 proceeds to the step 1406 of the primary routine 1400.

Figure 18:
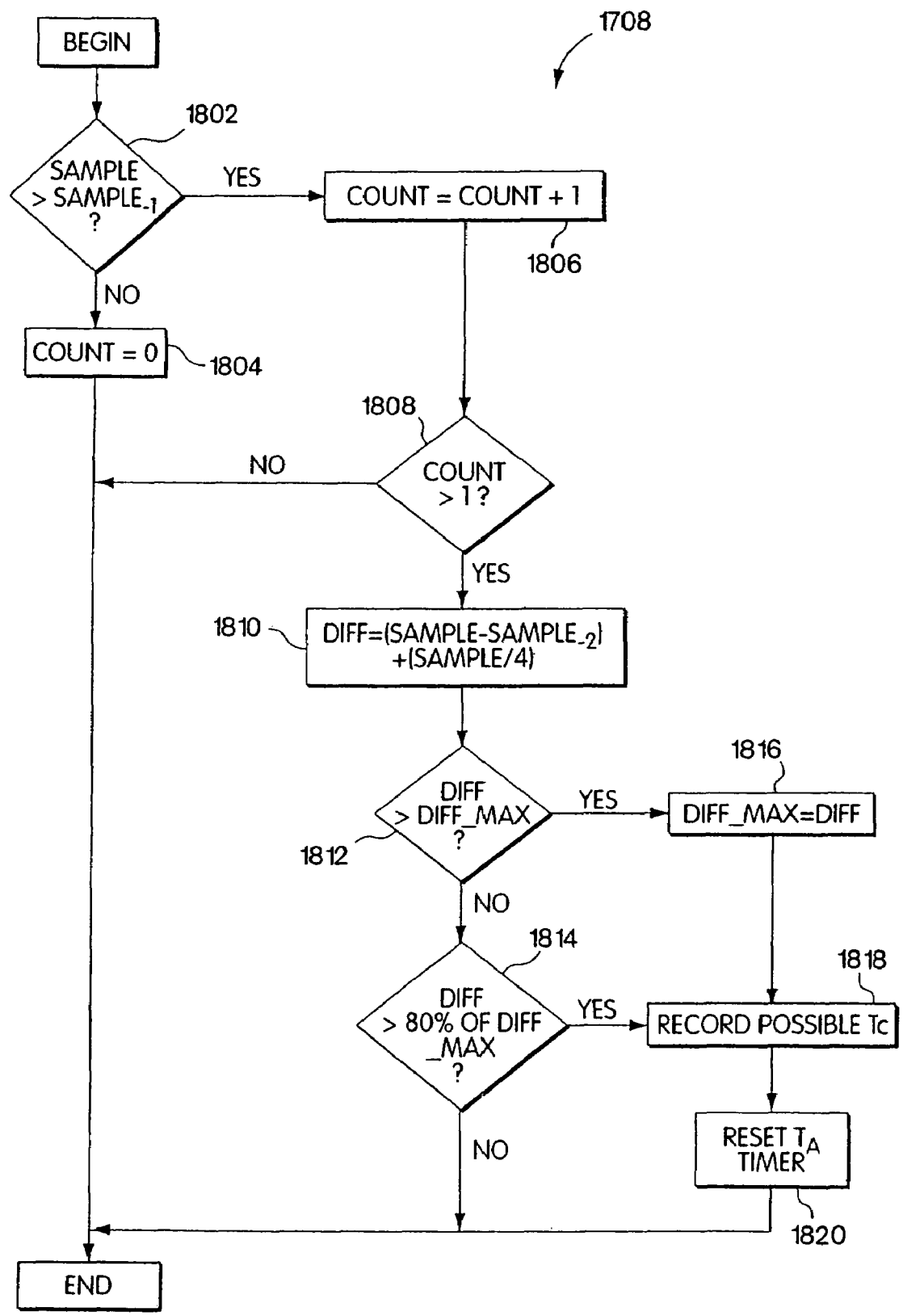
FIG. 18 is a flow diagram illustrating an example implementation of the "determine whether potential lift off occurred" routine shown in FIG. 17.

FIG. 18 shows an illustrative implementation of the routine 1708 of FIG. 17, wherein it is determined whether a potential toe-off event 704 has occurred.

As shown in FIG. 18, the routine 1708 begins at a step 1802 wherein it is determined whether the most recent sample taken during the step 1702 is greater than the next most recent sample taken at the step 1702.

When, at the step 1802, it is determined that the most recent sample is greater than the next most recent sample, the routine 1708 proceeds to a step 1806, wherein a variable "count" is incremented by one. The variable "count" is one of the values that may be initialized in connection with the step 1701 of the "toe-off event?" routine 1404 of FIG. 17.

When, at the step 1802, it is determined that the most recent sample is not greater than the next most recent sample, the routine 1708 proceeds to a step 1804, wherein the variable "count" is reset to zero, and the routine 1708 then terminates.

After the step 1806 (discussed above), the routine 1708 proceeds to a step 1808, wherein it is determined whether the variable "count" is greater than one.

When, at the step 1808, it is determined that the variable "count" is not greater than one, the routine 1708 terminates.

When, at the step 1808, it is determined that the variable "count" is greater than one, the routine 1708 proceeds to a step 1810, wherein a variable "diff" is set to be equal to the value of the current sample minus the value of the third most recent sample, plus the value of the current sample divided by four.

After the step 1810, the routine 1708 proceeds to a step 1812, wherein it is determined whether the variable "diff" is greater than another variable "diff_max." The variable "diff_max" is one of the values which may be initialized in connection with the step 1701 of the "toe-off event?" routine 1404 of FIG. 17.

When, at the step 1812, it is determined that the variable "diff" is greater than the variable "diff_max," the routine 1708 proceeds to a step 1816, wherein the variable "diff_max" is set to be equal to the variable "diff."

After the step 1816, the routine 1708 proceeds to a step 1818, wherein, the current value of a timer used to measure foot contact times (the "Tc timer") is recorded as a possible foot contact time (Tc). The Tc timer may have been reset in connection with the identification of a heel-strike event 702 in the "heel-strike event?" "heel-strike event?" routine 1408 of the primary routine 1400, or may have been reset in connection with the step 1426 of the primary routine 1400.

After the step 1818, the routine 1708 proceeds to a step 1820 wherein the timer used to measure foot air time (the "Ta timer") is reset so that, if the current sample is later determined to be an actual lift-off event, the Ta timer is set appropriately. After the step 1820, the routine 1708 terminates.

When, at the step 1812 (discussed above), it is determined that the variable "diff" is not greater than the variable "diff_max," the routine 1708 proceeds to a step 1814, wherein it is determined whether the variable "diff" is greater than 80% of the variable "diff_max."

When, at the step 1814, it is determined that the variable "diff" is not greater than 80% of the variable "diff_max," the routine 1708 terminates.

When, at the step 1814, it is determined that the variable "diff" is greater than 80% of the variable "diff_max," the routine 1708 proceeds to the step 1818 (discussed above), then to the step 1820 (also discussed above), and the routine 1708 then terminates.

Figure 19:
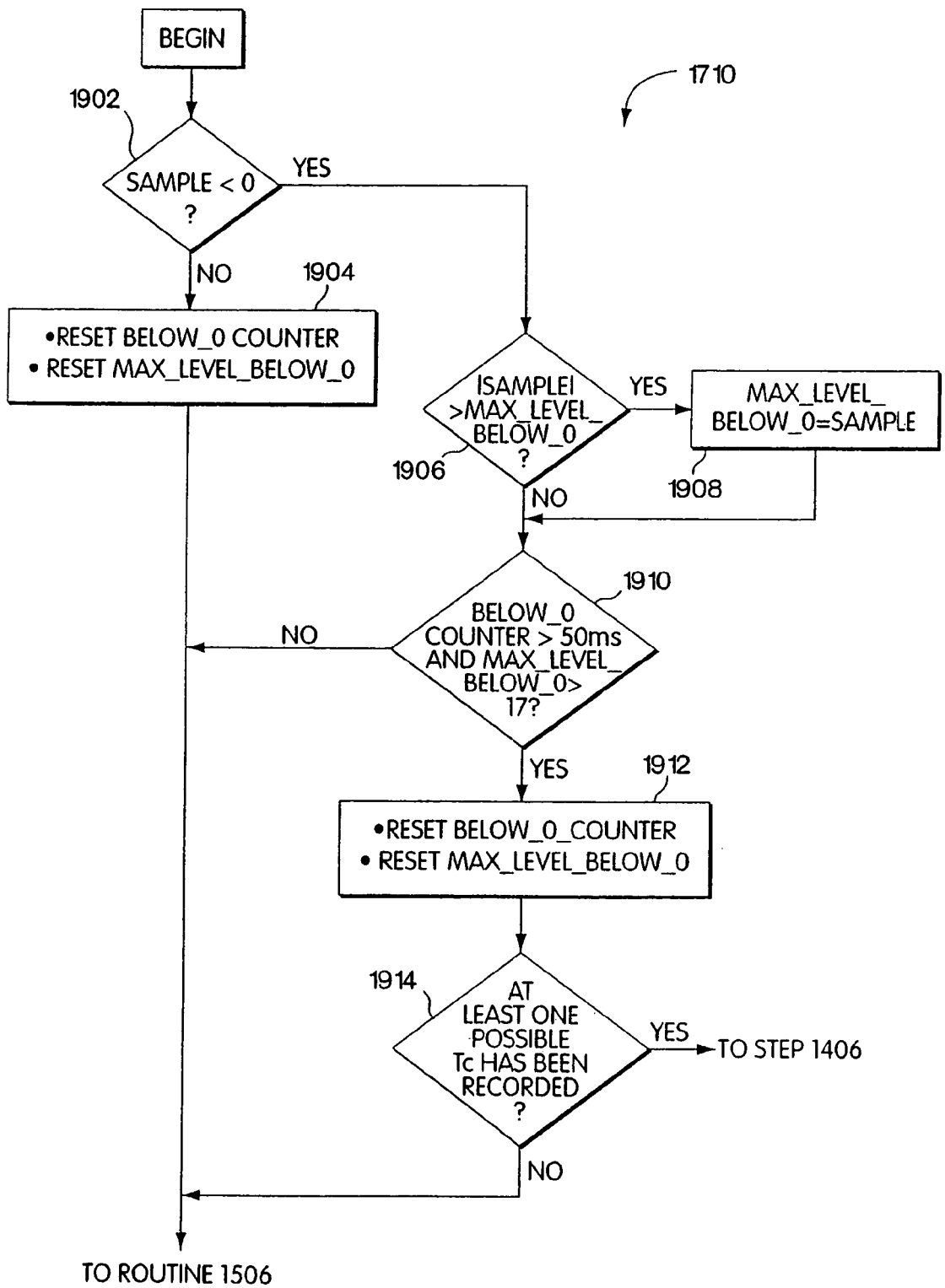
FIG. 19 is a flow diagram illustrating an example implementation of the "air signature?" routine shown in FIG. 17.

FIG. 19 illustrates an illustrative implementation of the "air signature?" routine 1710 of the "toe-off event?" routine 1404 of FIG. 17, during which the signals 710 and 712 are analyzed to identify an "air signature" 706.

As shown, the "air signature?" routine 1710 beings at a step 1902, wherein it is determined whether the current sample is negative. As used herein, a "sample" refers to a voltage difference between the signals 710 and 712 at a particular moment in time. With reference to FIG. 7, assuming that the signal 710 is exactly at level "128," a sample would be positive if it were taken when the signal 712 is at a level greater than level "128," and would be negative if it were taken when the signal is at a level less than level "128."

When, at the step 1902, it is determined that the current sample is positive, the "air signature?" routine 1710 proceeds to a step 1904, wherein a counter that keeps track of a time period during which sequential samples of the signals 710 and 712 are negative (the "below_0" counter) is reset, and a variable "max_level_below_0" also is reset. The variable max_level_below_0 represents the maximum negative acceleration that has occurred since the last time the "below_0" counter was reset.

After the step 1904, the "air signature?" routine 1710 proceeds to the routine 1506 (as shown in FIG. 17).

When, at the step 1902, it is determined that the current sample is negative, the "air signature?" routine 1710 proceeds to step 1906, wherein it is determined whether the absolute value of the sample is greater than the variable max_level_below_0.

When, at the step 1906, it is determined that the absolute value of the sample is greater than the variable max_level_below_0, the "air signature?" routine 1710 proceeds to a step 1908, wherein the variable max_level_below_0 is updated to be equal to the absolute value of the sample. After the step 1908, the "air signature?" routine 1710 proceeds to a step 1910 (discussed below).

When, at the step 1906, it is determined that the sample is not greater than the variable max_level_below_0, the "air signature?" routine 1710 proceeds to the step 1910, wherein it is determined whether: (1) the "below_0" counter has reached fifty milliseconds (ms), and (2) the variable max_level_below_0 is greater than seventeen.

When, at the step 1910, it is determined that both of these conditions are not met, the "air signature?" routine 1710 proceeds to the routine 1506 as shown in FIG. 17.

When, at the step 1910, it is determined that both of these conditions are met, the "air signature?" routine 1710 proceeds to a step 1912, wherein both the "below_0" counter and the variable max_level_below_0 are reset.

After the step 1912, the "air signature?" routine 1710 proceeds to a step 1914, wherein it is determined whether at least one possible Tc has been recorded at the step 1818 of the routine 1708 of FIG. 18.

When, at the step 1914, it is determined that at least one possible Tc has been recorded, the "air signature?" routine 1710 proceeds to the step 1406 of FIG. 14 (discussed above).

When, at the step 1914, it is determined that no Tc has been recorded in connection with step 1818 of the routine 1708, the "air signature?" routine 1710 proceeds to the "process button" routine 1506 as shown in FIG. 17.

Figure 20:
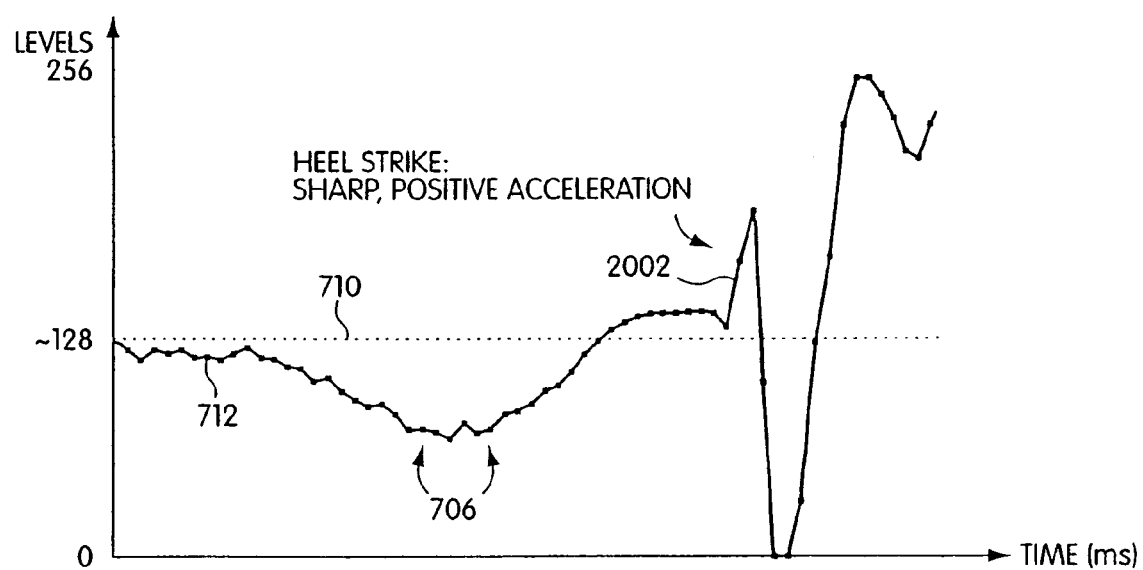
FIG. 20 is a graph showing a typical output signal of a sensor such as that shown in FIGS. 5 and 6 when the heel of a user strikes the ground during a stride taken by the user.

As mentioned above, one of the events identified during each footstep taken by the user 112 is a heel-strike event 702. In accordance with one aspect of the invention, the signals 710 and 712 are analyzed to identify any of a plurality of predetermined criteria indicative of such an event. An example of one such criteria is illustrated in FIG. 20. As shown, after an air signature 706 of the signal 712 has been identified (i.e., it has been determined that the foot 114 of the user 112 is airborne), a subsequent sharp, positive peak 2002 in the signal 712 is one characteristic in the signal 712 that is indicative of the foot 114 of the user 112 impacting the surface 108. Other criteria which, if satisfied, may also be indicative of a heel-strike event 702 are discussed below in connection with the routine 2110 (shown in FIGS. 21 and 22).

In the example embodiment described herein, the "heel-strike event?" routine 1408 of the primary routine 1400 is the routine responsible for performing this analysis.

Figure 21:
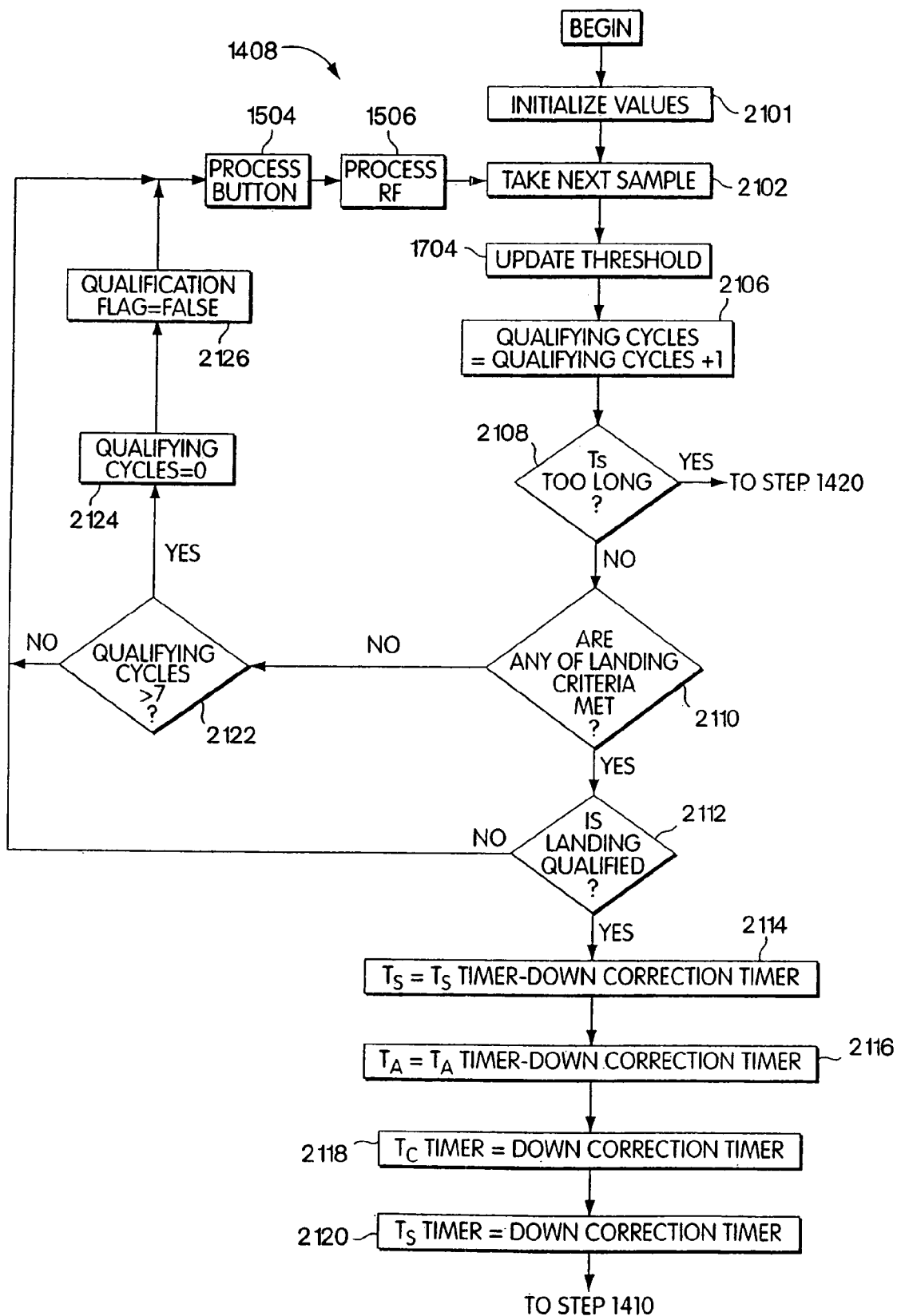
FIG. 21 is a flow diagram illustrating an example implementation of the "heel-strike event?" routine shown in FIG. 14, wherein it is determined when the foot of a user comes into contact with the ground during a stride taken by a user.

An illustrative implementation of the "heel-strike event?" routine 1408 is shown in FIG. 21.

Referring briefly to FIG. 7, the period during which the user's foot 114 is airborne (i.e., the period between each toe-off event 704 and the subsequent heel-strike event 702) is characterized by a relatively smooth signal that is substantially free of sharp transitions. Based upon this characteristic, one goal of the "heel-strike event?" routine 1408 is to identify when one or more sharp transitions first begin to appear in the signal 712. When such sharp transition(s) appear in the signal, it may be concluded that the foot 114 has impacted with the surface 108.

As shown in FIG. 21, the "heel-strike event?" routine 1408 begins at a step 2101, wherein certain values (discussed below) used in connection with the "heel-strike event?" routine 1408 are initialized.

After the step 2101, the "heel-strike event?" routine 1408 proceeds to a step 2102, wherein a sample of the signals 712 and 710 (discussed above) is taken.

After the step 2102, a value of the variable "threshold" is updated in connection with the routine 1704 (discussed below in connection with FIG. 23). As explained below, the variable "threshold" may be used in connection with the steps 2110 and 2112 to determine whether the user's foot 114 has, in fact, impacted with the surface 108. Advantageously, the variable "threshold" is updated dynamically in response to measured characteristics of the samples taken during the preceding five footsteps taken by the user 112.

After the routine 1704, the "heel-strike event?" routine 1408 proceeds to a step 2106, wherein a variable "qualifying cycles" is incremented by one. The variable "qualifying cycles" may, for example, be one of the values that was initialized in connection with the step 2101 discussed above.

After the step 2106, the "heel-strike event?" routine 1408 proceeds to a step 2108, wherein it is determined whether an excessive amount of time has elapsed since the "heel-strike event?" routine 1408 began looking for a heel-strike event 702. That is, it is determine whether the sought-after heel-strike event 702 must have been missed by the "heel-strike event?" routine 1408 because the currently-measured step time (Ts) has reached a value that is outside of a predetermined range of acceptable step times for human beings. In one embodiment, this upper limit on acceptable step time (Ts) is approximately "1360" milliseconds. In this regard, it should be appreciated that, in addition to or in lieu of the maximum acceptable step time (Ts), other variables such as a foot air time (Ta) may also or alternatively be examined at the step 2108 to determine whether the sought-after heel-strike event 702 must have been missed.

When, at the step 2108, it is determined that the current step time (Ts) value has exceeded that maximum acceptable step time, the "heel-strike event?" routine 1408 proceeds to the step 1420 of the primary routine 1400, as shown in FIG. 14.

When, at the step 2108, it is determined that an excessive amount of time has not elapsed since the "heel-strike event?" routine 1408 began looking for a heel-strike event even 702, the "heel-strike event?" routine 1408 proceeds to a step 2110, wherein it is determined whether any of a number of predetermined landing criteria have been met as a result of the most recent sample taken at the step 2102. An example implementation of the routine 2110 is described below in connection with FIG. 22.

When, during the routine 2110, it is determined that at least one of the several predetermined landing criteria was met as a result of the most recent sample taken at the step 2102, the "heel-strike event?" routine 1408 proceeds to a "is landing qualified?" "is landing qualified?" routine 2112, wherein additional analysis may be performed to ensure that the satisfied landing criteria was definitely the result of a heel-strike event 702. An example implementation of the "is landing qualified?" "is landing qualified?" routine 2112 is described below in connection with FIG. 24.

When, during the "is landing qualified?" "is landing qualified?" routine 2112, it is determined that a heel-strike event 702 has indeed been identified, the "heel-strike event?" routine 1408 proceeds to steps 2114, 2116, 2118, and 2120, wherein various variables are set based upon the value of a so-called "down correction" timer. As explained below, this "down correction" timer would have been preset previously in connection with the routine 2110 (FIG. 22) in response to one of the plurality of landing criteria being met.

In essence, the "down correction" timer is used to measure the amount of time that has elapsed since the identification of the first of several samples that are determined to satisfy one of the landing criteria. For example, if three samples are used to satisfy a landing criteria, recognizing that the first of the three samples occurred two sample periods prior to the third sample, the "down correction" timer would have been preset during the routine 2110 to a value equal to two sample periods, and would therefore reflect a time period that has elapsed since the time of that first sample.

At the step 2114, the value of Ts is set to be equal to the current value of the Ts timer minus the current value of the "down correction" timer. The Ts timer may have been preset to the value of the "down correction" timer in connection with a step 2120 (described below) during a previous iteration of the "heel-strike event?" routine 1408, or may have been reset in connection with the step 1426 (discussed above) of the primary routine 1400.

Similarly, at the step 2116, the value of Ta is set to be equal to the current value of the Ta timer minus the current value of the "down correction" timer. Therefore, the value of Ta also takes into account the time at which the first of several samples used to satisfy one of the landing criteria was taken. The Ta timer may have been reset at the step 1820 of the routine 1708 (FIG. 18), or it may have been reset at the step 1426 of the primary routine 1400.

At the steps 2118 and 2120, the Tc timer and Ts timer each are preset to the current value of the "down correction" timer.

After the step 2120, the "heel-strike event?" routine 1408 proceeds to the step 1410 of the primary routine 1400, as shown in FIG. 14.

Figure 24:
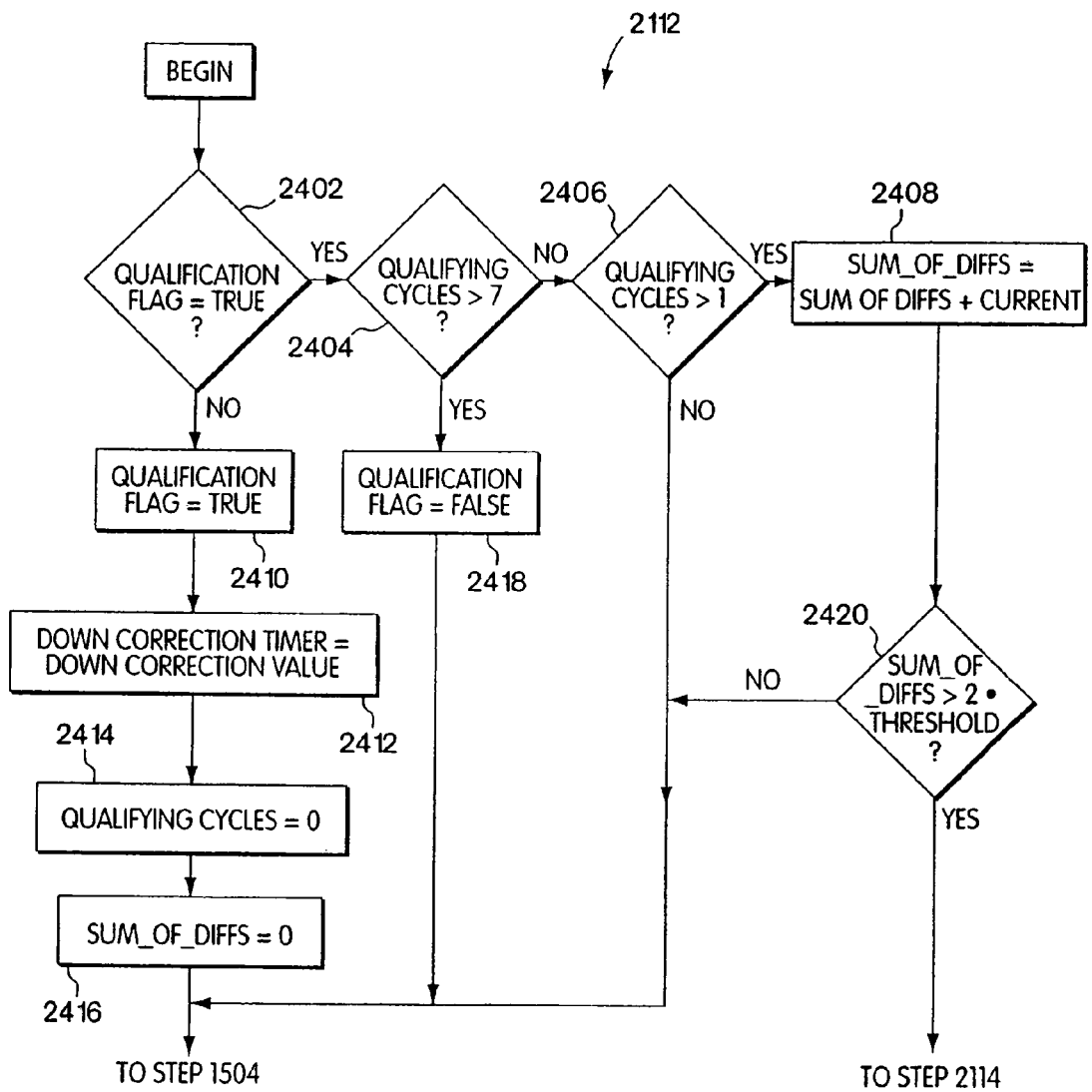
FIG. 24 is a flow diagram illustrating an example implementation of the "is landing qualified?" routine shown in FIG. 21 during which the value of the variable "threshold" determined in connection with the routine of FIG. 23 is used to qualify a potential heel-strike event identified by the "are any of landing criteria met?" routine of FIG. 22.

When, during the routine 2110 (described above), it is determined that none of the landing criteria were met as a result of the most recent sample taken at the step 2102, the "heel-strike event?" routine 1408 proceeds to step 2122, wherein it is determined whether a variable "qualifying cycles" is greater than seven. The significance of the variable "qualifying cycles," as well as the so-called "qualification flag," will be explained below in connection with the description of the "is landing qualified?" routine 2112 (FIG. 24).

When, at the step 2122, it is determined that the variable "qualifying cycles" is not greater than seven, the "heel-strike event?" routine 1408 proceeds first to the routines 1504 and 1506 (discussed above), and then back to the step 2102, wherein another sample of the signals 710 and 712 is taken.

When, at the step 2122, it is determined that the variable "qualifying cycles" is greater than seven, the "heel-strike event?" routine 1408 proceeds to steps 2124 and 2126, wherein the variable "qualifying cycles" is reset to zero, and the "qualification flag" is set to false.

After the step 2126, the "heel-strike event?" routine 1408 proceeds first to the routines 1504 and 1506 (discussed above), and then back to the step 2102, wherein another sample of the signals 710 and 712 is taken.

When, at during the "is landing qualified?" routine 2112, it is determined that a heel-strike event 702 has not yet been confirmed, the "heel-strike event?" routine 1408 proceeds first to the routines 1504 and 1506 (discussed above), and then back to the step 2102, wherein another sample of the signals 710 and 712 is taken.

Figure 22:
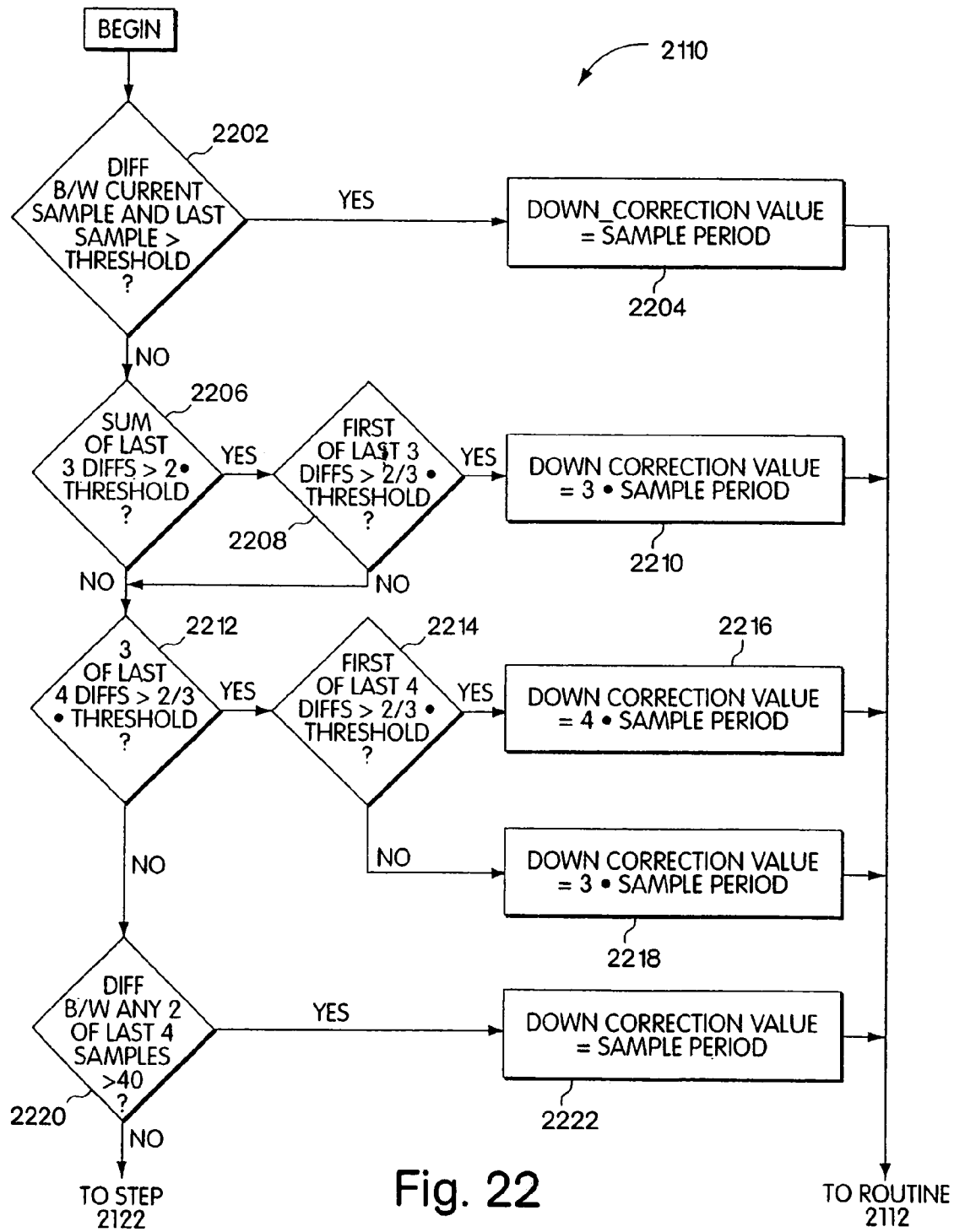
FIG. 22 is a flow diagram illustrating an example implementation of the "are any of landing criteria met?" routine shown in FIG. 21.

FIG. 22 shows an example implementation of the routine 2110 shown in FIG. 21. As mentioned above, the routine 2110 serves to identify one or more characteristics in the signals 710 and 712 that satisfy at least one of a plurality of predetermined criteria consistent with the occurrence of a heel-strike event 702.

As shown, the routine 2110 begins at a step 2202, wherein it is determined whether the difference between a current sample and the next most recent sample is greater than the variable "threshold." As mentioned above, the value of the variable "threshold" may be dynamically adjusted based upon at least one characteristic of one or more previously taken samples. For example, in the illustrative routine 1704 described below in connection with FIG. 23, samples taken during the last five footsteps of the user 112 are used to dynamically set the value of the variable "threshold." It should be appreciated, however, that the quantity "threshold" may alternatively be a fixed (i.e., non-variable) value, and the invention is not limited to embodiments that employ a dynamically-adjusted value as the "threshold."

When, at the step 2202, it is determined that the difference between the current sample and the next most recent sample is greater than the value of the variable "threshold," the routine 2110 proceeds to a step 2204, wherein a variable "down correction value" is set to be equal to the single sample period between the two samples. The variable "down correction value" is used to preset the "down correction" timer in connection with the "is landing qualified?" "is landing qualified?" routine 2112 (see FIG. 24).

After the step 2204, the routine 2110 proceeds immediately to the "is landing qualified?" "is landing qualified?" routine 2112 of the "heel-strike event?" routine 1408, as shown in FIG. 21.

When, at the step 2202, it is determined the difference between the two most recent samples is not greater than the value of the variable "threshold," the routine 2110 proceeds to a step 2206, wherein it is determined whether the sum of the last three differences (i.e., the three differences between consecutive ones of the last four samples) is greater than two times the value of the variable "threshold."

When, at the step 2206, it is determined that the sum of the last three differences is greater than two times the value of the variable "threshold," the routine 2110 proceeds to a step 2208, wherein it is determined whether the first one of the last three differences is greater than two-thirds of the value of the variable "threshold."

When, at the step 2208, it is determined that the first of the last three differences is greater than two-thirds of the value of the variable "threshold," the routine 2110 proceeds to a step 2210, wherein the variable "down correction value" is set to be equal to three times the sample period. The variable "down correction value" is set to this value because it is recognized that three sample periods have occurred since the first of the four samples analyzed in connection with the steps 2206 and 2208 was taken.

When, at the step 2208, it is determined that the first of the last three differences is not greater than two-thirds of the value of the variable "threshold," the routine 2210 proceeds to a step 2212 (described below).

When, at the step 2206, it is determined that the sum of the last three differences is not greater than two times the value of the variable "threshold," the routine 2110 also proceeds to the step 2212.

At the step 2212, it is determined whether three of the last four differences (i.e., the differences between consecutive ones of the last five samples) are greater than two-thirds of the value of the variable "threshold."

When, at the step 2212, it is determined that three of the last four differences are greater than two-thirds of the value of the variable "threshold," the routine 2110 proceeds to a step 2214, wherein it is determined whether the first one of the last four differences is greater than two-thirds of the value of the variable "threshold."

When, at the step 2214, it is determined that the first one of the last four differences is greater than two-thirds of the value of the variable "threshold," the routine 2110 proceeds to a step 2216, wherein the variable "down correction value" is set to be equal to four times the sample period. The variable "down correction value" is set to this value because it is recognized that four full sample periods have elapsed since the first of the five samples analyzed in connection with the steps 2212 and 2214 was taken.

When, at the step 2214, it is determined that the first of the last four differences is not greater than two-thirds of the value of the variable "threshold," the routine 2110 proceeds to a step 2218, wherein the variable "down correction value" is set to be equal to three times the sample period. The variable "down correction value" is set to this value because it is recognized that the first of the last five samples was not used in satisfying a criterion of the steps 2212 and 2214, but that the second of the last five samples must have been so used. Therefore, three sample periods would have elapsed between the second of the last five samples and the most recent one of the last five samples.

When, at the step 2212, it is determined that three of the last four differences are not greater than two-thirds of the value of the variable "threshold," routine 2110 proceeds to a step 2220, wherein it is determined whether the difference between any two of the last four samples is greater than "40" levels (using the scale of 0-256 levels discussed above in connection with FIG. 7).

When, at the step 2220, it is determined that the difference between two of the last four samples is greater than "40" levels, the routine 2110 proceeds to a step 2222, wherein the variable "down correction value" is set to be equal to a single sample period.

After the step 2222, the routine 2110 proceeds to the "is landing qualified?" routine 2112 of the routine 1408, as shown in FIG. 21.

When, at the step 2220, it is determined that no difference between any two of the last four samples is greater than "40" levels, the routine 2110 proceeds to the step 2122 of the "heel-strike event?" routine 1408, as shown in FIG. 21.

Figure 23:
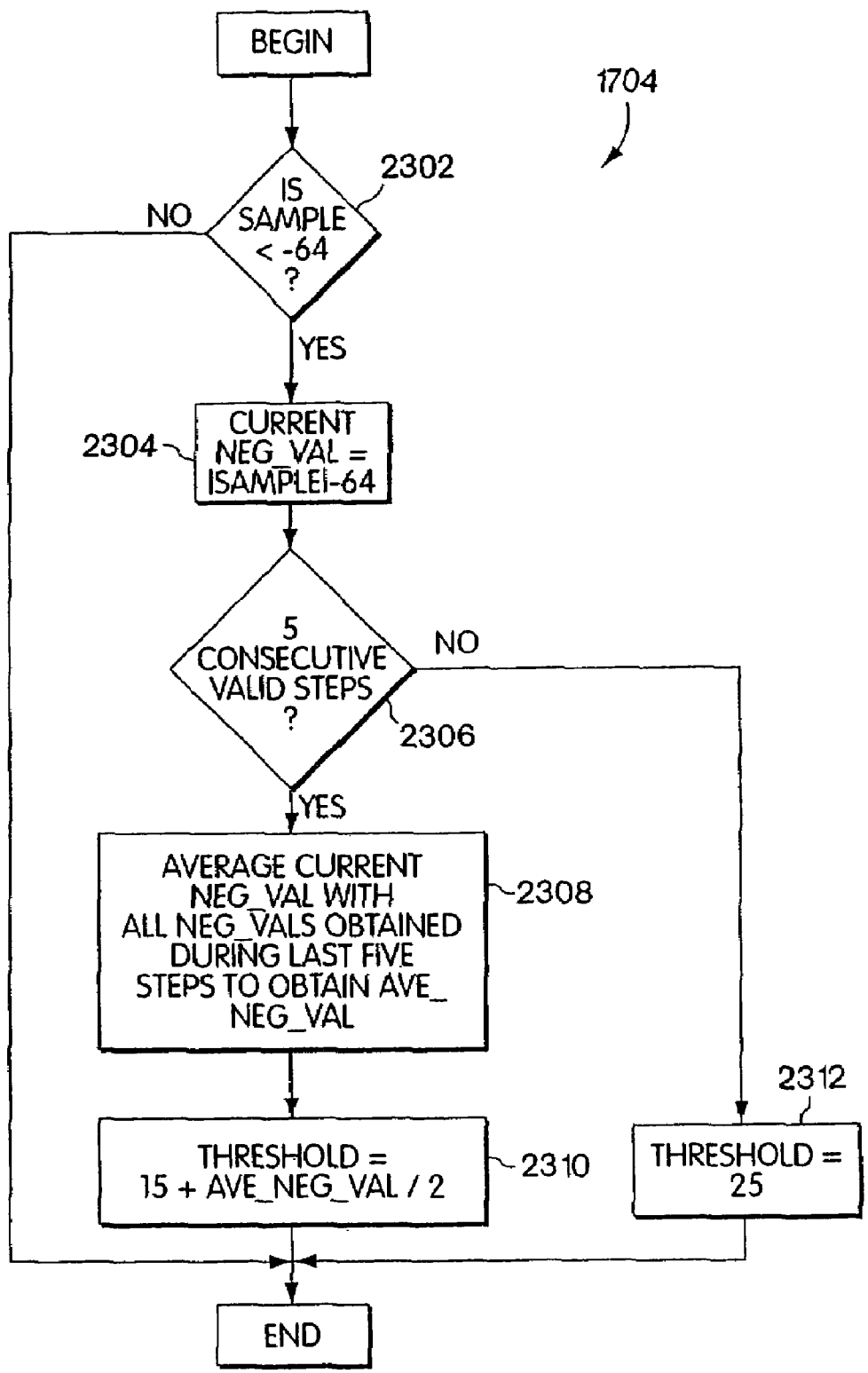
FIG. 23 is a flow diagram illustrating an example implementation of the "update threshold" routine shown in each of FIGS. 17 and 21 which may be used to dynamically update a threshold value for detecting a heel-strike event in response to one or more changing characteristics of the signal output by the sensor of the foot-mounted device shown in FIGS. 4-6.

FIG. 23 shows an example implementation of the routine "update threshold" 1704, which may be performed after each of the steps 1702 and 2102 of the "toe-off event?" routine 1404 and the "heel-strike event?" routine 1408, respectively.

As shown in FIG. 23, the "update threshold" routine 1704 begins at a step 2302, wherein it is determined whether the sample is less than "−64." Again, it should be appreciated that each "sample" taken represents a difference between the current level (on a scale of 0-255) of the active signal 712 and the current level of the reference signal 710. Therefore, a given sample will be less than "−64" only when the current level of the active signal 712 is more than "64" levels below the current level of the reference signal 710.

When, at the step 2302, it is determined that the current sample is not less than "−64," the "update threshold" routine 1704 terminates.

When, at the step 2302, it is determined that the current sample is less than "−64," the "update threshold" routine 1704 proceeds to a step 2304, wherein a variable "neg val" is set to be equal to the absolute value of the sample (which will be positive and greater than "64") minus "64."

After the step 2304, the "update threshold" routine 1704 proceeds to a step 2306, wherein it is determined whether five consecutive "valid" steps have been identified in connection with the primary routine 1400 of FIG. 14. A valid step may be identified, for example, when the "activity flag" is true and the "step error flag" is false for five consecutive iterations of the primary routine 1400.

When, at the step 2306, it is determined that five consecutive valid steps have not yet been identified, the "update threshold" routine 1704 proceeds to a step 2312, wherein the variable "threshold" is set to be equal to a default value of "25,"

After the step 2312, the "update threshold" routine 1704 terminates.

When, at the step 2306, it is determined that five consecutive valid steps have been identified, the "update threshold" routine 1704 proceeds to a step 2308, wherein the current value of the variable "neg_val" is averaged with all other values of the variable "neg_val" that have been obtained during the last five footsteps taken by the user 112, thereby obtaining another variable "ave_neg_val."

After the step 2308, the "update threshold" routine 1704 proceeds to a step 2310, wherein the variable "threshold" is set to be equal to "15," plus the value of the variable "ave_neg_val" divided by 2.

After the step 2310, the "update threshold" routine 1704 terminates.

FIG. 24 is a flow diagram of an example implementation of the "is landing qualified?" routine 2112 of the "heel-strike event?" routine 1408 shown in FIG. 21. As shown in FIG. 24, the "is landing qualified?" routine 2112 begins at a step 2402, wherein it is determined whether the "qualification flag" is true. The "qualification flag" may, for example, be one of the values initialized in connection with the step 2101 (FIG. 21), so that the "qualification flag" is set to be false when the "is landing qualified?" routine 2112 begins.

When, at the step 2402, it is determined that the "qualification flag" is not yet true, the "is landing qualified" routine 2112 proceeds to a step 2410, wherein the "qualification flag" is set to true. Because the "is landing qualified?" routine 2112 is entered only when at least one of the several landing criteria of the routine 2110 has been met, the "qualification flag" is set to true in connection with the step 2410 only after at least one of these landing criteria has been met. As explained in more detail below, the setting of the "qualification flag" to true in connection with the step 2410 enables a heel-strike event 702 to possibly be qualified during a subsequent iteration of the "is landing qualified?" routine 2112.

After the step 2410, the "is landing qualified?" routine 2112 proceeds to a step 2412, wherein the "down correction" timer is set to be equal to the current value of the variable "down correction value." The variable "down correction value" may have been set, for example, in connection with the routine 2110 of FIG. 22. By so setting the "down correction" timer at the step 2412, the "down correction" timer correctly reflects the time period that has elapsed since the first of several samples that satisfied one of the landing criteria of the routine 2110 was taken. In this manner, when a heel-strike event 702 eventually is qualified in connection with a subsequent iteration of the "heel-strike event?" routine 1408, the value of the "down correction" timer can be used to "correct" the values of the Ts and Ta timers in connection with the steps 2114 and 2116, respectively, of the "heel-strike event?" routine 1408 of FIG. 21.

After the step 2412, the "is landing qualified?" routine 2112 proceeds to steps 2414 and 2416, wherein the variables "qualifying cycles" and "sum_of_diffs are each reset to zero. In accordance with one embodiment of the invention, after the "qualification flag" is set to true at the step 2410 in response to one of the landing criteria of the routine 2110 being met, the "heel-strike event?" routine 1408 requires again that one of the landing criteria be met, this time within the next six iterations of the "heel-strike event?" routine 1408. This is why, at the step 2122 of the "heel-strike event?" routine 1408, it is determined whether the variable "qualifying cycles" is greater than seven, and why the qualification flag is set to false at the step 2126 if more than seven qualifying cycles have elapsed.

After the step 2416, the "is landing qualified?" routine 2112 proceeds to the step 2102 of the "heel-strike event?" routine 1408, as shown in FIG. 21, wherein the next sample of the signals 710 and 712 is taken.

When, at the step 2402 (described above), it is determined that the "qualification flag" is true, the "is landing qualified?" routine 2112 proceeds to a step 2404, wherein it is determined whether the variable "qualifying cycles" is greater than seven.

When, at the step 2404, it is determined that the variable "qualifying cycles" is greater than seven, the "is landing qualified?" routine 2112 proceeds to a step 2418, wherein the "qualification flag" is set to false, thereby preventing the identified characteristic of the signals 710 and 712 that initially caused the qualification flag to be set to true from being qualified as an actual heel-strike event 702.

When, at the step 2404, it is determined that the variable "qualifying cycles" is not greater than seven, the "is landing qualified?" routine 2112 proceeds to a step 2406, wherein it is determined whether more than one qualifying cycle has elapsed since the "qualification flag" was set to true. In other words, the step 2406 prevents the "is landing qualified?" routine 2112 from qualifying a heel-strike event 702 when a landing criterion is met only during two consecutive iterations of the "heel-strike event?" routine 1408. Rather, the step 2406 requires the "heel-strike event?" routine 1408 to undergo at least one iteration after a first landing criterion is met before a second landing criterion can be used to qualify a heel-strike event 702.

When, at the step 2406, it is determined that the variable "qualifying cycles" is not greater than one, the "is landing qualified?" routine 2112 proceeds to the step 2102 of the "heel-strike event?" routine 1408 so that a new sample may be taken.

When, at the step 2406, it is determined that the variable "qualifying cycles" is two or greater, the "is landing qualified?" routine 2112 proceeds to a step 2408, wherein the variable "sum_of_diffs" is incremented by the difference between the current sample and the next most recent sample taken at the step 2102 of the "heel-strike event?" routine 1408.

After the step 2408 (discussed above), the "is landing qualified?" routine 2112 proceeds to a step 2420, wherein it is determined whether the value of the variable "sum_of_diffs" is greater than two times the value of the variable "threshold" (discussed above).

When, at the step 2420, it is determined that the value of the variable "sum_of_diffs" is not greater than two times the value of the variable "threshold," the "is landing qualified?" routine 2112 proceeds to the step 2102 of the "heel-strike event?" routine 1408 so that the next sample may be taken.

When, at the step 2420, it is determined that the value of the variable "sum_of_diffs" is greater than two times the value of the variable "threshold," the "is landing qualified?" routine 2112 proceeds to the steps 2114, 2116, 2118, and 2120 of the "heel-strike event?" routine 1408, as shown in FIG. 21.

Figure 25:
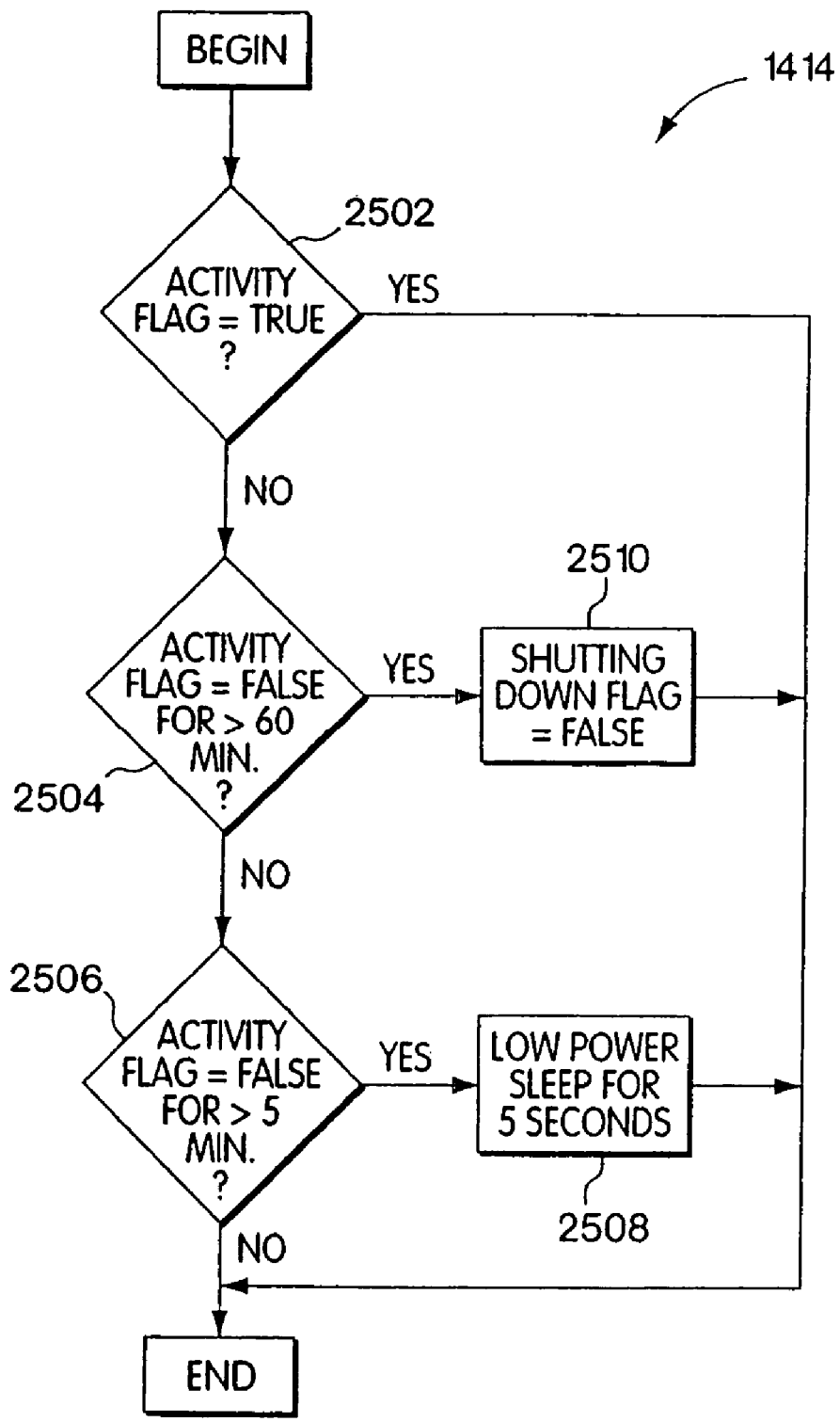
FIG. 25 is a flow diagram illustrating an example implementation of the "check activity" routine shown in FIG. 14 during which the foot-mounted unit may be caused to enter a low-power mode or to shut down entirely if little or no activity is detected.

FIG. 25 is a flow diagram showing an example implementation of the "check activity?" routine 1414 of the primary routine 1400 (FIG. 14). As shown, the "check activity?" routine 1414 begins at a step 2502, wherein it is determined whether the "activity flag" is true.

When, at the step 2502, it is determined that the "activity flag" is true, the "check activity?" routine 1414 terminates.

When, at the step 2502, it is determined that the "activity flag" is not true, the "check activity?" routine 1414 proceeds to a step 2504, wherein it is determined whether the "activity flag" has been false for more than sixty minutes.

When, at the step 2504, it is determined that the "activity flag" has been false for more than sixty minutes, the routine "check activity?" routine 1414 proceeds to a step 2510, wherein the "shutting down flag" is set to false. As described above in connection with the "process button" routine 1504 (FIG. 16), the placing of the "shutting down flag" in the false state will cause the foot-mounted device 102 to be powered down unless the user 112 pushes the button 204 within 30 seconds (see steps 1620-24).

When, at the step 2504, it is determined that the "activity flag" has not been false for more than sixty minutes, the "check activity?" routine 1414 proceeds to a step 2506, wherein it is determined whether the "activity flag" has been false for more than five minutes.

When, at the step 2506, it is determined that the "activity flag" has been false for more than five minutes, the "check activity?" routine 1414 proceeds to a step 2508, wherein the foot-mounted unit 102 is placed into a low-power sleep mode for approximately five seconds. Thus, whenever it is determined that the foot-mounted unit 102 has been inactive for a particular period of time (e.g., five minutes), it may be kept in a low-power mode, waking up only briefly every five seconds or so to determine whether any new activity can be identified.

After the step 2508, the "check activity?" routine terminates.

When, at the step 2506, it is determined that the "activity flag" has not been false for more than 5 minutes, the "check activity?" routine 1414 terminates.

Figure 26:
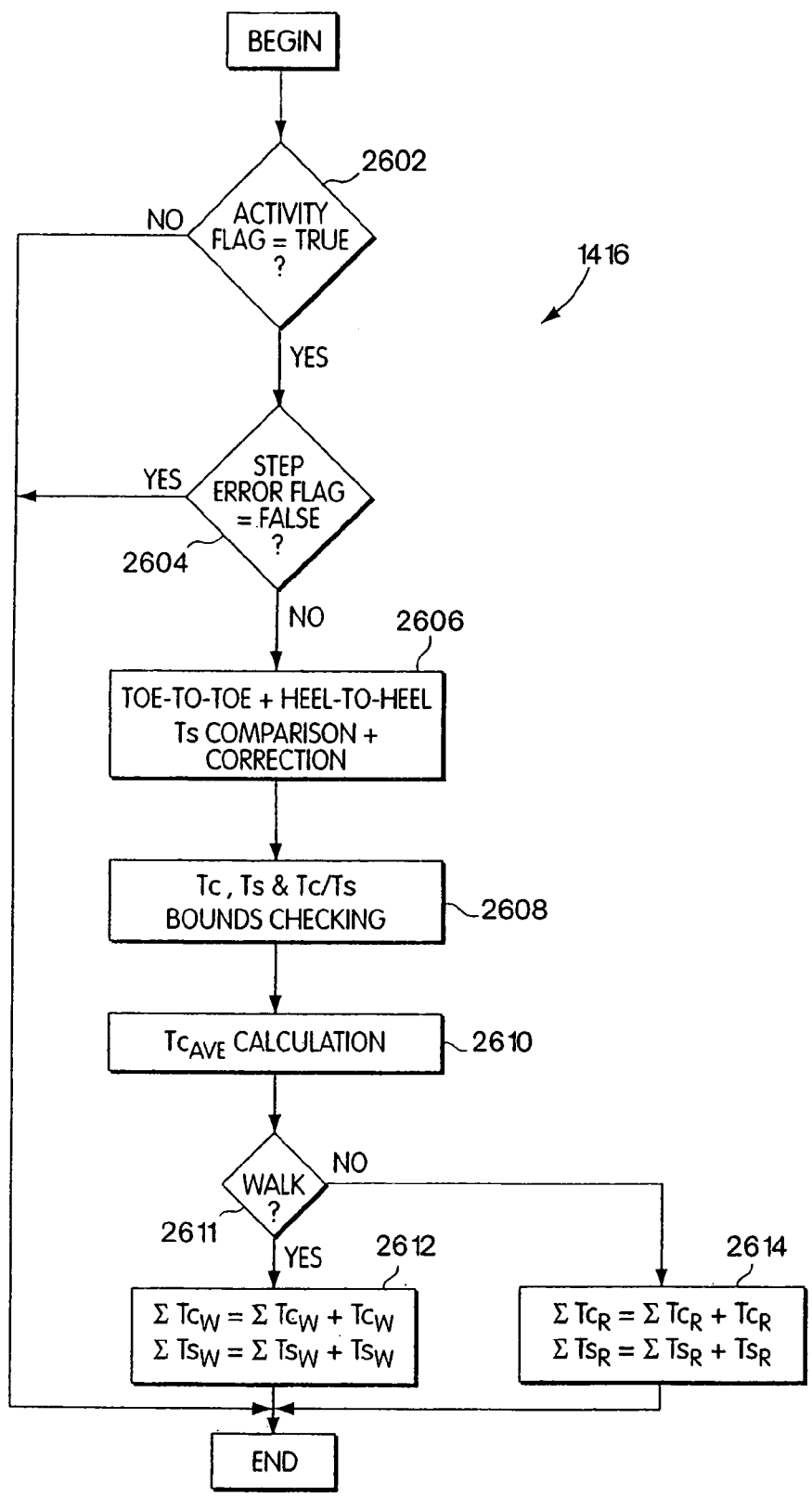
FIG. 26 is a flow diagram illustrating an example implementation of the "smooth and calculate" routine shown in FIG. 14 during which values obtained during the primary routine of FIG. 14 may be validated or corrected, and activity-related calculations may be performed using the same.

FIG. 26 is a flow diagram of an illustrative implementation of the "smooth and calculate" routine 1416 of the primary routine 1400 (FIG. 14.). As shown in FIG. 26, the "smooth and calculate" routine 1416 begins at a step 2602, wherein it is determined whether the "activity flag" is true.

When, at the step 2602, it is determined that the "activity flag" is not true, the "smooth and calculate" routine 1416 terminates.

When, at the step 2602, it is determined that the "activity flag" is true, the "smooth and calculate" routine 1416 proceeds to a step 2604, wherein it is determined whether the "step error flag" is false.

When, at the step 2604, it is determined that the "step error flag" is false, the "smooth and calculate" routine 1416 terminates.

When, at the step 2604, it is determined that the "step error flag" is not false, the "smooth and calculate" routine 1416 proceeds to a routine 2606, wherein, for each footstep, the measured time between consecutive toe-off events 704 is compared to the measured time between corresponding consecutive heel-strike events 702, and correction are (possibly)

made based upon these comparisons. An example implementation of the routine 2606 is described below in connection with FIGS. 27 and 28.

After the routine 2606, the "smooth and calculate" routine 1416 proceeds to a routine 2608, wherein the values of Tc and Ts measured during the most recent iteration of the primary routine 1400 (as well as the ratio between these values) are checked to be sure that they fall within acceptable ranges. An example implementation of the routine 2608 is described below in connection with FIGS. 29 and 30.

After the routine 2608, the "smooth and calculate" routine 1416 proceeds to a routine 2610, during which an average value of the foot contact times ($Tc_{AVE}$) for the last several footsteps is calculated. In accordance with one embodiment, the number of Tc values used to calculate the value of $Tc_{AVE}$ is dependent upon the difference between the most recent Tc value and the last-calculated value of $Tc_{AVE}$. An example implementation of the routine 2610 is described below in connection with FIG. 31.

After routine 2610, the "smooth and calculate" routine 1416 proceeds to a step 2611, wherein it is determined whether the user 112 is walking. This determination may, for example, be made solely upon the most recently measured Tc value. According to one embodiment, when the most recent Tc value is greater than "420" milliseconds, it is determined at step 2611 that the user 112 is walking. On the other hand, when the most recent Tc value is less than "420" milliseconds, it is determined at the step 2611 that the user 112 is running.

When, at the step 2611, it is determined that the user 112 is walking, the "smooth and calculate" routine 1416 proceeds to a step 2612, wherein the most recent "walking" Tc value ($Tc_W$) is added to a running total of previously-obtained "walking" Tc values ($\Sigma Tc_W$), and the current "walking" Ts value ($Ts_W$) is added to a running total of previously-obtained "walking" Ts values ($\Sigma Ts_W$).

After the step 2612, the "smooth and calculate" routine 1416 terminates.

When, at the step 2611, it is determined that the user 112 is not walking, the "smooth and calculate" routine 1416 proceeds to a step 2614, wherein the most recent "running" Tc value ($Tc_R$) is added to a running total of previously-obtained "running" Tc values ($\Sigma Tc_R$), and the most recent "running" Ts value ($Ts_R$) is added to a running total of previously-obtained "running" Ts values ($\Sigma Ts_R$).

After the step 2614, the "smooth and calculate" routine 1416 terminates.

The running totals $\Sigma Tc_W$, $\Sigma Ts_W$, $\Sigma Tc_R$, and $\Sigma Ts_R$ may be stored, for example, in respective 12-bit registers, with each bit representing a particular discrete period of time. In one embodiment of the invention, the current Tc and Ts values are added to the respective registers regardless of whether such addition would cause the registers to drop a most significant bit of the current count (i.e., the registers are permitted to roll over to zero). In such an embodiment, the foot-mounted unit 102 and/or the wrist-mounted unit 104 may be left to determine when such a roll over has occurred.

Figure 27:
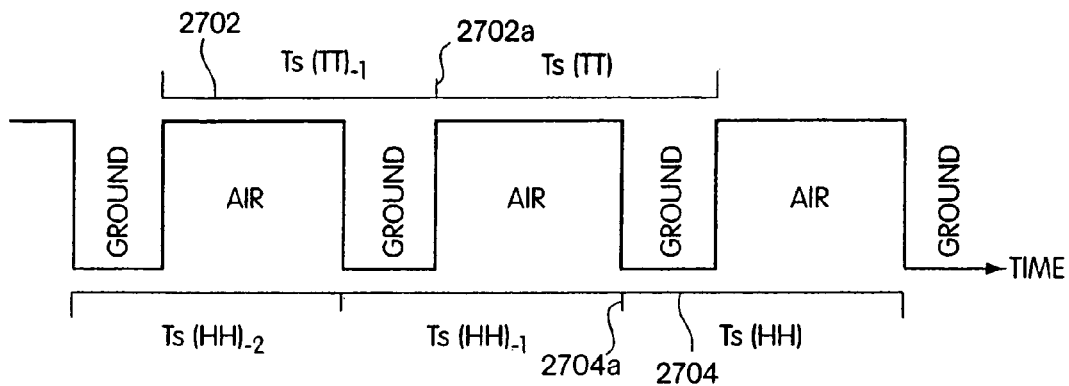
FIG. 27 is a timing diagram illustrating the symmetry between the step times of footsteps measured from toe lift-off to toe lift-off and from heel impact to heel impact during strides taken by a user.

FIG. 27 is a timing diagram illustrating how step time (Ts) measurements between consecutive toe-off events 704 and corresponding consecutive heel-off events 702 may be compared to ensure that each measured toe-off event 704 and each measured heel-off event 702 was identified accurately. In the example of FIG. 27, toe-off events 704 are indicated by hatch marks along the line 2702, e.g., the hatch mark 2702a. Two separate toe-to-toe step times (i.e., $Ts(TT)_{-1}$ and $Ts(TT)$) are labeled between respective pairs of the hatch marks on the line 2702. Similarly, heel-strike events 702 are indicated by hatch marks along the line 2704, e.g., the hatch mark 2704a. Three separate heel-to-heel step times (i.e., $Ts(HH)_{-2}$, $Ts(HH)_{-1}$, and $Ts(HH)$) are labeled between respective pairs of the hatch marks on the line 2704.

Figure 28:
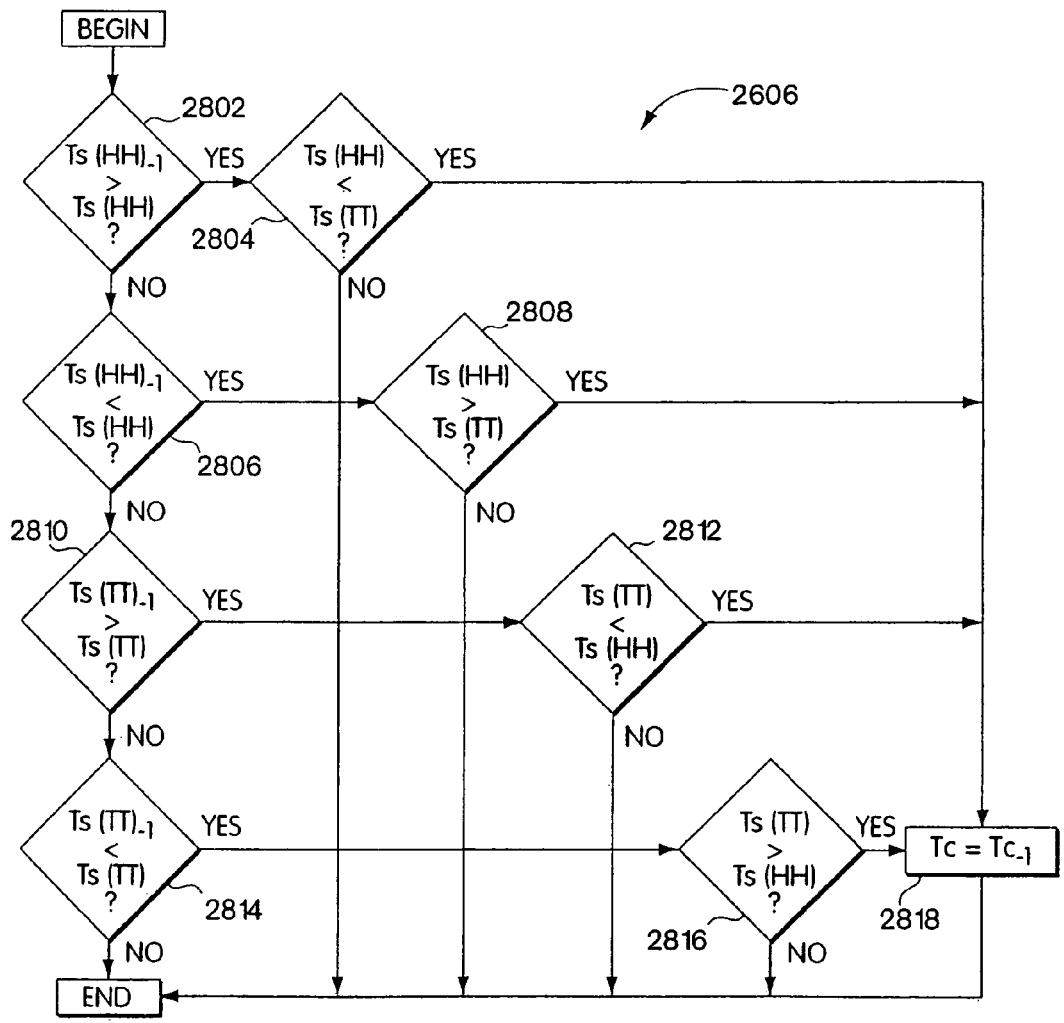
FIG. 28 is a flow diagram illustrating an example implementation of the "toe-to-toe & heel-to-heel Ts comparison and correction" routine shown in FIG. 26 during which data collected by the foot-mounted unit of FIGS. 1, 2, and 4 may be validated or corrected to ensure that it has the symmetry shown in FIG. 27.

FIG. 28 is a flow diagram of an illustrative implementation of the routine 2606 of the "smooth and calculate" routine 1416 (FIG. 26). During the routine 2606, heel-to-heel and toe-to-toe step times, such as those illustrated in FIG. 27, may be compared to verify the accuracy of the identified occurrences of the heel-strike events 702 and toe-off events 704 on which these values are based.

As shown in FIG. 28, the routine 2606 beings at a step 2802, wherein it is determined whether the heel-to-heel step time $Ts(HH)_{-1}$ is greater than the heel-to-heel step time $Ts(HH)$.

When, at the step 2802, it is determined that the heel-to-heel step time $Ts(HH)_{-1}$ is greater than the heel-to-heel step time Ts (HH), the routine 2606 proceeds to a step 2804, wherein it is determined whether the heel-to-heel step time $Ts(HH)$ is less than the toe-to-toe step time $Ts(TT)$.

When, at the step 2804, it is determined that the heel-to-heel step time $Ts(HH)$ is not less than the toe-to-toe step time $Ts(TT)$, the routine 2606 terminates.

When, at the step 2804, it is determined that the heel-to-heel step time $Ts(HH)$ is less than the toe-to-toe step time $Ts(TT)$, the routine 2606 proceeds to a step 2818, wherein the current value of Tc is replaced with the next most recent value of Tc. It should be appreciated that, when the questions asked by the steps 2802 and 2804 are both answered in the affirmative, a determination has been made that the heel-strike event 702 corresponding to the hatch mark 2704a in FIG. 27 was identified too late, and that the Tc value obtained with respect to this "late landing" should be replaced with a previously obtained "good" Tc value.

When, at the step 2802, it is determined that the heel-to-heel Ts value $Ts(HH)_{-1}$ is not greater than the heel-to-heel step value $Ts(HH)$, the routine 2606 proceeds to a step 2806, wherein it is determined whether the heel-to-heel step time $Ts(HH)_{-1}$ is less than the heel-to-heel step time $Ts(HH)$.

When, at the step 2806, it is determined that the heel-to-heel step time $Ts(HH)_{-1}$ is less than the heel-to-heel step time $Ts(HH)$, the routine 2606 proceeds to a step 2808, wherein it is determined whether the heel-to-heel step time $Ts(HH)$ is greater than the toe-to-toe step time $Ts(TT)$.

When, at the step 2808, it is determined that the heel-to-heel step time $Ts(HH)$ is not greater than the toe-to-toe step time $Ts(TT)$, the routine 2606 terminates.

When, at the step 2808, it is determined that the heel-to-heel step time $Ts(HH)$ is greater than the toe-to-toe step time $Ts(TT)$, the routine 2606 proceeds to the step 2818, wherein the current value of Tc is replaced with the next most recent value of Tc. It should be appreciated that, when the questions asked by the steps 2806 and 2808 are both answered in the affirmative, a determination has been made that the heel-strike event 702 corresponding to the hatch mark 2704a in FIG. 27 was identified too early, and that the Tc value obtained with respect to this "early landing" should be replaced with a previously obtained "good" Tc value.

When, at the step 2806 (discussed above), it is determined that the heel-to-heel step time $Ts(HH)_{-1}$ is not less than the heel-to-heel step time $Ts(HH)$, the routine 2606 proceeds to a step 2810, wherein it is determined whether the toe-to-toe step time $Ts(TT)_{-1}$ is greater than the toe-to-toe step time $Ts(TT)$.

When, at the step 2810, it is determined that the toe-to-toe step time $Ts(TT)_{-1}$ is greater than the toe-to-toe step time $Ts(TT)$, the routine 2606 proceeds to a step 2812, wherein it is determined whether the toe-to-toe step time Ts(TT) is less than the heel-to-heel step time Ts(HH).

When, at the step 2812, it is determined that the toe-to-toe step time Ts(TT) is not less than the heel-to-heel step time Ts(HH), the routine 2606 terminates.

When, at the step 2812, it is determined that the toe-to-toe step time Ts(TT) is less than the heel-to-heel step time Ts(HH), the routine 2606 proceeds to the step 2818, wherein the current value of Tc is replaced with the next most recent value of Tc. It should be appreciated that, when the questions asked by the steps 2810 and 2812 are both answered in the affirmative, a determination has been made that the toe-off event corresponding to the hatch mark 2702a in FIG. 27 was identified too late, and that the Tc value obtained with respect to this "late takeoff" should be replaced with a previously obtained "good" Tc value.

When, at the step 2810 (discussed above), it is determined that the toe-to-step time $Ts(TT)_{-1}$ is not greater than the toe-to-toe step time Ts(TT), the routine 2606 proceeds to a step 2814, wherein it is determined whether the toe-to-toe step time $Ts(TT)_{-1}$ is less than the toe-to-toe step time Ts(TT).

When, at the step 2814, it is determined that the toe-to-toe step time $Ts(TT)_{-1}$ is less than the toe-to-toe step time Ts(TT), the routine 2606 proceeds to a step 2816, wherein it is determined whether the toe-to-toe step time Ts(TT) is greater than the heel-to-heel step time Ts(HH).

When, at the step 2816, it is determined that the toe-to-toe step time Ts(TT) is not greater than the heel-to-heel step time Ts(HH), the routine 2606 terminates.

When, at the step 2816, it is determined that the toe-to-toe step time Ts(TT) is greater than the heel-to-heel step time Ts(HH), the routine 2606 proceeds to the step 2818, wherein the current value of Tc is replaced with the next most recent value of Tc. It should be appreciated that, when the questions asked by the steps 2814 and 2816 are both answered in the affirmative, a determination has been made that the toe-off event corresponding to the hatch mark 2702a in FIG. 27 was identified too early, and that the Tc value obtained with respect to this "early takeoff" should be replaced with a previously obtained "good" Tc value.

When, at the step 2814 (discussed above), it is determined that the toe-to-toe step time $Ts(TT)_{-1}$ is not less than the toe-to-toe step time Ts(TT), the routine 2606 terminates.

Figure 29A:
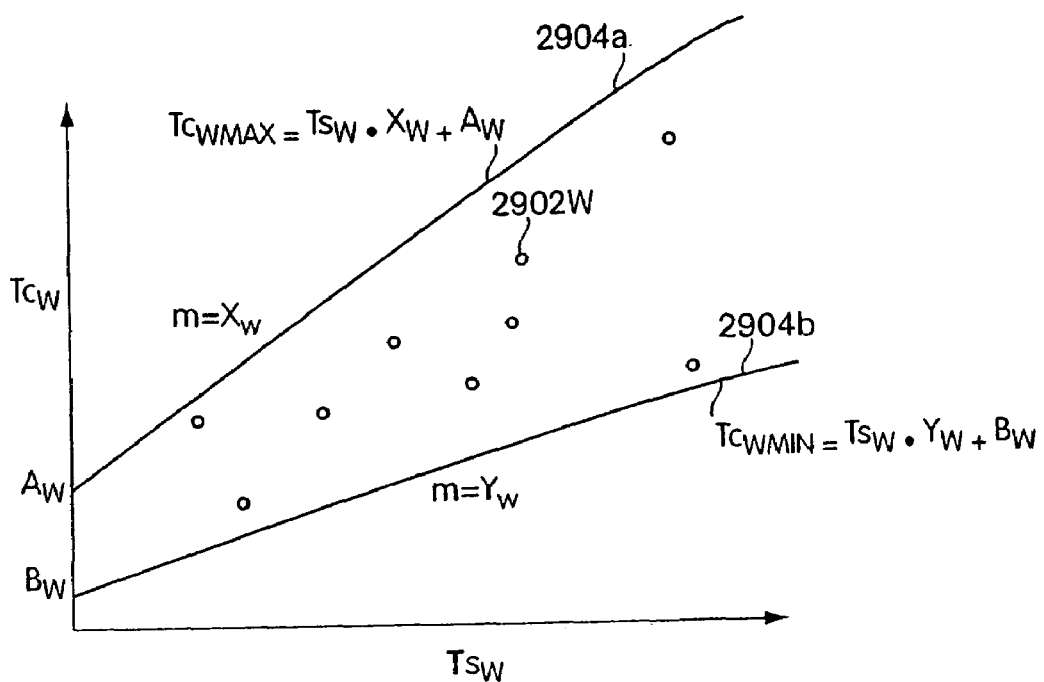
FIGS. 29A and 29B are graphs illustrating acceptable ranges for the ratios of foot contact times and step times (Tc/Ts) for data accumulated while a user is walking or running.
Figure 29B:
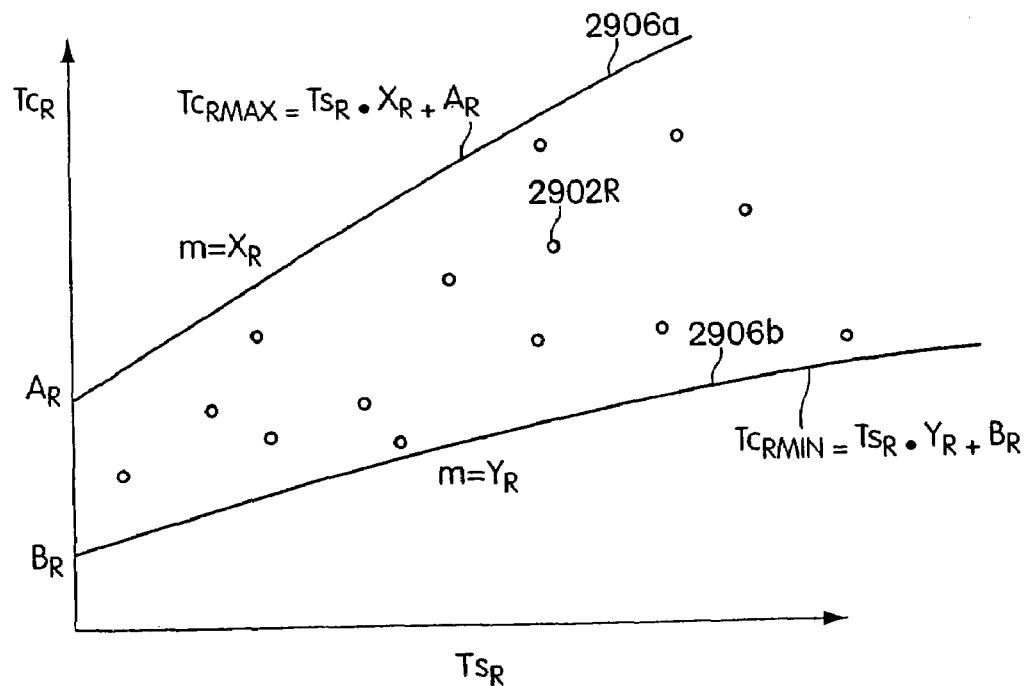

FIGS. 29A and 29B are graphs representing, respectively, ratios of the values of Tc and Ts measured for multiple individuals throughout a variety of walking and running speeds. Based upon empirical measurements, we have discovered that, when a user is walking, each of the measured ratios of $Tc_W$ to $Ts_W$ (e.g., each of the points 2902W) tends to fall between a first pair of lines identified by respective equations involving $Tc_W$ and $Ts_W$. Similarly, we have discovered that, when a user is running, each of the measured ratios of $Tc_R$ to $Ts_R$ (e.g., each of the points 2902R) tends to fall between a second pair of lines identified by respective equations involving $Tc_R$ and $Ts_R$.

In light of these discoveries, in one embodiment of the invention, for each footstep taken by the user 112, the ratio of Tc to Ts is checked to make sure it falls within the bounds identified by these lines. That is, for Tc values in the walking range (e.g., above 420 milliseconds), each measured ratio of $Tc_W$ to $Ts_W$ is checked to make sure it falls between the lines 2904a and 2904b of FIG. 29A. Similarly, for Tc values in the walking range (e.g., less than 420 milliseconds), each measured ratio of $Tc_R$ to $Ts_R$ is checked to make sure it falls between the lines 2906a and 2906b of FIG. 29B. Each of the Tc and Ts values also may be separately checked to ensure that, by itself, it falls within a reasonable range for such values. As shown, the lines 2904a and 2904b may be defined by the equations $Tc_{WMAX}=Ts_W*X_W+A_W$ and $Tc_{WMIN}=Ts_W*Y_W+B_W$, respectively, wherein the values $X_W$ and $Y_W$ are slopes of the respective lines, and the values $A_W$ and $B_W$ are the respective Y-intercepts thereof. Similarly, as shown, the lines 2906a and 2906b may be defined by the equations $Tc_{RMAX}=Ts_R*X_R+A_R$ and $Tc_{RMIN}=Ts_R*Y_R+B_R$, respectively, wherein the values $X_R$ and $Y_R$ are slopes of the respective lines, and the values $A_R$ and $B_R$ are the respective Y-intercepts thereof.

Figure 30:
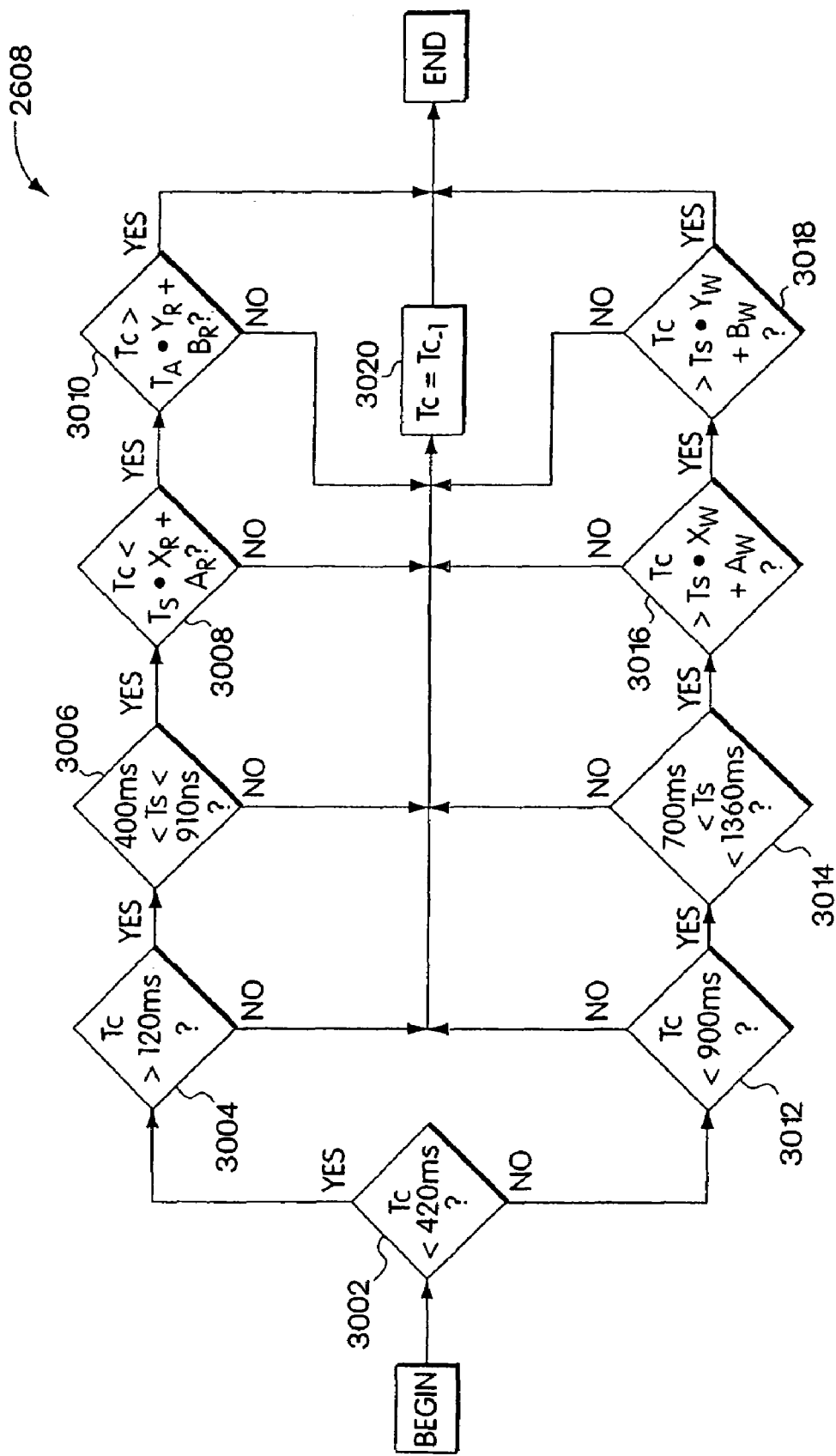
FIG. 30 is a flow diagram illustrating an example implementation of the "Tc, Ts & Tc/Ts bounds checking" routine shown in FIG. 26 during which each measured foot contact time (Tc) and step time (Ts), as well as the ratio of each foot contact time to its corresponding step time (Tc/Ts), may be validated or replaced to ensure that these values fall within the acceptable ranges therefor illustrated in FIGS. 29A-B.

FIG. 30 is a flow diagram illustrating an example implementation of the routine 2608 of the "smooth and calculate" routine 1416 shown in FIG. 26. Pursuant to the routine 2608, the values of Tc and Ts are checked individually to ensure that each falls within an acceptable range, and each ratio of these two values is checked as well to ensure that it falls within the bounds of the lines discussed above.

As shown, the routine 2608 begins at a step 3002, wherein it is determined whether the measured Tc value is less than "420" milliseconds.

When, at the step 3002, the measured Tc value is determined to be less than "420" milliseconds, it is determined that the user 112 is running, and the routine 2608 proceeds to a step 3004, wherein it is determined whether the measured Tc value is greater than "120" milliseconds.

When, at the step 3004, it is determined that the Tc value is not greater than "120" milliseconds, it is determined that the Tc value is outside of the acceptable range for Tc values for running, and the routine 2608 proceeds to a step 3020, wherein the measured Tc value is replaced with the next most recent Tc value, and the routine 2608 then terminates.

When, at the step 3004, it is determined that the measured Tc value is greater than "120" milliseconds, the routine 2608 proceeds to a step 3006, wherein it is determined whether the measured Ts value is between "400" and "910" milliseconds (i.e., an acceptable range of Ts values for running).

When, at the step 3006, it is determined that the measured Ts value is not between "400" and "910" milliseconds, it is determined that the Ts value is outside of the acceptable range for Ts values for running, and the routine 2608 proceeds to the step 3020, wherein the measured Tc value is replaced with the next most recent Tc value, and the routine 2608 then terminates.

When, at the step 3006, it is determined that the measured Ts value is between "400" and "910" milliseconds, the routine 2608 proceeds to steps 3008 and 3010, wherein it is determined whether the ratio of the measured Tc and Ts values falls between "running" lines 2906a and 2906b of FIG. 29.

When, at the steps 3008 and 3010, it is determined that the ratio of the measured Tc and Ts values falls above the line 2906a (step 3008) or below the line 2906b (step 2910), the routine 2608 proceeds to the step 3020, wherein the measured Tc value is replaced with the next most recent Tc value, and the routine 2608 then terminates.

When, at the steps 3008 and 3010, it is determined that the ratio of the measured Tc and Ts values falls both below the line 2906a (step 3008) and above the line 2906b (step 2910), the routine 2608 terminates.

When, at the step 3002 (described above), it is determined that the measured Tc value is not less than "420" milliseconds, it is determined that the user 112 is walking, and the routine 2608 proceeds to a step 3012, wherein it is determined whether the measured Tc value is less than "900" milliseconds.

When, at the step 3012, it is determined that the measured Tc value is not greater than "900" milliseconds, it is determined that the Tc value is outside of the acceptable range for Tc values for walking, and the routine 2608 proceeds to the step 3020, wherein the measured Tc value is replaced with the next most recent Tc value, and the routine 2608 then terminates.

When, at the step 3012, the measured Tc value is determined to be less than "900" milliseconds, the routine 2608 proceeds to a step 3014, wherein it is determined whether the measured Ts value is between "700" and "1360" milliseconds (i.e., an acceptable range of Ts values for walking).

When, at the step 3014, it is determined that the measured Ts value is not between "700" and "1360" milliseconds, the routine 2608 proceeds to the step 3020, wherein the measured Tc value is replaced with the next most recent Tc value, and the routine 2608 then terminates.

When, at the step 3014, it is determined that the measured Ts value is between "700" and "1360" milliseconds, the routine 2608 proceeds to steps 3016 and 3618, wherein it is determined whether the ratio of the measured values of Tc and Ts falls between the lines 2906a and 2906b of FIG. 29.

When, at the steps 3016 and 3018, it is determined that the ratio of the measured values of Tc and Ts falls above the line 2906a (step 3016) or falls below the line 2906b (step 3018), the routine 2608 proceeds to the step 3020, wherein the measured Tc value is replaced with the next most recent Tc value, and the routine 2608 then terminates.

When, at the steps 3016 and 3018, it is determined that the ratio of the measured values of Tc and Ts falls both below the line 2906a (step 3016) and above the line 2906b (step 3018), the routine 2608 terminates.

Figure 31:
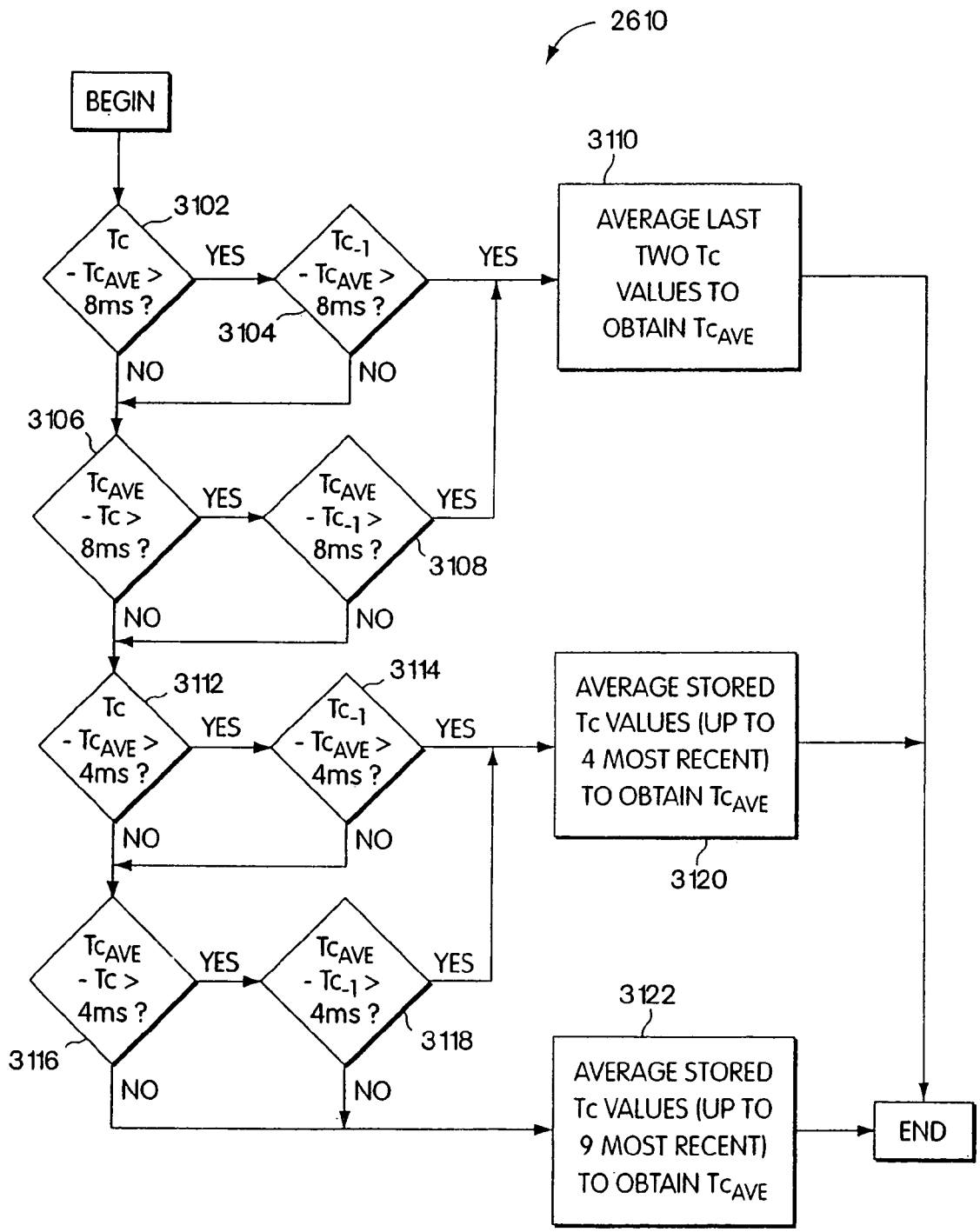
FIG. 31 is a flow diagram illustrating an example implementation the "$Tc_{AVE}$ calculation" routine shown in FIG. 26 during which an average foot contact time value ($Tc_{AVE}$) over several footsteps taken by the user may be calculated in a manner depending on the rate at which the measured foot contact time (Tc) values are increasing or decreasing.

FIG. 31 is a flow diagram showing an illustrative implementation of the routine 2610 of the "smooth and calculate" routine 1416 shown in FIG. 26. As shown, the routine 2610 begins at steps 3102 and 3104, wherein it is determined whether the current Tc value and the next most recent Tc value are each more than eight seconds greater than the currently-stored value of $Tc_{ave}$ (i.e., the average value of Tc over the last several steps).

When, at the steps 3102 and 3104, it is determined that the current Tc value and the next most recent Tc value are each more than eight seconds greater than the currently-stored value of $Tc_{ave}$, the routine 2610 proceeds to a step 3110, wherein the two most recent Tc values obtained (including the current Tc value) are averaged to obtain a new value of $Tc_{ave}$, and the routine 2610 then terminates.

When, at the steps 3102 and 3104, it is determined that either the current Tc value or the next most recent Tc value is not more than eight milliseconds greater than the currently-stored value of $Tc_{ave}$, the routine 2610 proceeds to steps 3106 and 3108, wherein it is determined whether the current Tc value and the next most recent Tc value are each more than eight milliseconds less than the currently-stored value of $Tc_{ave}$.

When, at the steps 3106 and 3108, it is determined that both the current Tc value and the next most recent value are each more than eight milliseconds less than the currently-stored value of $Tc_{ave}$, the routine 2610 proceeds to the step 3110, wherein the two most recent Tc values are averaged to obtain a new value of $Tc_{ave}$, and the routine 2610 then terminates.

Therefore, the steps 3102-3108 ensure that, if at least two Tc values suddenly deviate from a current value of $Tc_{ave}$ by more than eight milliseconds, the value of $Tc_{ave}$ will be updated using only the two most recent values of Tc. This technique ensures that the value of $Tc_{ave}$ responds quickly to a new pace of the user 112 so that the user can receive instant feedback regarding the same.

When, at the steps 3106 and 3108, it is determined that either the current Tc value or the next most recent Tc value is not more than eight milliseconds less than the currently-stored value of $Tc_{ave}$, the routine 2610 proceeds to steps 3112 and 3114, wherein it is determined whether the current Tc value and the next most recent Tc value are each more than four milliseconds greater than the currently-stored value of $Tc_{ave}$.

When, at the steps 3112 and 2114, it is determined that the current Tc value and the next most recent Tc value are each more than four milliseconds greater than the currently-stored value of $Tc_{ave}$, the routine 2610 proceeds to a step 3120, wherein up to four of the most recent Tc values are averaged to obtain a new value of $Tc_{ave}$, and the routine 2610 then terminates.

When, at the steps 3112 and 3114, either the current Tc value or the next most recent Tc value is determined to not be more than four milliseconds greater than the currently-stored value of $Tc_{ave}$, the routine 2610 proceeds to steps 3116 and 3118, wherein it is determined whether the current Tc value and the next most recent Tc value are each more than four milliseconds less than the currently-stored value of $Tc_{ave}$.

When, at the steps 3116 and 3118, is determined that the current Tc value and the next most recent Tc value are each more than four milliseconds less than the currently-stored value of $Tc_{ave}$, the routine 2610 proceeds to the step 3120, wherein up to the four most recent Tc values are averaged to obtain a new value of $Tc_{ave}$, and the routine 2610 then terminates.

When, at the steps 3116 and 3118, it is determined that either the current Tc value or the next most recent Tc value is not more than four milliseconds less than the currently-stored value of $Tc_{ave}$, the routine 2610 proceeds to a step 3122, wherein up to nine of the most recent Tc values are averaged to obtain a new value of $Tc_{ave}$, and the routine 2610 then terminates.

Based upon the above, it should be appreciated that the routine 2610 ensures that the value $Tc_{ave}$ will be updated at a rate commensurate with the rate at which the Tc values being measured are changing. In this manner, when the value $Tc_{ave}$ is used to calculate the instantaneous pace of a user in locomotion on foot, the pace displayed to the user 112 may respond quickly to sudden changes in the user's pace, but may also be "smoothed" over several footsteps when the user's pace is relatively steady.

FIGS. 32A-H each shows the front face 308 of the wrist-mounted unit 104. In each of FIGS. 32A-H, the display 412 of the wrist-mounted unit 104 has simultaneously displayed thereon a respective combination of parameters. Any or all of these combinations of parameters may be made available to the user 112, and the user 112 may select (e.g., by pushing one or more of the buttons 306b-e) which combination is displayed at a given time. In one illustrative embodiment of the invention, the user may use the computer 428 (e.g., using software running on the computer 428 and/or the network server 442) to select the combination of parameters to be displayed on the display 412, and information relating to the user's selection may then be selectively or automatically transmitted to the wrist and/or foot mounted units, e.g., via an RF communication channel. It should be appreciated that any other parameters or information relating to the operation of the wrist-mounted unit 104 and/or the foot-mounted unit 102 (some of which are described herein) may also be generated by the user via the computer 428 and transmitted to the appropriate unit(s) in this manner.

In one illustrative embodiment of the invention, the display 412 has simultaneously displayed thereon at least one determined performance parameter of the user (e.g., pace) and at least one determined variable physiological parameter of the user (e.g., heart rate), each of which may be determined, for example, using the techniques and devices described elsewhere herein. As used herein, "variable physiological parameter" refers to any physiological condition of a user's body that may experience a measurable change when the user is exercising, and is intended to encompass parameters such as heart rate, respiration rate, body temperature, lactate level, etc. The term "variable physiological parameter" is not intended to encompass static physiological parameters such as weight, height, etc. As used herein, "performance parameter" refers to any measurable amount, level, type or degree of physical activity engaged in by the user, and is intended to encompass parameters such as foot contact time, foot loft time, step time, instantaneous speed, average speed, instantaneous pace, average pace, energy expenditure rate, total energy expenditure, distance traveled, etc.

In the first example (FIG. 32A), the display 412 of the wrist-mounted unit 104 has displayed thereon: (a) the instantaneous pace of the user, (b) the average pace of the user during a particular outing, (c) the distance traveled by the user during the outing, and (d) a chronograph indicating the time that has elapsed during the outing. The advantages of simultaneously displaying these particular parameters are numerous, especially for a runner engaged in a competition, e.g., a marathon, a 10 K, or the like. For example, during a race, the user 112 may increase or decrease his or her current pace based upon the displayed value of the user's average pace thus far during the race. In this manner, the user 112 may ensure that the overall average pace for the completed race is close to a predetermined target value.

Figure 32A:
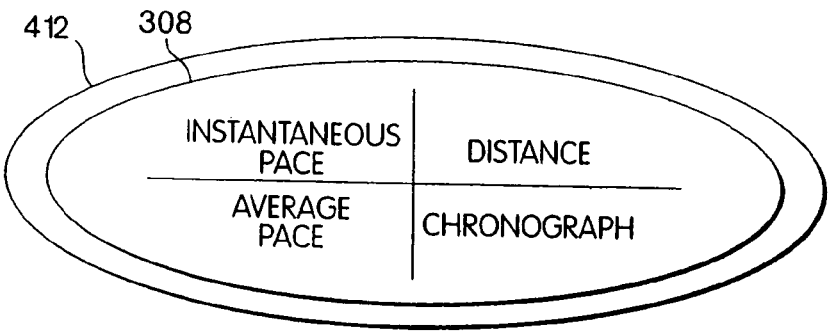
FIGS. 32A-H illustrate examples of respective combinations of parameters that may be displayed on the display of the wrist-mounted unit shown in FIGS. 1, 3, and 4 in accordance with one embodiment of the invention.
Figure 32B:
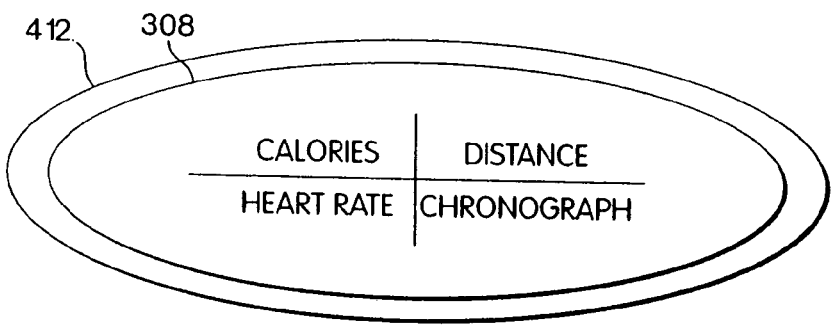

In lieu of a numeric display, this same advantage may be achieved, for example, using two so-called "pace fans" akin to the hands on a wristwatch. For example, one fan (e.g., a watch hand) may maintain an angular orientation indicative of the user's current pace, and the other fan may maintain an angular orientation indicative of the user's average pace. As yet another alternative, side-by-side graduated bar graphs may be displayed to the user, with the height of each bar graph corresponding to a respective one of the user's current pace and the user's average pace. The benefits of displaying the chronograph value and the distance traveled by the user, both separately and in combination with the other units in the example of FIG. 32A, are apparent and therefore will not be discussed further.

In the next example (FIG. 32B), the display 412 of the wrist-mounted unit 104 has displayed thereon: (a) the total calories expended during an outing, (b) the distance traveled by the user during the outing, (c) the current heart rate of the user (or average heart rate of the user during the outing), and (d) a chronograph indicating the total time that has elapsed during the outing.

Figure 32C:
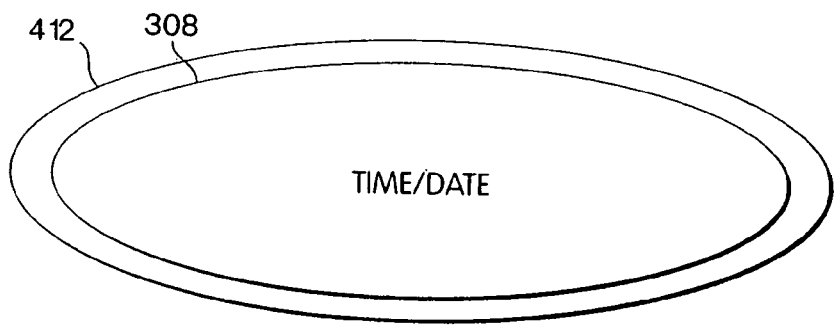
Figure 32D:
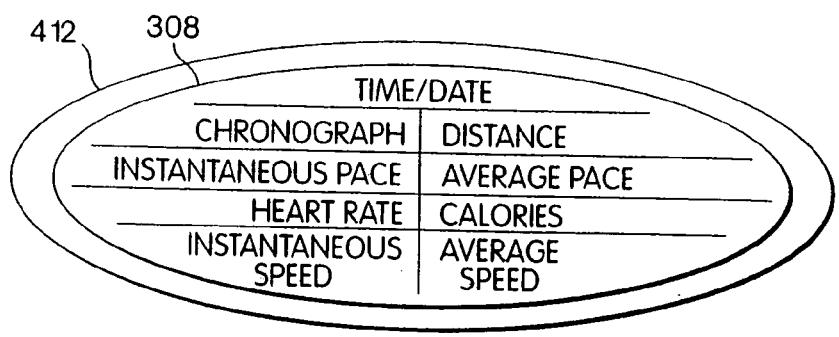

In the example of FIG. 32C, only the time and date are displayed. The user may, for example, selectively choose this display combination when the user is engage in non-athletic activities, and simply wants a typical wrist-watch display.

In the next example (FIG. 32D), the display 412 of the wrist-mounted unit 104 has displayed thereon: (a) a chronograph indicating the total time that has elapsed during the outing, (b) the distance traveled by the user during the outing, (c) the instantaneous pace of the user, (d) the average pace of the user during the outing, (e) the current heart rate of the user (or the average heart rate of the user during the outing), (f) the total calories expended by the user during the outing, (g) the instantaneous speed of the user, and (h) the average speed of the user during the outing.

Figure 32E:
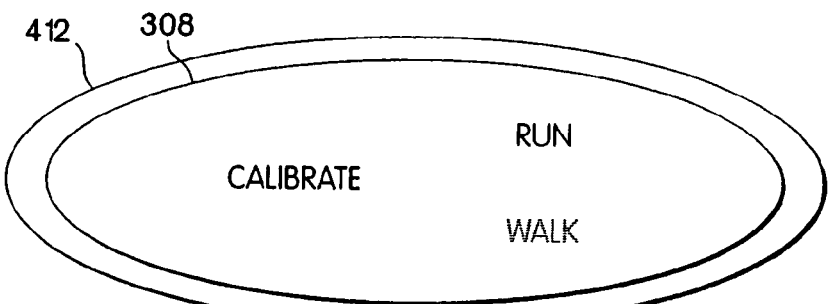

In the example of FIG. 32E, the display 412 has displayed thereon an indication that a calibration procedure has been selected. Also displayed is an indication as to whether a "walk" calibration or a "run" calibration has been selected. In this mode, the user may start and stop a calibration procedure (e.g., by depressing one or more of the buttons 306*b-e*) during which the calibration constants discussed above may be determined.

Figure 32F:
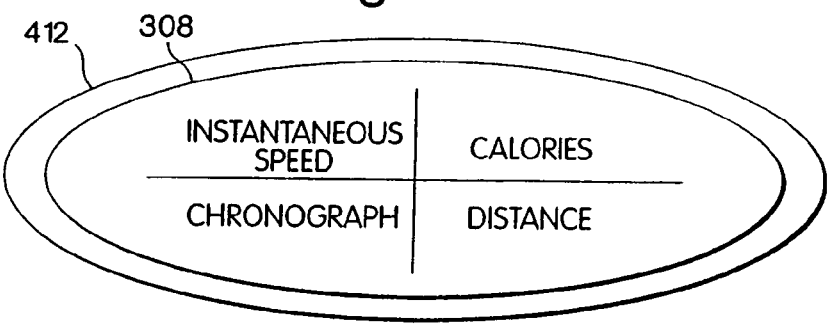

In the example of FIG. 32F, the display 412 of the wrist-mounted unit 104 has displayed thereon: (a) the instantaneous speed of the user, (b) the calories expended by the user during the outing, (c) a chronograph indicating the total time that has elapsed during the outing, and (d) the distance traveled by the user during the outing.

Figure 32G:
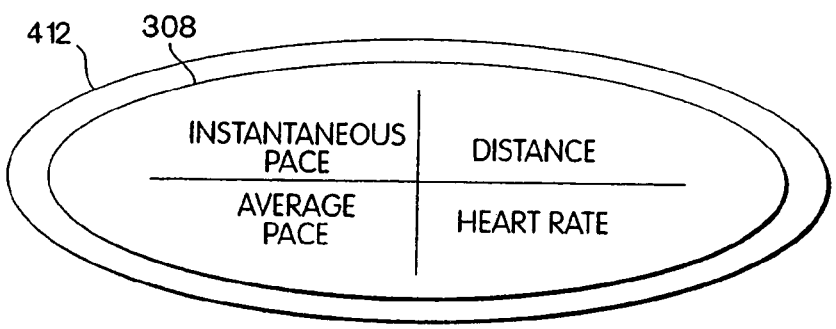

In the example of FIG. 32G, the display 412 of the wrist-mounted unit 104 has displayed thereon: (a) the instantaneous pace of the user, (b) the distance traveled by the user during the outing, (c) the average pace of the user during the outing, and (d) the current heart rate of the user.

Figure 32H:
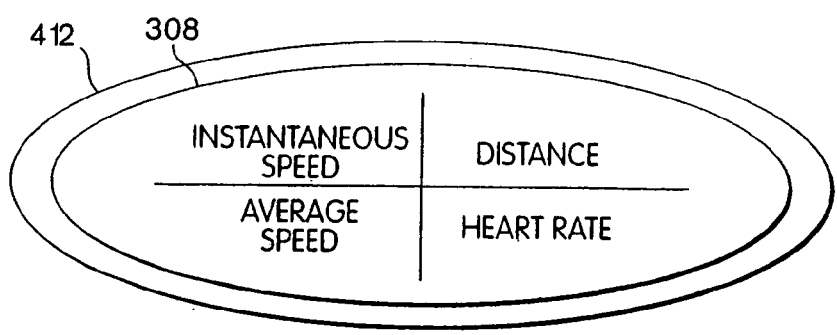

Finally, in the example of FIG. 32H, the display 412 of the wrist-mounted unit 104 has displayed thereon: (a) the instantaneous speed of the user, (b) the distance traveled by the user during the outing, (c) the average speed of the user during the outing, and (d) the current heart rate of the user.

With regard to the displayable values discussed above in connection with FIGS. 32A-H, it should be appreciated that any of the values that are described as being monitored and displayed during a particular outing may additionally or alternatively be monitored and displayed during multiple outings. That is, the value displayed may alternatively be the cumulative total or overall average value for each of the several outings. For example, the distance displayed may represent the distance traveled by the user 112 during all "runs" engaged in by the user 112 during a week, a month, a year, etc., or the average pace displayed may represent the average pace of the user 112 during all "runs" engaged in by the user 112 during a week, a month, a year, etc.

In addition, it should be appreciated that any or all of the parameters described as being displayable may additionally or alternatively be displayed on a display on the foot-mounted unit 102, or on a display disposed remote from the user 112, e.g., the computer 428 or another display (not shown) held by a track coach or the like. Other examples of parameters that may be displayed on the wrist-mounted unit 104 and/or the foot-mounted unit 102, either together with or separately from the examples shown in FIGS. 32A-H, include cadence (stride rate), stride length, and acceleration. Illustrative techniques for determining and displaying each of these parameters are discussed elsewhere herein.

In one illustrative embodiment of the invention, the ARC processor 410 in the wrist-mounted unit 104 is configured (e.g., by instructions stored in the memory 404) to calculate time "splits" automatically on a per-unit-distance basis (e.g., per mile or kilometer). For example, the ARC processor 410 may calculate a time split for each of the twenty six miles of a marathon. Such splits may be displayed to the user 112 during the event and/or may be stored in memory for later retrieval and analysis and/or display. Because information regarding total distance traveled and a chronograph are both maintained in the wrist-mounted unit. 104, such splits may readily be calculated by automatically recording the time of the chronograph each time a split distance is reached. Of course, splits may alternatively be determined using the foot-mounted unit 102, or another device in the system that receives the necessary information. When the foot-mounted unit 102 is used to calculate splits, the foot-mounted unit 102 can display the split information itself and/or it can transmit the information to the wrist-mounted unit 104 for display.

In one illustrative embodiment, in addition to being given information regarding the last split completed, the user can also be provided with feedback regarding progress on the split currently being measured. For example, the user may be provided with an indication regarding the user's average pace since the last split, or the projected time for the current split based upon the user's average pace since the last split.

In one embodiment of the invention, one or more of the devices in the system (i.e., the foot-mounted unit 102, the wrist-mounted unit 104, the computer 428, and/or the network server 442) may be used to determine whether the speed, pace and/or heart rate of the user 112 are within particular zones. As used herein, the term "zone" refers to a range of values bounded by at least one threshold. Therefore, unless otherwise specified, zone may refer to any one of: (1) all values greater than a certain value, (2) all values less than a certain value, and (3) all values falling between two different values. If it is determined that one or more of the monitored parameters falls outside the particular zone therefor, an output may be generated by the processor performing the monitoring. This output may, for example, cause information representing the same to be stored in memory to later provide feedback to the user 112, or it may cause an output that is perceptible to the user to be generated so that the user is provided with immediate feedback. When employed, any of a number of outputs perceptible to the user 112 may be used, and the invention is not limited to any particular type of perceptible output. Examples of suitable output devices include: audio indicators such as buzzers, chimes, or voice synthesizers; visual indicators such as those capable of displaying numbers, text, symbols, and/or lights; and physical indicators such as vibrators.

When immediate feedback is provided to the user 112, the user may, in response to such feedback, adjust his or her workout, if necessary, to bring the monitored parameter(s) back into the particular zone(s). The user 112 may, for example, preset the zone(s) prior to beginning a workout, and/or may adjust the zones (or even disable the zone monitoring function entirely, or perhaps only the feedback functionality thereof) during the workout if he or she desires a more or less intense workout. In one illustrative embodiment, the user 112 may "program" a particular zone-specific workout, during which zones are adjusted automatically during the workout in response to time and/or distance measurements. For example, the user may program a workout during which a first zone (e.g., a warm up zone) is set during a first time period or distance interval, a second zone (e.g., a workout zone) is set during a second time period or distance interval, and a third zone (e.g., a cool down zone) is set during a third time period or distance interval. In another example, the user may set zones on a per-mile or per-minute basis so as to perform interval training. The number of possibilities of zone adjustments in response to distance and/or time goals being met is virtually without limit, and the user may preset his or her workout to his or her particular tastes or needs. It should be appreciated that, when both heart rate and speed or pace are monitored simultaneously, negative feedback (i.e., an indication that workout intensity should be increased) may be provided only in response to one or more combinations of the monitored parameters falling outside of the preset zones. For example, during a particular time period or distance interval, negative feedback may be provided to the user only when both heart rate or speed/pace fall outside the preset zones therefor.

In one illustrative embodiment, the wrist-mounted unit 104 and/or the foot-mounted unit 102 can be programmed so as to provide the user with feedback in response to one or more particular distances being traveled or in response to one or more time periods elapsing during a workout. Such time periods and/or distances may, for example, be preprogrammed or selected by the user. For example, a perceptible indication may be provided to the user 112 each time the user 112 has traveled a mile or each time the user 112 has been running or walking for an additional ten minutes. This sort of feedback can enables the user to monitor the progress of his or her workout, and to be reminded as to the progress in achieving a certain goal, e.g., to run ten miles or to walk for one hour. Alternatively, the user may program the wrist-mounted unit 104 and/or the foot-mounted unit 102 such that feedback is provided when each of several different time and/or distance intervals are completed. For example, during a workout, the user may be provided with a first perceptible indication after a "warm up" distance has been completed or after a "warm up" time period has elapsed, may be provided with a second perceptible indication after a "workout" distance has been completed or after a "workout" time period has elapsed, and may be provided with a third perceptible indication after a "cool-down" distance has been completed or after a "cool-down" time period has elapsed. A perceptible indication may also be provided to the user instructing the user to rest (i.e., slow down considerably or stop exercising completely) during one or more particular time intervals or following one or more particular distance intervals.

In one illustrative embodiment, the user may program the wrist-mounted unit 104 and/or the foot-mounted unit 102 with a predetermined distance to be achieved during an outing, as well as an indication as to how the user desires to receive feedback during the race. For example, the user may enter a certain goal distance (e.g., five miles), and request to be given feedback each time a certain fraction (e.g., one-fourth) of the goal distance has been completed. If the fraction is chosen to be one-half, the user may complete an "out and back" walk or run (i.e., an outing during which the user travels back and forth along the same path) of a certain distance, and may be given a perceptible indication as to exactly when to turn around and go in the opposite direction.

In one embodiment, the user may program the foot-mounted unit 102 and/or the wrist-mounted unit 104 with information regarding a distance to be traveled during an outing, and one or both of (1) a goal time in which the user wishes to complete the distance, and (2) a goal average speed or pace the user wishes to achieve during the outing. Based upon this information, as well as a measured distance traveled during the outing, the user can be provided with real-time feedback regarding future performance during the outing that is required for the user to achieve the input goal(s), e.g., the average speed or pace required during the remainder of the race in order to achieve the input goal(s). In addition, based upon an input goal distance, the measured elapsed time during an outing, the measured distance traveled thus far during the outing, and the measured current pace of the user, the user also can be provided with feedback regarding a projected time in which the user will complete the goal distance if the user maintains his or her current pace. Many other forms of feedback using one or more other combinations of such input and measured parameters also are possible in connection with different embodiments of the invention, and the invention is not limited to any particular form of feedback.

As discussed above in connection with FIG. 8, in one embodiment of the invention, the foot-mounted unit 102 and/or the wrist-mounted unit can readily determine whether the user 112 is walking or running during each footstep taken by the user. Therefore, in such an embodiment, the user may program the foot-mounted unit 102 and/or the wrist-mounted unit 104 such that the user is instructed to walk or run during certain distance and/or time intervals. When so programmed, the device may provide a perceptible indication to the user that the user should be running or walking, if the user is walking when he or she should be running, or vice versa. Any variety and/or number of interval lengths during which the user should walk and run during an outing may be programmed. In one embodiment, the respective total amounts of time that the user walks and runs during an outing is displayed to the user and/or stored in memory for later use. Such feedback to the user may help the user optimize a workout, for example, if the user wishes to walk and run equal distances during an outing. Ratios of "walk time" to "run time" and/or "walk distance" to "run distance," or other ratios of such values, may also be calculated and displayed to the user and/or stored in memory for later use.

As discussed above, one way the user can program workouts or input parameters such as those discussed above is to use software executing on the computer 428 and/or the network server 442 to preset the parameters for his or her workout, and then cause the programmed information to be transmitted to the wrist-mounted unit 104 and/or the foot-mounted unit 102.

In embodiments of the invention wherein both the heart rate (HR) and foot contact times of a user are measured, a pair of so-called "fitness indexes" (one for walking and one for running) may be calculated by a processor receiving this information. The fitness indexes (FI) for a particular user may, for example, be calculated according to the following equations:

$$FI_W = HR * Tc_W \quad FI_R = HR * Tc_R \tag{27}$$

Significantly, we have discovered that the values of a user's "walking" fitness index ($FI_W$) and "running" fitness index ($FI_R$) are substantially unaffected by changes in the user's speed when the user is walking and running, respectively. That is, as a user's speed increases, the amount that the user's heart rate (HR) increases tends to offset the amount that the value of Tc decreases, so that the product of the two variables remains substantially constant. Similarly, as a user's speed decreases, the amount that the user's heart rate decreases tends to offset the amount that the value of Tc increases.

In one embodiment of the invention, an average fitness index ($FI_{AVE}$) for a user 112 is calculated each time the user walks or runs for a particular period of time, and the value of this average fitness index ($FI_{AVE}$) may be used as an indicator of the user's physical fitness level. A user's average fitness index ($FI_{AVE}$) for a particular outing may be calculated, for example, by multiplying each foot contact time (Tc) value obtained during the outing by the user's heart rate (HR) at the time that the foot contact time (Tc) value is measured, and maintaining a running sum of all such products of Tc and HR. The running sum then may be divided by the total number of foot contact time (Tc) values obtained during the outing to yield the average fitness index value.

The calculated average fitness index value ($FI_{AVE}$) may, for example, be calculated and/or displayed on the wrist-mounted unit 104, the foot-mounted unit 102, and/or another device such as a personal computer linked to the foot-mounted unit 102 and/or the wrist-mounted unit 104 via a wireless communication link. The fitness index value may be displayed simultaneously with any of the other "displayable" information discussed above in connection with FIGS. 32A-H, or may be displayed separately therefrom.

Given the relationships between foot contact time (Tc) and other performance parameters (e.g., pace, speed, energy expenditure, etc.) that are either described herein or are known in the art, we have recognized that other equations including both heart rate and one or more of such other performance parameters as variables therein would, when the variables are properly combined, likewise yield a constant value. Therefore, such other performance parameters may be used in lieu of or in addition to measured foot contact times in an equation used to calculate a fitness index (FI) value. For example, a fitness index (FI) value may be obtained using an equation having both: (1) heart rate (HR), and (2) any one of Speed, Pace, and energy expenditure as variables therein. In this regard, it should be appreciated that, to the extent that other techniques may be used to obtain such other performance parameters (i.e., techniques other than measuring foot contact times and calculating the performance parameters based thereon), such other techniques may be used to obtain values of one or more of these performance parameters, and a fitness index may be calculated based thereupon. Therefore, in some embodiments, a fitness index value may be obtained without requiring the measurement of foot contact times. In the illustrative embodiment described herein, the measurement of foot contact times and/or other performance parameters, and the calculation of a fitness index based thereupon, are performed by one or more devices that are ambulatory (i.e., may be supported by the user while the user is in locomotion on foot).

Significantly, once a fitness index value is determined for a particular user, the user's heart rate can be estimated based solely upon one or more measured foot contact times of the user, or based upon one of the other measured performance parameters discussed above. This may be accomplished, for example, by rewriting the equations (27) as follows:

$$HR = FI_W / Tc_W \quad HR = FI_R / Tc_R \tag{28}$$

Using the equations (28), the user's instantaneous heart rate HR can be estimated by: (1) measuring a foot contact time during a footstep taken by the user, (2) determining whether the user was walking or running when the foot contact time was measured, and (3) including the measured foot contact time in an appropriate one of the equations (28) (depending on whether the user was walking or running) along with the previously-determined average fitness index value ($FI_{AVE}$). Therefore, in one embodiment of the invention, an ambulatory device or system (i.e., a device or group of devices that may be carried by the user while the user is in locomotion on foot) may be used to measure the heart rate of a user based upon the measurement of a parameter other than the user's pulse. While, in the illustrative embodiment described herein, this measured parameter is the foot contact time (Tc) of the user, it should be appreciated that other performance parameters may alternatively be measured and used to estimate a user's heart rate (HR) in a similar fashion. For example, measured values of a user's Pace, Speed, or energy expenditure may be used to estimate the user's heart rate (HR) based upon a known relationship between such a measured value and heart rate for the user.

We have recognized that, when a user first begins walking or running, the FI values tend to be less consistent than after the user has "warmed up." Therefore, it may be desirable to wait for a period of time after a user begins walking or running to begin measuring fitness index (FI) values. Any of a number of alternative techniques can be used to implement this "waiting" function, and the invention is not limited to any particular technique for accomplishing the same. In one illustrative embodiment, for example, after a user begins walking or running, the percentage differences between consecutive FI values is determined, and FI values are accumulated for the purpose of calculating an average fitness index (FI) only after the percentage difference between consecutive FI values is less than a predetermined threshold. Alternatively, the device performing the calculations may simply wait a predetermined period of time or wait until the user has traveled a predetermined distance before it begins accumulating "good" FI values.

After a user's fitness index has leveled out during an exercise session (e.g., after the user has warmed up), the fitness index may be monitored for abnormal deviations from its expected value. Such deviations may, for example, be indicative of conditions such as dehydration, fatigue, stress, etc. In one embodiment, a user's fitness index is continuously monitored and, if it deviates from its expected value by more than a particular percentage, an indication is provided to the user that something may be wrong. As discussed above, such an indication may be provided in any of a number of ways (e.g., text, sound such as beeps or buzzers, lights, etc.), and the invention is not limited to any particular type of indication.

Based upon the average fitness index ($FI_{AVE}$) measured during each outing by a user 112, improvements in the user's fitness level will be marked by decreases in the value of $FI_{AVE}$, and decreases in the user's fitness level will be marked by increases in the value of $FI_{AVE}$. The user 112 may also compare his or her fitness index to the fitness indexes of other people, and thereby compare his or her level of fitness to that of those people. For convenience, the value of FI or $FI_{AVE}$ may be scaled by a constant value so as to yield a value that is within a common range (e.g., between "1" and "100").

While a user's fitness index (FI) is substantially constant when the user is walking or running on a flat surface, we have recognized that the calculated values of FI tend to increase slightly as the grade on which the user is walking or running increases, and tend to decrease slightly as the grade on which the user is walking or running decreases. In light of this, the calculated value of a user's fitness index for a given measured foot contact time (Tc) value, may be used to ascertain whether the user is walking or running on a grade at the time the foot contact time (Tc) is measured. As used herein, "grade" refers to the slope of a surface with respect to a level plane at the point the grade is measured. Most commonly, grade is measured in terms of the vertical rise in the surface divided by the horizontal run of the surface along a particular distance, and its value is typically expressed as a percentage. It should be appreciated, however, that the invention is not limited in this respect, and that grade may be measured in any of a number of alternative ways.

Empirical measurements have shown that a user's fitness index (FI) increases and decreases approximately linearly with corresponding increases and decreases in the value of the grade of the surface on which the user is walking or running. Therefore, once the linear relationships between FI and the current walking or running grade are known for a given user, an approximation of the actual value of the grade on which the user 112 is walking or running may be made by analyzing changes in the value of FI with respect to the value of FI when the user walks or runs on a flat (i.e., "0%") grade. Alternatively, a higher-order polynomial may be generated to more accurately reflect the actual relationship between FI and the current walking or running grade.

This information regarding the grade of the surface on which the user 112 is walking or running may be used, for example, to correct calculated values of Pace, Speed, distance traveled, and/or expended energy to account for the changes in surface grade. This value correction may be based upon a simple determination that a non-zero grade condition exists (e.g., determining that the user is on one of three surfaces: negative grade, level surface, or positive grade), or may be based upon a determination of the actual value of the grade (e.g., a percent grade). In addition, information regarding changes in surface grade can be exploited to identify changes in the altitude of the user 112 while the user is walking or running. Information regarding altitude changes may be stored in memory, along with corresponding distance measurements, and may be used for a number of purposes. For example, in one embodiment of the invention, such information may be transferred (e.g., via a wireless communication link) to the computer 428, where it may be displayed to the user in graph form. For example, a graph may be displayed that shows, for a particular outing, changes in altitude over the distance of the outing. In one embodiment, a second graph may be superimposed over the altitude/distance graph showing, for example, changes in pace over the distance of the outing. The computer 428 and/or the server 442 may analyze the received data to evaluate, for example, the degree by which a user's pace or speed changes in response to changing grades or altitudes. This information may therefore be used to provide feedback to the user regarding the effectiveness or effort level exerted during a given workout.

It should be appreciated that any of a number of other measurable variable physiological parameters (i.e., physiological parameters such as respiration rate, blood pressure, body temperature, lactate level, etc.) may alternatively or additionally be determined and combined with a measured foot contact time or other performance parameter (e.g., speed, pace, energy expenditure, etc.) to yield a calculated parameter reflecting useful information. We have recognized that at least some of such variable physiological parameters, e.g., respiration rate, are related to heart rate. Therefore, when a variable physiological parameter such as respiration rate (which is related to heart rate) is combined with a measured foot contact time or other performance parameter (e.g., pace, energy expenditure or the like), a fitness index value may be yielded in a manner similar to that in which a fitness index value is yielded when heart rate and foot contact time or another performance parameter are combined as discussed above. When applicable, the fitness index so calculated may be used in any of the ways or for any of the purposes that the fitness index described above is used. It should be appreciated, of course, that the invention is not limited to the combinations of performance parameters and variable physiological parameters that yield substantially constant values, as useful information may also be derived from combinations of performance parameters and variable physiological parameters having values that change in response to increases in the user's speed, etc. For example, a such a calculated parameter may be used as an indicator of the user's effort level during an outing. Therefore, various embodiments of the invention may combine any measured performance parameter (e.g., foot contact time, foot loft time, step time, speed, pace, energy expenditure, distance traveled, etc.) with any measured variable physiological parameter (e.g., heart rate, respiration rate, body temperature, lactate level, etc.) to yield a useful result.

As shown in FIG. 4, in one illustrative embodiment of the invention, the foot-mounted unit 102 includes an altimeter 426 to measure the current altitude (with respect to a reference altitude such as sea level) of the user 112. The altimeter 426 may be disposed on the user 112 in any of a number of ways, and need not be included in the foot-mounted unit 112.

For example, the altimeter 426 may alternatively be disposed within the wrist-mounted unit 104, the chest-mounted unit 106, or elsewhere on the user 112. The output from the altimeter 426 may be exploited in any of a number of ways. For example, information from the altimeter 426 may be stored in memory and/or transferred to the computer 428 or the server 442 for display on the display 438 and/or analysis, as discussed above.

In one embodiment, the output from the altimeter 426, together with distance traveled measurements, may be used to determine a grade of the surface on which the user 112 is walking or running. This determination of grade may then be used to calculate or correct calculated values such as Pace, Speed, distance traveled, energy expenditure, and the like, in a manner similar to that discussed above. Such performance parameters therefore may be calculated based upon measured altitudes of the user.

As discussed above, information regarding any of the parameters and values discussed herein may be transmitted from the foot-mounted unit 102 and/or the wrist-mounted unit 104 to the computer 428, and possibly the network server 442. Once this information is so transferred, software executing on the computer 428 and/or the network server 442 may analyze and/or process it so as to provide meaningful feedback to the user, for example, in the form of graphs, charts, data logs, etc. For example, the user may view (e.g., on the display 438) displayed information such as graphs (e.g., time lapse graphs), charts, and/or data logs representing: (1) daily, weekly, monthly, yearly values (and/or any of the forgoing measured to date) of: (a) total distance traveled while walking and/or running, (b) total time spent walking and/or running, (c) average pace or speed while walking and/or running, and/or (c) average fitness index; (2) average pace, speed, heart rate, stride length, cadence (stride rate), caloric burn rate, acceleration, and/or elevation per unit of choice (e.g., per mile or per minute) during a particular outing; and/or (3) mileage traveled by, or an amount of accumulated stress encountered by, a respective pairs of running shoes or by a particular user; etc. A few examples of such graphs and charts that may be displayed to the user are discussed below in connection with FIGS. 33A-37. When appropriate, any combination of the above-identified items may be combined on the same graph so as to "tell the story" of a particular outing. For example, a user's average pace, heart rate, and course elevation, may be shown simultaneously on a per-unit distance (e.g., per mile) basis, thereby giving the person reviewing the graph sufficient information to understand the correlation between changes in such values during the race, e.g., a significant increase in elevation may be found to correlate with the user's decrease in speed and increase in heart rate, or vice versa.

The graphs of FIGS. 33A-36B and the chart of FIG. 37 illustrate examples of how different types of information may be displayed to the user (e.g., using the display 438 of the computer 428) based upon data accumulated while the user is in locomotion on foot (i.e., data accumulated using an ambulatory device).

Figure 33A:
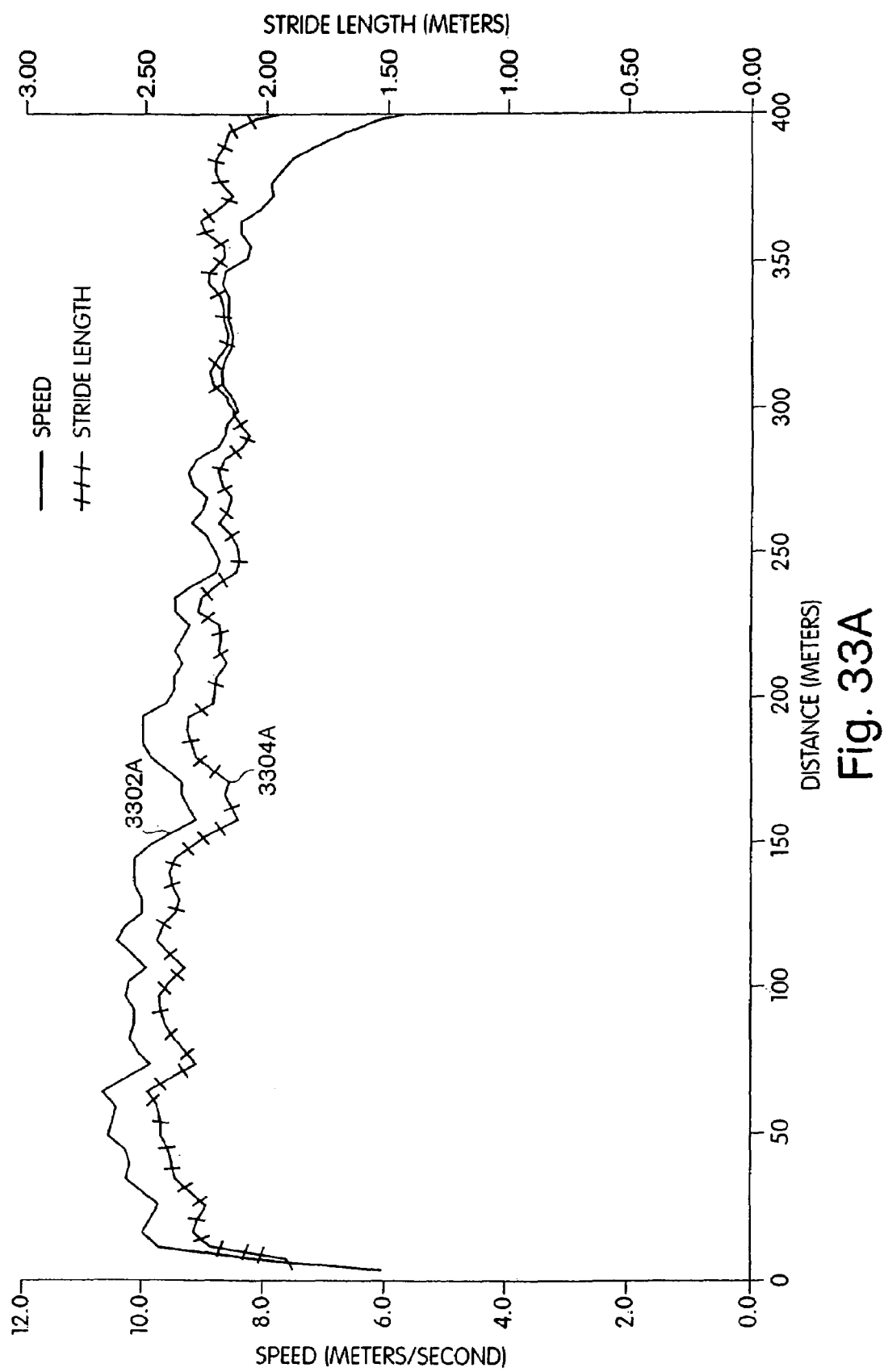
FIG. 33A is a graph showing each of speed and stride length as a function of distance for a user running a four hundred meter race.
Figure 33B:
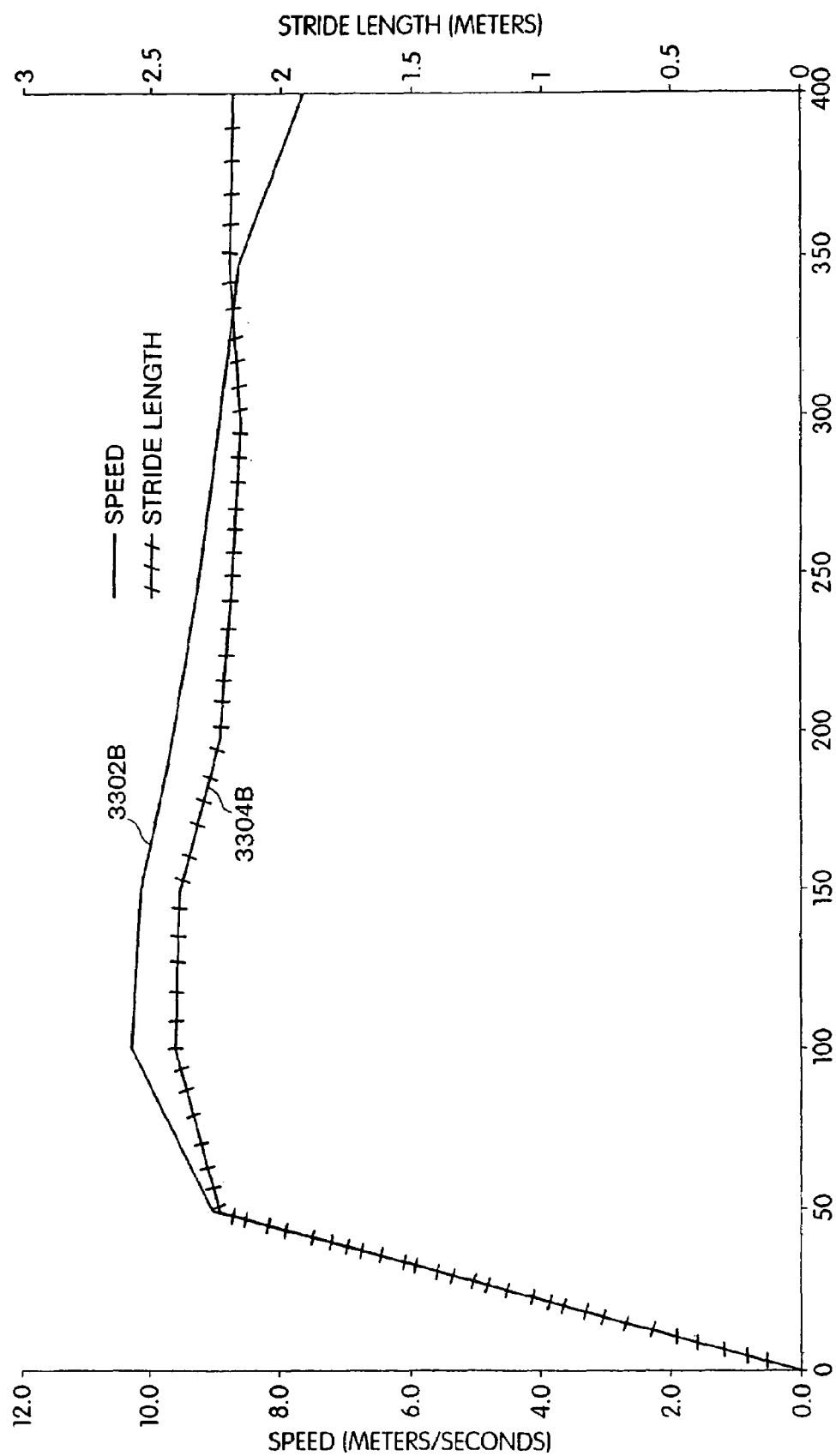
FIG. 33B is a graph similar to FIG. 33A except that values of speed and stride length are averaged over fifty meter intervals.

The graph of FIG. 33A shows both measured speed and measured stride lengths of the user as a function of distance during a four hundred meter race. Specifically, the curve 3302A represents the measured speed of the user 112 as a function of distance during the race, and the curve 3304A represents measured stride lengths of the user 112 as a function of distance during the race. Curves 3302B and 3302B in the graph of FIG. 33B are based upon the same values as are the curves 3302A and 3302A, respectively; however, the values shown therein have been averaged over fifty meter intervals. The stride length of a user is the distance between locations where the left foot and the right foot of the user, or vice versa, make contact with the ground during a complete footstep (defined above) taken by the user. A user's stride length therefore may be calculated by dividing the distance traveled during a complete footstep by two. The stride length for a given footstep may be calculated, for example, either (1) by dividing the measured step time (Ts) for the footstep by two times the calculated pace during the footstep (i.e., Ts/(2*Pace)(and converting to different units, if desired), or (2) by multiplying the calculated speed during the footstep by the measured step time (Ts) for the footstep, and dividing the result by two (i.e., Ts*Speed/2) (and converting to different units, if desired).

Figure 34A:
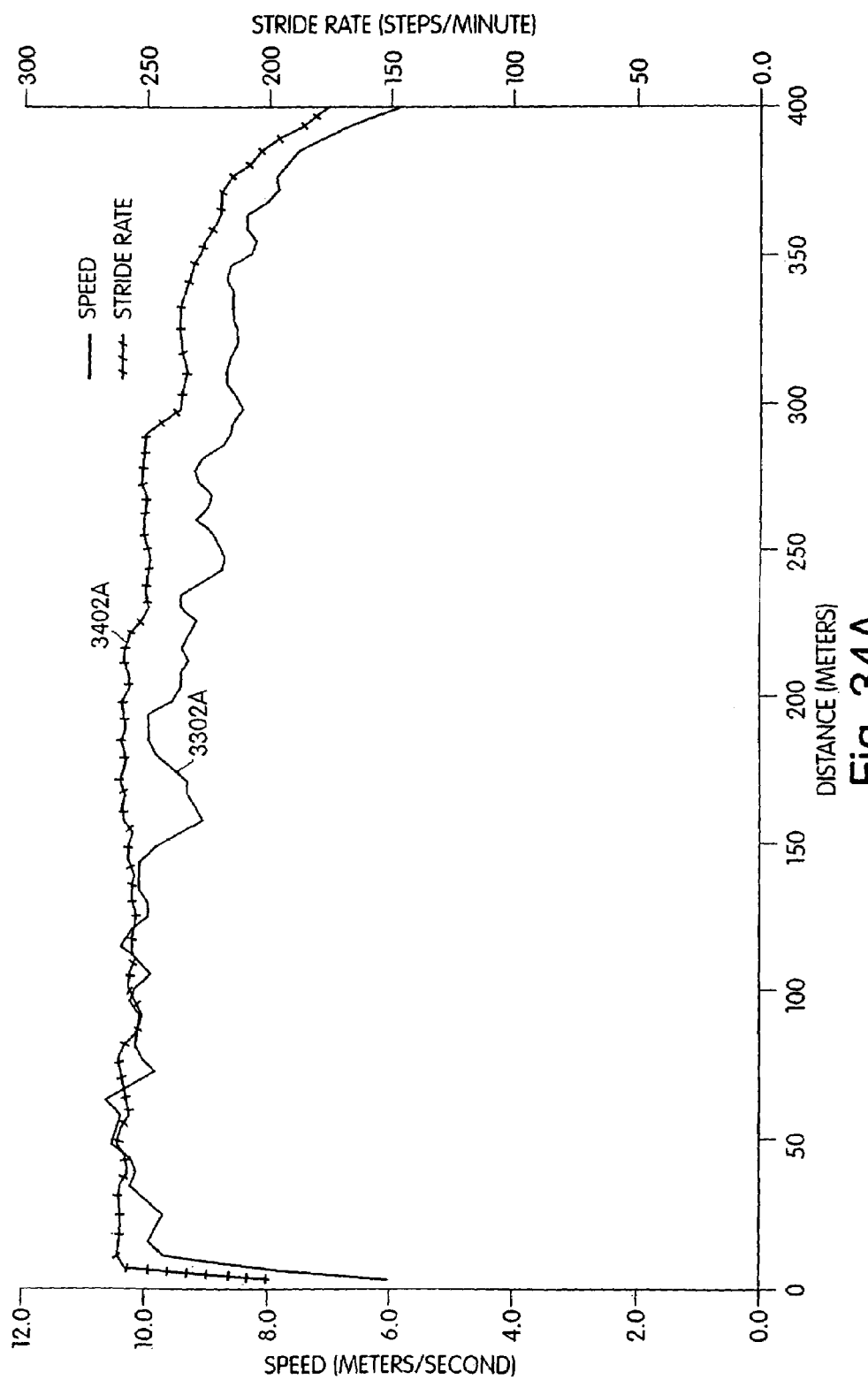
FIG. 34A is a graph showing each of speed and stride rate as a function of distance for a user running a four hundred meter race.
Figure 34B:
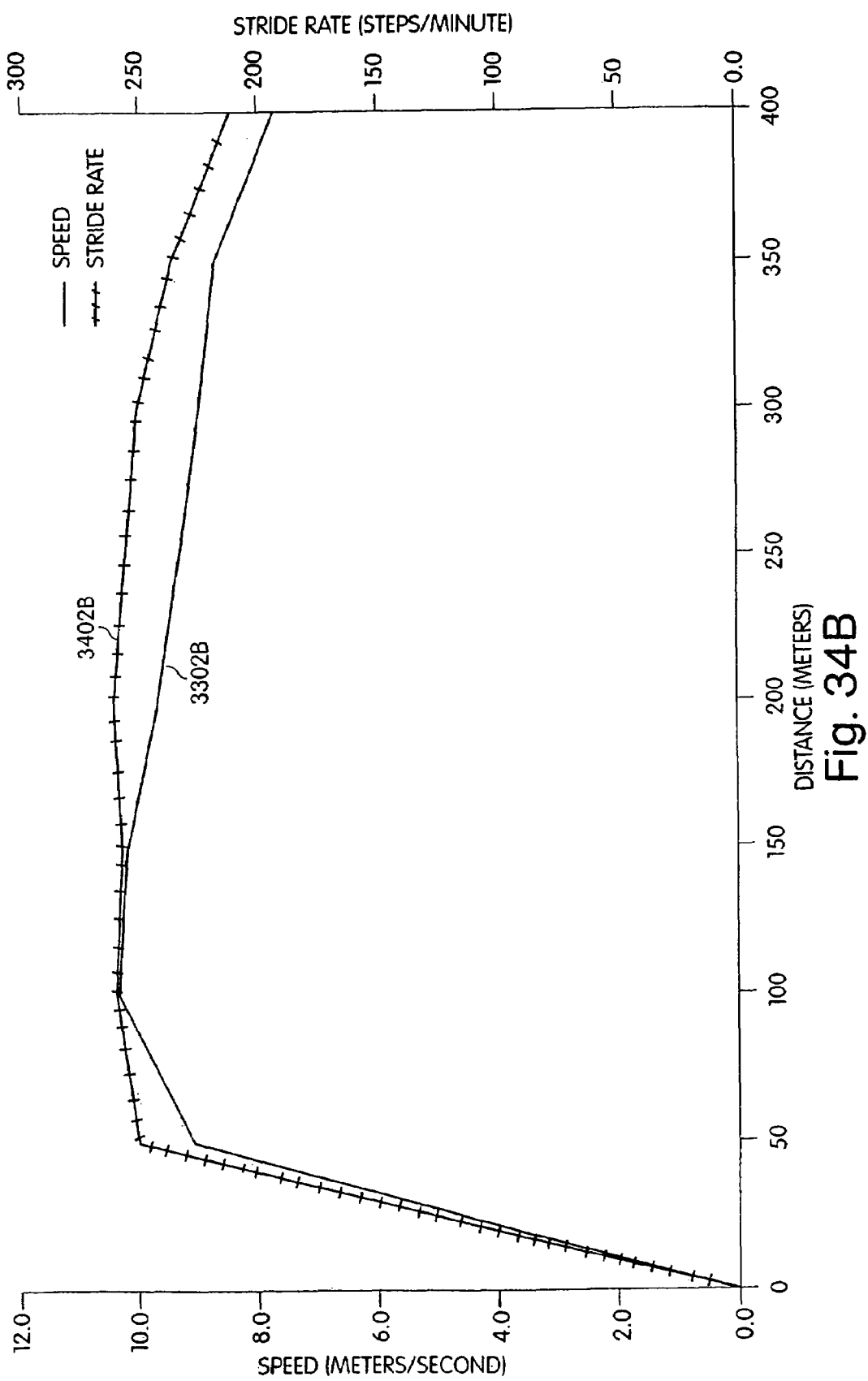
FIG. 34B is a graph similar to FIG. 34A except that the values of speed and stride rate are averaged over fifty meter intervals.

The graph of FIG. 34A shows both measured speed and measured stride rate (cadence) of the user as a function of distance during a four hundred meter race. Specifically, the curve 3302A represents the measured speed of the user 112 as a function of distance during the race, and the curve 3402A represents the cadence of the user 112 as a function of distance during the race. Curves 3302B and 3402B in the graph of FIG. 34B are based upon the same values as are the curves 3302A and 3402A, respectively; however, the values shown therein have been averaged over fifty meter intervals. The cadence for each footstep may be calculated, for example, by taking the inverse of the measured step time (Ts) for that footstep, and (if desired) adjusting the units of the value so obtained to a typical measure such as steps/minute.

Figure 35A:
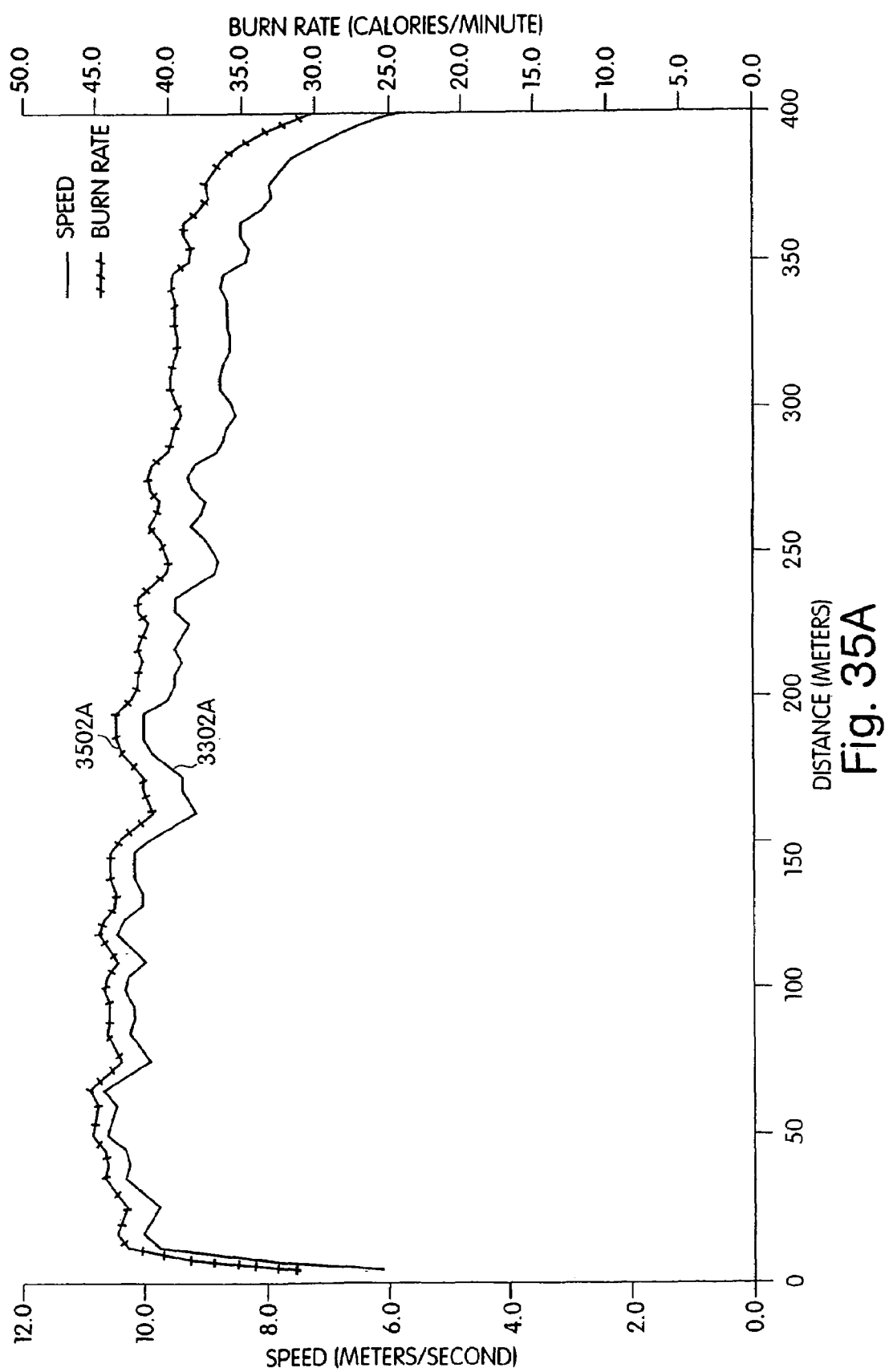
FIG. 35A is a graph showing each of speed and caloric burn rate as a function of distance for a user running a four hundred meter race.
Figure 35B:
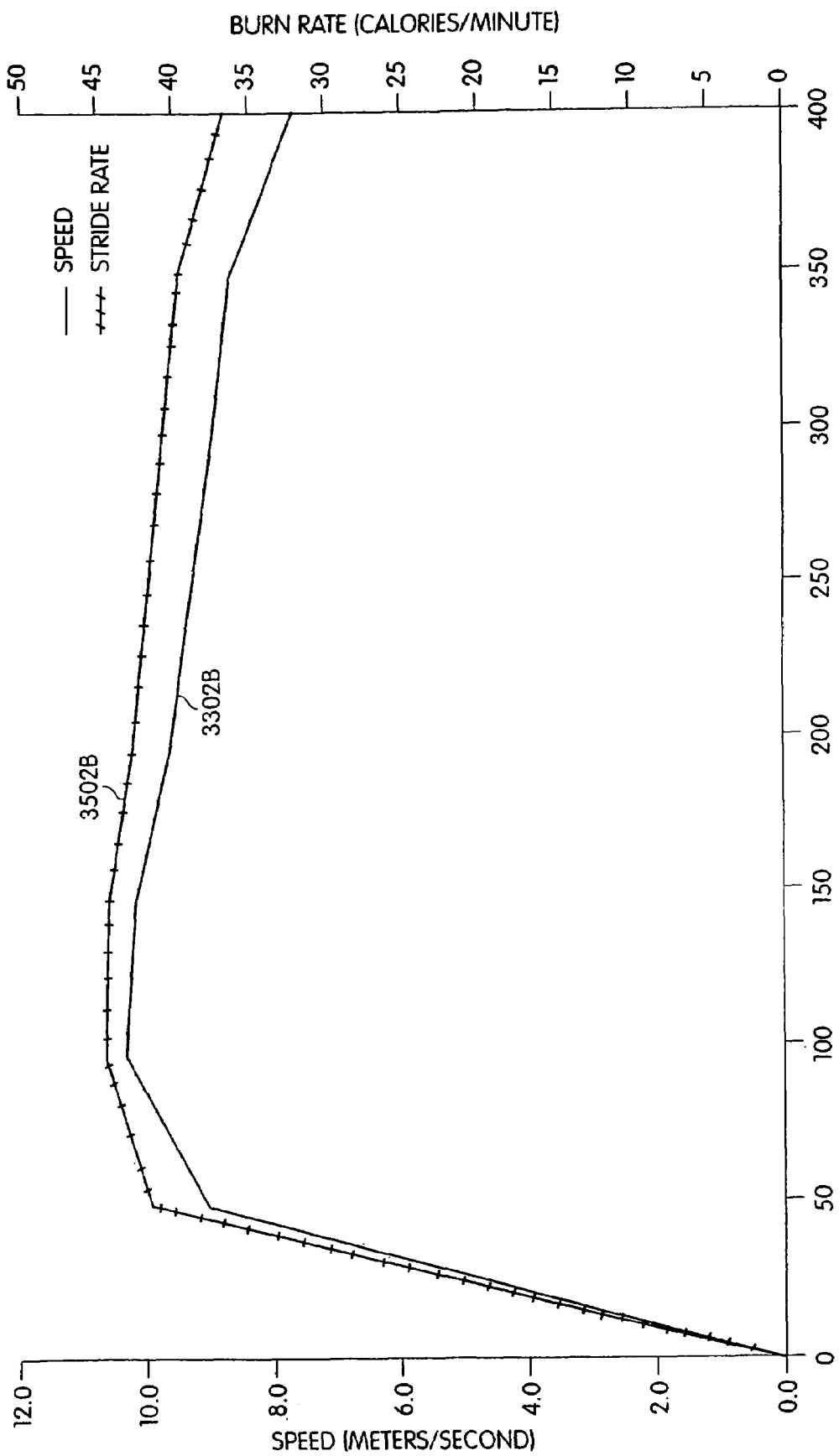
FIG. 35B is a graph similar to FIG. 35A except that the values of speed and caloric burn rate are averaged over fifty meter intervals.

The graph of FIG. 35A shows both measured speed and measured caloric burn rate of the user as a function of distance during a four hundred meter race. Specifically, the curve 3302A represents the measured speed of the user 112 as a function of distance during the race, and the curve 3502A represents the caloric burn rate of the user 112 as a function of distance during the race. Curves 3302B and 3502B in the graph of FIG. 35B are based upon the same values as are the curves 3302A and 3502A, respectively; however, the values shown therein have been averaged over fifty meter intervals. The caloric burn rate for each footstep may be calculated, for example, in the manner described in U.S. Pat. No. 5,925,001, incorporated by reference above.

Figure 36A:
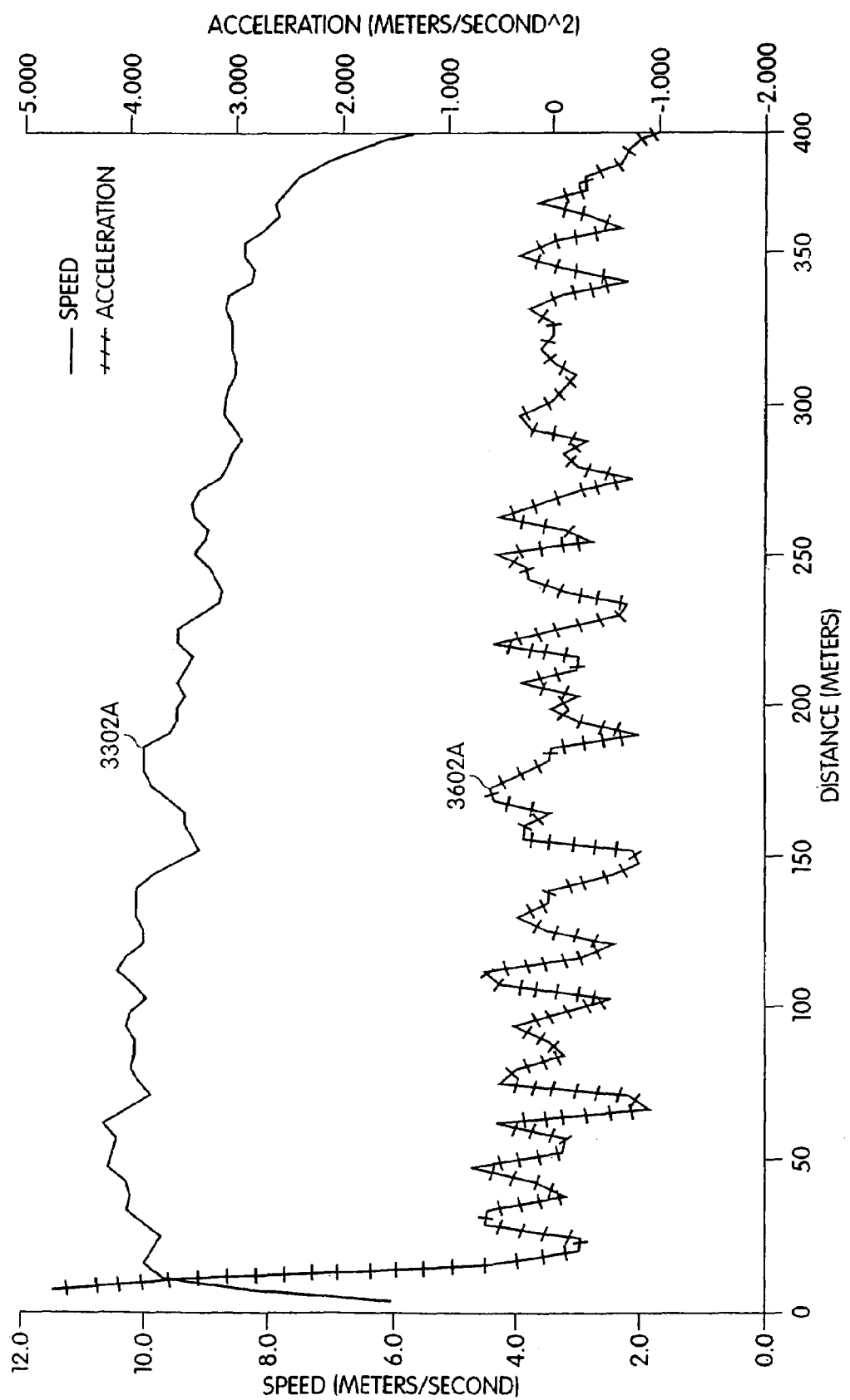
FIG. 36A is a graph showing each of speed and acceleration as a function of distance for a user running a four hundred meter race.
Figure 36B:
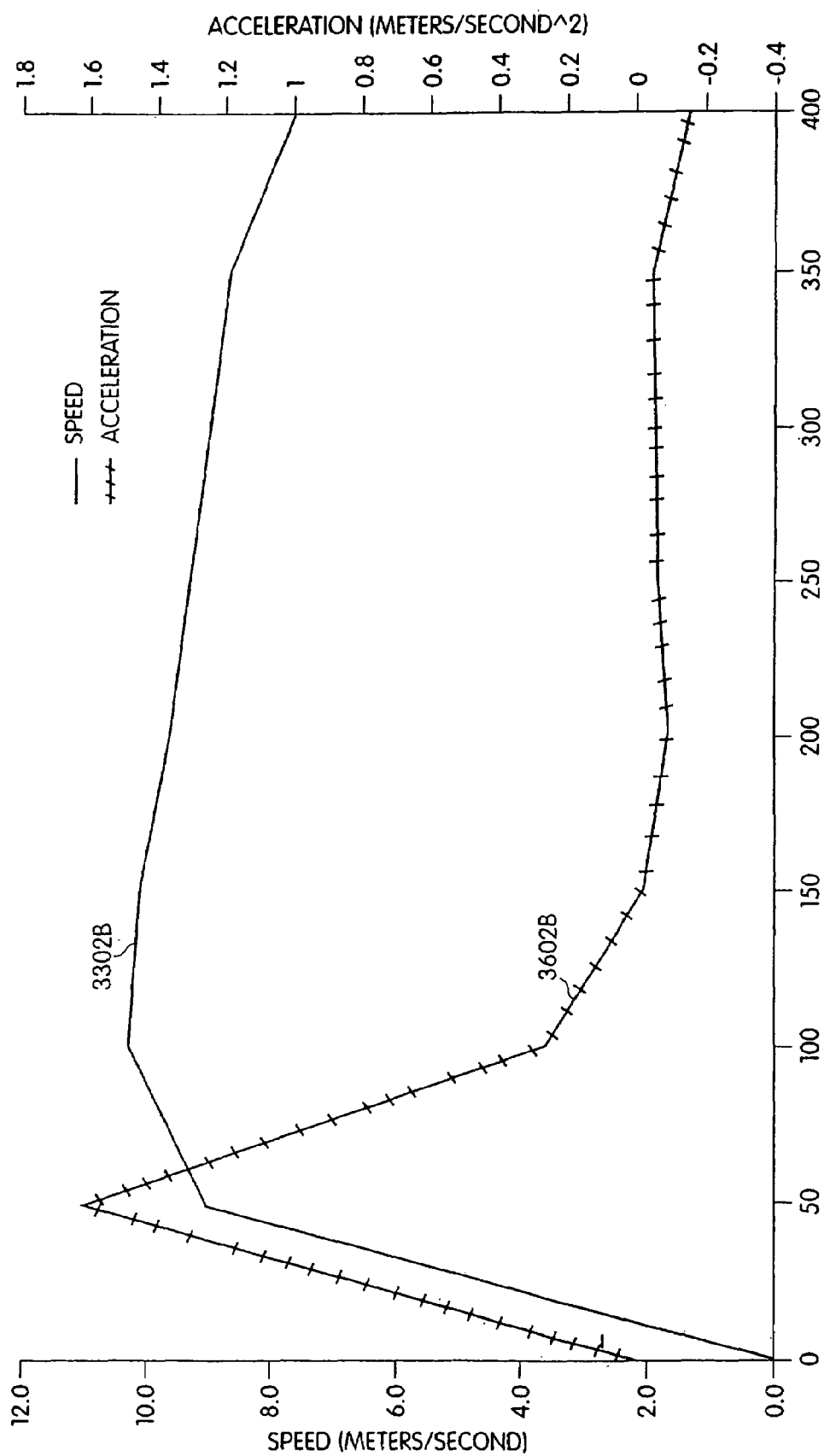
FIG. 36B is a graph similar to FIG. 36A except that the values of speed and acceleration are averaged over fifty meter intervals.

The graph of FIG. 36A shows both measured speed and measured acceleration of the user as a function of distance during a four hundred meter race. Specifically, the curve 3302A represents the measured speed of the user 112 as a function of distance during the race, and the curve 3602A represents the acceleration of the user 112 as a function of distance during the race. Curves 3302B and 3602B in the graph of FIG. 36B are based upon the same values as are the curves 3302A and 3602A, respectively; however, the values shown therein have been averaged over fifty meter intervals. The acceleration for each footstep may be calculated, for example, by calculating the change in speed between footsteps (e.g., by subtracting the speed measured during the footstep succeeding the current footstep from the speed measured during the footstep preceding the current footstep), and dividing that value by the measured step time (Ts) for the current footstep (and converting to different units, if desired).

The chart of FIG. 37 includes entries for race time, split time, average speed (both meters-per-second and miles-per-hour), average stride length (both meters and feet), average stride rate, average caloric burn rate, total calories burned, and acceleration, each calculated based upon fifty meter intervals of a four hundred meter race.

Figure 38:
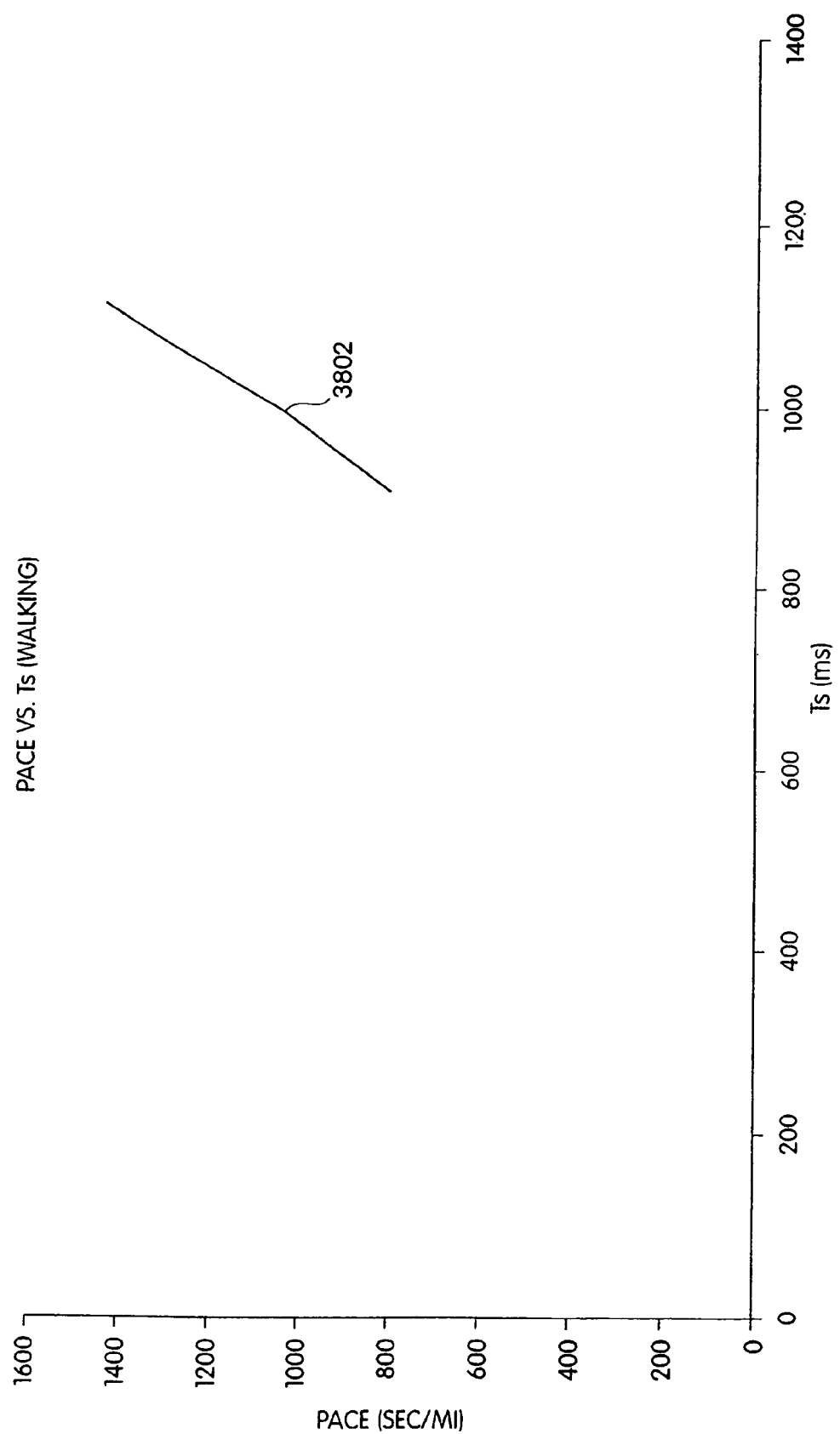
FIG. 38 is a graph showing the relationship between pace and step time (Ts) for a user over a reasonable range of walking speeds.
Figure 39:
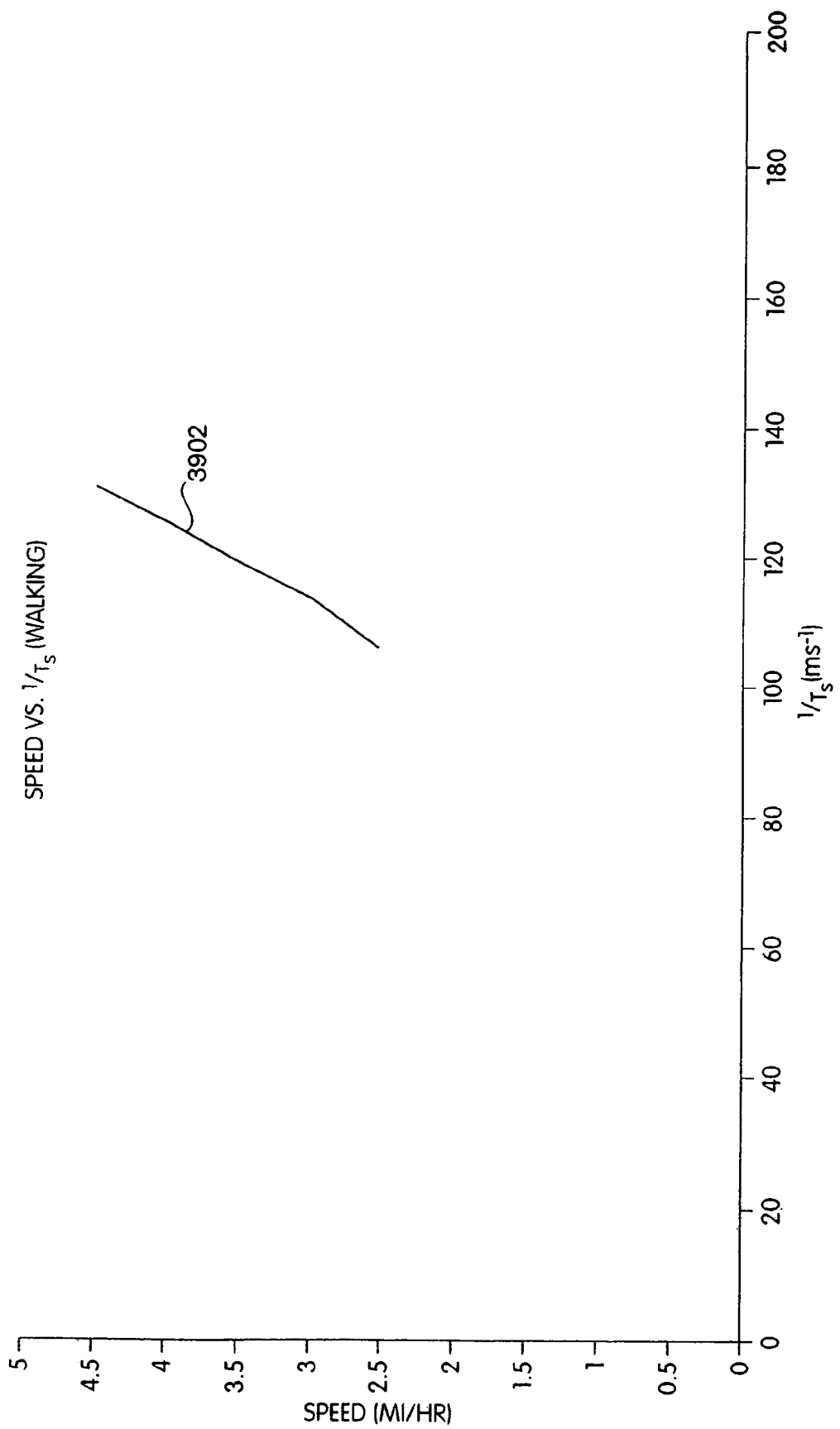
FIG. 39 is a graph showing the relationship between speed and the inverse of step time (1/Ts) for a user over a reasonable range of walking speeds.

In addition to calculating pace based upon the measured foot contact time for a footstep (as discussed above in connection with FIG. 8), and calculating speed based upon the inverse of the measured foot contact time for a footstep (as discussed above in connection with FIG. 13), we have discovered that it is also possible to calculate the Pace of a user during a particular footstep based upon the measured step time (Ts) for that footstep, and to calculate the Speed of the user during a particular footstep based upon the inverse value of the measured step time (1/Ts) for that footstep. Examples of empirically measured relationships between Pace and Ts and between Speed and 1/Ts for a particular user 112 (when the user 112 is walking) are shown as lines 3802 and 3902 in FIGS. 38 and 39, respectively. Because these relationships are approximately linear, linear equations can be derived that define them with substantial precision, and such equations can be used to calculate the pace and/or speed of the user while the user is in locomotion on foot simply by measuring the step times of the user. These lines may be identified and calibrated for a particular user using any of the techniques discussed above in connection with the Pace vs. Tc and Speed vs. 1/Tc lines. The measured values of Speed and/or Pace obtained using the relationships of FIGS. 38 and 39 can also be used in any of the ways and for any of the purposes discussed elsewhere herein. For example, parameters such as distance traveled, average speed, average pace, etc. may be calculated based upon the calculated Speed and/or Pace values. Although only the "walking" curves 3802 and 3902 are shown in FIG. 38, it should be appreciated that separate, different lines or curves may also be employed to calculate Speed and/or Pace values, based upon measured step times, when the user 112 is running. Whether a "walking" or "running" line is to be used for a particular footstep may be determined in the same or similar manner as is done in connection with the Pace vs. Tc and Speed vs. 1/Tc curves discussed above.

It is known that the average amount of force ($F_{AVE}$) exerted on the ground by a user during a footstep taken by the user may be calculated using the equation (29) below:

$$F_{AVE}=(Ts*W)/(2*Tc) \quad (29)$$

wherein "W" is equal to the weight of the user.

In one embodiment of the invention, Ts and Tc values are measured during respective footsteps of the user during an outing, and the equation (29) is used to measure a value representing a total amount of stress exerted by the user (Accumulated Stress) during that outing. One way this can be accomplished is by maintaining a running total of per-footstep average force measurements (calculated using the equation (29)) throughout the outing, e.g., using the equation (30) below:

$$\text{Accumulated Stress}=\Sigma F_{AVE}=\Sigma(W*Ts)/(2*Tc). \quad (30)$$

Alternatively, average values of Tc and Ts can be calculated for the outing and can be inserted in the equation (29) to obtain a value of $F_{AVE}$. The value of $F_{AVE}$ so obtained then can be multiplied by the number of steps taken by the user to yield the value of Accumulated Stress. In either case, foot-mounted unit 102 and/or the wrist-mounted unit 104 may obtain the values of Ts and Tc, and either of these units, or one or more other devices, such as the computer 428 and/or the network server 442, may be employed to calculate the values of FAVE and/or Accumulated Stress. It should be appreciated that the value of Accumulated stress may be scaled by a particular factor to render a value that is easier to comprehend and store in memory. In such a situation, the factor of two in the denominator of equations (29) and (30) could be omitted, as it would be included in the scaling factor that was employed.

Separate values of Force and/or Accumulated stress may be obtained for walking or running, if desired. Any of the techniques discussed above for distinguishing between occasions when the user 112 is walking or running may be employed for this purpose.

Values of Accumulated Stress may also be accumulated over more than one outing, if desired. One application for this type accumulated information is to measure the amount of stress encountered by a pair of shoes over the lifetime of the shoes. The stress accumulated on a per-outing basis can also be employed by a user to permit the user to gauge the stress encountered during each outing, and adjust or plan his or her workout routine accordingly to minimize the risk of injury or to optimize a workout regime during the current workout or during future workouts. For example, a beginning runner may be advised to increase the amount of stress encountered during successive runs at a gradual rate, and thereby minimize the risk of overexertion before his or her body is physically conditioned to withstand certain levels of stress.

We have recognized that, when Accumulated Stress is measured as discussed above, as the Speed of the user increases (and the user's Pace decreases accordingly), the amount of Accumulated Stress exerted per unit of time (e.g., per minute) tends to increase, whereas the amount of Accumulated Stress per unit of distance (e.g., per mile) tends to decrease. This phenomenon is illustrated both in the chart of FIG. 40 and the graph of FIG. 41.

Figure 41:
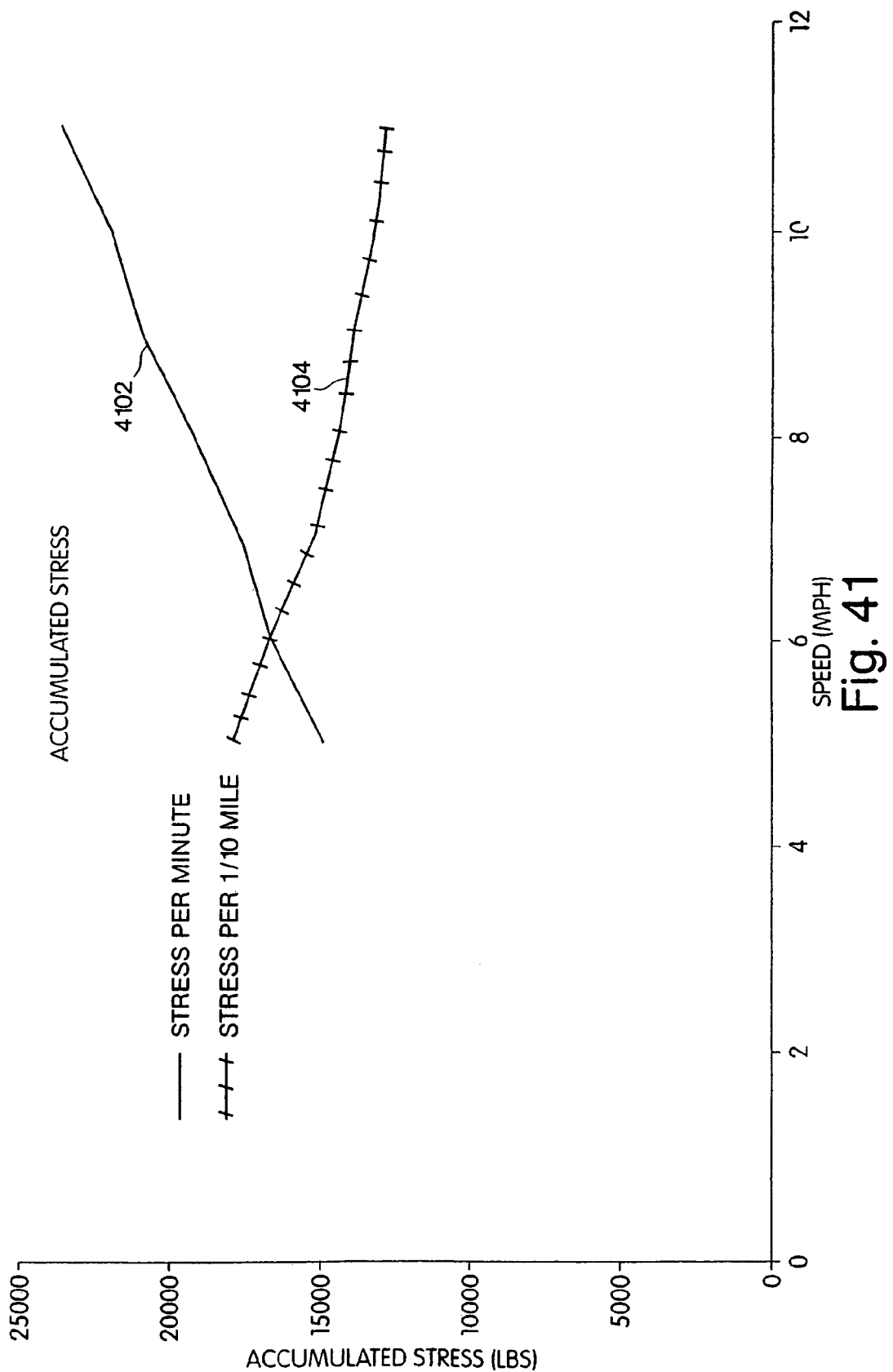
FIG. 41 is a graph showing the relationship between a user's speed and accumulated stress values, measured both per unit time and per unit distance.

In the chart of FIG. 40, average values of Tc and Ts for a particular user (weighing 150 pounds) traveling at each of several paces and speeds are used to calculate corresponding values of average ground force using the equation (29). The chart of FIG. 40 also shows values of Stress Per "1/10" Mile and Stress Per Minute, with each of these values being calculated by multiplying the average ground force value by the number of steps taken during the corresponding time or distance interval. The curve 4102 in FIG. 41 represents the relationship between Accumulated Stress measured on a per-minute basis for a particular user and the Speed of the user. The curve 4104 in FIG. 41 represents the relationship between Accumulated Stress measured on a per—1/10mile basis for a particular user and the Speed of the user. If desired, these types of charts or curves for Accumulated Stress, or other information calculated based thereupon, can be generated and displayed using any of the devices in the system of FIG. 4.

It should be understood that each of the features, techniques, and capabilities of the devices and systems described herein may be employed in combination with any of the other described features, techniques, and capabilities, and the invention is not limited to the particular combinations of features, techniques, and capabilities described herein. For example, any of the described features, capabilities, or techniques with regard to the display of certain performance parameters and/or variable physiological parameters, or graphs, charts, etc., based thereon, can be employed in combination with any of the described features, capabilities or techniques involved with accumulating data during footsteps taken by the user, or performing or optimizing calculations based thereupon (e.g., calibrating Pace vs. Tc or Ts and/or Speed vs. 1/Tc or 1/Ts lines).

Having thus described at least one illustrative embodiment of the invention, various alterations, modifications and improvements will readily occur to those skilled in the art. Such alterations, modifications and improvements are intended to be within the spirit and scope of the invention.

Accordingly, the foregoing description is by way of example only and is not intended as limiting. The invention is limited only as defined in the following claims and the equivalents thereto.

What is claimed is:

1. A method, comprising steps of:
   (a) identifying an average foot contact time o a user during a first outing;
   (b) identifying an average pace of the user during the first outing;
   (c) determining a relationship between foot contact times of the user and corresponding paces of the user, wherein the relationship is based upon the average foot contact time and the average pace identified during the first outing, and wherein no other average foot contact times and no other average paces identified during any different outings by the user are used to define the relationship;
   (d) determining at least one foot contact time of the user during a second outing; and
   (e) calculating a pace of the user during the second outing based upon the determined at least one foot contact time and the determined relationship between foot contact times of the user and corresponding paces of the user.

2. The method of claim 1, wherein:
   the step (d) comprises determining a plurality of foot contact times of the user during the second outing; and
   the method further comprises a step of (f) calculating a distance traveled by the user during the second outing based upon the determined plurality of foot contact times and the determined relationship between foot contact times of the user and corresponding paces of the user.

3. The method of claim 1, wherein:
   the step (a) includes steps of (a1) determining a plurality of foot contact times during the first outing, and (a2) calculating the average foot contact time of the user during the first outing based upon the plurality of determined foot contact times; and
   the step (b) includes steps of (b1) determining an amount of time that elapsed during the first outing, and (b2) calculating the average pace of the user during the first outing based upon the amount of time that elapsed during the outing and the distance traveled during the outing.

4. A method, comprising steps of:
   (a) determining a single user-specific calibration constant that defines a relationship between foot contact times of a user and corresponding paces of the user, wherein no other user-specific calibration constants are used to define the relationship;
   (b) determining at least one foot contact time of the user during an outing; and
   (c) calculating a pace of the user during the outing based upon the determined at least one foot contact time and the relationship between foot contact times of the user and corresponding paces of the user that is defined by the single user-specific calibration constant.

5. The method of claim 4, wherein:
   the step of (b) comprises determining a plurality of foot contact times of the user during the outing; and
   the method further comprises a step of (d) calculating a distance traveled by the user during the outing based upon the determined plurality of foot contact times and the relationship between foot contact times of the user and corresponding paces of the user that is defined by the single user-specific calibration constant.

* * * * *

UNITED STATES PATENT AND TRADEMARK OFFICE
CERTIFICATE OF CORRECTION

PATENT NO. : 7,428,471 B2  
APPLICATION NO. : 11/588589  
DATED : September 23, 2008  
INVENTOR(S) : Jesse Darley et al.

Page 1 of 1

It is certified that error appears in the above-identified patent and that said Letters Patent is hereby corrected as shown below:

In Column 75, Claim 1, Line 8:
The word "o" has been replaced with --of--.

Signed and Sealed this

Twenty-third Day of December, 2008

JON W. DUDAS  
*Director of the United States Patent and Trademark Office*